United States Patent [19]
Kahne et al.

[11] Patent Number: 6,040,433
[45] Date of Patent: Mar. 21, 2000

[54] SULFINYL HEXOSE DERIVATIVES USEFUL FOR GLYCOSYLATION

[75] Inventors: Daniel E. Kahne, Princeton, N.J.; Lin Yan, Cambridge, Mass.

[73] Assignee: The Trustees of Princeton University, Princeton, N.J.

[21] Appl. No.: 08/822,131

[22] Filed: Mar. 21, 1997

Related U.S. Application Data

[60] Provisional application No. 60/013,800, Mar. 21, 1996.
[51] Int. Cl.⁷ ........................................................ C07G 3/00
[52] U.S. Cl. .................... 536/4.1; 536/18.5; 536/123.13; 536/124
[58] Field of Search ..................................... 536/4.1, 18.5, 536/123.13, 124

[56] References Cited

PUBLICATIONS

I. Alonso et al. *"A New Promoter System for the Sulfoxide Glycosylation Reaction."* pp. 1477–1480, vol. 37, issue 9, Feb. 26, 1996.
Search report for PCT/US97/04638; Jul. 24, 1997.
Khiar et al. J. Org. Chem. Oct. 20, 1995, 60(21), 7017–7021.

*Primary Examiner*—Kathleen K. Fonda
*Attorney, Agent, or Firm*—Gilberto M. Villacorta; Pepper Hamilton LLP

[57] ABSTRACT

Hexose derivatives are described which facilitate control over the stereochemistry of the glycosyl bond formed in the course of a solid phase glycosylation reaction. Methods for their use are also described.

12 Claims, 10 Drawing Sheets

6,040,433

SULFINYL HEXOSE DERIVATIVES USEFUL FOR GLYCOSYLATION

This application claims priority from Provisional Application No. 60/013,800 filed Mar. 21, 1996.

1. FIELD OF THE INVENTION

The present invention relates to the field of carbohydrate synthesis. It provides a set of hexose derivatives which are characterized by their ability to glycosylate, under appropriate conditions, a wide range of substrates in high chemical yield and with high stereo selectivity. The compounds of the invention are useful for the synthesis of carbohydrates and other glycosylated materials, and are especially suitable for the synthesis of carbohydrates on polymeric supports. In particular, they are suitable for the synthesis of carbohydrate libraries by parallel or combinatorial methods.

2. BACKGROUND

Oligosaccharides and polysaccharides, as components of glycoproteins and glycolipids, are ubiquitous on cell surfaces where they function as cell-surface markers that protein receptors can recognize. Although such carbohydrate-mediated cell-cell interactions are of importance in many biological events, our understanding of the structure-function relationships has been very slow to develop because of the difficulty of synthesizing well-defined oligosaccharides for study.

Carbohydrate ligands play central roles in a wide variety of normal and abnormal biological recognition processes. Among their less benign roles, carbohydrates on cell surfaces have been implicated in chronic inflammation, in viral and bacterial infection, and in tumorigenesis and metastasis. Strategies to block the interactions between cell surface carbohydrates and their protein receptors could provide an effective means of preventing or treating various diseases. Antibodies directed to either the carbohydrate ligands or to their respective receptors represent one approach; another strategy is to deploy ligands which bind to the protein targets better than the natural cell surface carbohydrates. Consequently, there is great potential for, and a great amount of research into, the use of synthetic oligosaccharides as therapeutic agents.

One application of synthetic oligosaccharides is for the inhibition of cell adhesion. For example, a critical step in the inflammatory response is the adhesion of circulating neutrophils to the endothelial lining of blood vessels, which is an essential precursor to neutrophil infiltration of the surrounding tissue. The neutrophils initially adhere via carbohydrate ligands to adhesion molecules (selecting) and then, in the presence of pro-inflammatory chemokines, they bind more tightly via a family of cell adhesion molecules (CAMs) called integrins. The integrins incorporate carbohydrate ligands that bind to intracellular adhesion molecules (ICAMs) on the epithelium. There is currently great interest in synthetic carbohydrate ligands that might interfere with selectin and/or integrin binding; such agents are expected to be of use in the treatment of asthma, ARDS, reperfusion injury, multiple sclerosis, and various other chronic inflammatory diseases.

Another example of this application of synthetic carbohydrates is the inhibition of bacterial adhesion to human tissue. Many pathogenic bacteria adhere to carbohydrate ligands on the host cells, and this adhesion can be blocked by the appropriate synthetic oligosaccharide. For many bacteria, colonization is impossible without adhesion, and carbohydrate-based therapies for several infectious diseases, such as H. pylori-induced ulcers and pneumonia, are currently being developed.

Certain oligosaccharides are of utility for the induction of immune responses, for antibody production, as vaccines, or to induce disease states in research animals. For example, the trisaccharide nephritogenoside is used to induce glomerulonephritis in animals, and has received the attention of synthetic chemists for some time: H. Zhang, Y. Wang, W. Voelter, *Tetrahedron Lett.*, 36, 1243–1246 (1995) and references therein.

Despite the promise of synthetic oligosaccharides for research and therapeutic applications, there is at present no universally applicable method for the synthesis of these complex molecules. Enzymatic methods have been developed recently which are quite effective for the regiospecific and stereospecific formation of glycosidic linkages, but the enzymes are fairly specific for particular substrates and not widely applicable to the variety of structures one would like to synthesize. See: O. Karthaus et al, *J. Chem. Soc. Perkin Trans.* 1, 1851–1857 (1994); M Schuster, P. Wang, J. Paulson, C.-H. Wong, *J. Amer. Chem. Soc.*, 116, 1135 (1994); and references therein.

Chemical synthesis is not limited in this fashion, and in principle is capable of providing any desired oligosaccharide, and therefore carbohydrate synthesis has become a very active field of research. Novel glycosylation reactions and clever strategies for carbohydrate synthesis have been developed. Some fairly complex oligosaccharides have been synthesized, but to date there is no generally applicable "universal" method that can reliably generate glycosidic linkages with control of regiochemistry and stereochemistry. Subtle changes in the structures of glycosyl donors and acceptors change the regiochemical and stereochemical outcomes, and on the yields, of existing glycosylation reactions. Consequently, every oligosaccharide synthesis is a unique undertaking. This state of affairs does not permit the synthesis of large libraries of oligosaccharides for screening purposes. The application of combinatorial methods of synthesis requires especially reliable chemistry, and the combinatorial synthesis of oligosaccharide libraries is therefore well beyond the reach of present methods.

Thus, although the power of combinatorial synthesis for identifying drug leads and elucidating structure-activity relationships may have been appreciated for some time in specific areas of drug discovery, the combinatorial approach has not been successfully applied to the synthesis and screening of carbohydrate-based ligands, including, for example, polysaccharides and glycoconjugates. In contrast, methods to make peptides and nucleic acids on solid supports have been available for many years and so it is not surprising that the first combinatorial libraries involved peptides and nucleic acids. In contrast, methods to synthesize carbohydrates on the solid phase are only now being developed. The reliable preparation of a combinatorial oligosaccharide library requires consistently high-yielding reactions, which give well-defined products from a variety of substrates under standardized reaction conditions.

A related requirement is the availability of a set of stable carbohydrate monomers that are suitable for these reactions. These monomers should not only add to the growing oligosaccharide chain in high yield, but should carry suitable protecting groups that can be selectively removed to enable attachment of the next monomer unit. Similar requirements apply to the incorporation of carbohydrate monomer units into non-oligosaccharide libraries (e.g., glycopeptides or glycoproteins). Such a set of monomers would, of course, be useful for solid-phase or solution-phase synthesis of individual simple and complex carbohydrates, as well.

Synthesis of combinatorial libraries, especially on solid supports, puts great demands on the chemistry employed. Each step in a multi-step combinatorial library synthesis should provide the desired product with high yield, otherwise the final yield of the expected products drops to low levels. The number of by-products rises to unacceptable levels, after several rounds of synthesis. Even with yields at the level of 90% per reaction, the maximum amount of product that can be expected after only five consecutive reactions is 59%, 35% after ten such reactions. Moreover, such 90% or better yields must be obtained simultaneously, under the same reaction conditions, for the enormous number of different monomer/oligomer combinations that are present in a growing library.

There is a great need, therefore, for a method of linking saccharide monomers that can be relied on to generate regiochemically and stereochemically well defined products in high yield. Such a method would allow research workers other than skilled synthetic chemists to engage in the preparation of oligosaccharides. Likewise, there is a need for a synthetic methodology that is reliable enough to be carried out using automated equipment, analogous to the automated DNA and automated peptide synthesizers that are a mainstay of nucleic acid, protein chemistry and combinatorial library synthesis research. Both of these needs would be met by a reliable method of solid-phase oligosaccharide synthesis that approaches the kinds of results obtained using techniques currently available for peptides and nucleic acids.

2.1. Existing Methods of Oligosaccharide Synthesis

The requirements of the field of solid-phase oligosaccharide synthesis have been evident to the workers in the field of carbohydrate synthesis and much effort has, in fact, been invested in the development of various approaches with mixed results.

For instance, Schuerch et al., in *Carbohydrate Res.* (1972) 22:399–412, utilized glycosyl bromides as glycosyl donors to form glycosidic linkages to a polymer-supported glycosyl acceptor. However, the solid-phase reactions were much slower than the analogous solution-phase glycosylations. Consequently, the highly reactive and unstable glycosyl bromides underwent side reactions and eventual decomposition. Moreover, stereocontrol by C6 substituents, observed in solution, did not translate well to the solid-phase reactions. Thus, stereocontrol of the glycosidic linkages was also poor.

Gagnaire et al., in *Tetrahedron Lett.* (1972) 5065, attempted to catalyze polymer-supported glycosylation by D-glycosyl bromides with mercuric ions. They did achieve the preparation of beta(1→6) linkages on the solid phase by means of neighboring-group participation. They could not, however, obtain the alpha anomers cleanly unless the glycosyl acceptors were sterically hindered, and these hindered acceptors reduced the yield to about 55%.

Because of the additional difficulties presented by the poor transferability of solution-phase methods to solid-phase carbohydrate synthesis, some efforts to make carbohydrate libraries have involved the synthesis of mixtures of carbohydrates in solution.

In one attempt to eliminate the problems introduced by the solid-phase support, Guthrie et al. utilized a soluble polystyrene resin as a "solid" support together with an orthoester glycosylation method to obtain moderate yields of disaccharides (R. Guthrie, A. Jenkins, G. Roberts, *J. Chem. Soc. Perkin Trans.* 1, 2414 (1973)). Later, Krepinsky et al. improved on this method by utilizing a soluble polyethylene glycol polymer, and by using a glycosyl trichloroacetimidate as the glycosyl donor (S. Douglas, D. Whitfield, J. Krepinsky, *J. Amer. Chem. Soc.*, 113, 5095 (1991)). Both Guthrie and Krepinsky attempted to retain one of the advantages of solid-phase synthesis, which is the ability to wash away spent and/or excess reagents. Both methods, therefore, require precipitation of the soluble polymer by addition of specific non-solvents. The precipitation steps must be repeated several times at each step of the synthesis, resulting in substantial material losses. In addition, the precipitation steps make automation problematic and add greatly to the time required to complete a synthesis.

A further limitation imposed by soluble "solid" supports is the fact that, when used for the synthesis of carbohydrate libraries, they do not generally permit resolution; that is, the soluble supports, even when in precipitated form, do not allow the physical separation or segregation and subsequent identification of individual members (e.g., single beads) of the library. Indeed, the library obtained from such soluble supports is a mixture at the molecular level. Therefore, in most cases, deconvolution is the only available technique for identifying library members that are of interest. There thus remains a need for a method of preparing carbohydrate libraries that are particularly amenable to resolution strategies, such as chemical tagging or spatial addressing methods or direct structure determination of product removed from the solid or polymer support.

Kahne et al. (D. Kahne, S. Walker, Y. Cheng, D. van Engen, *J. Amer. Chem. Soc.*, 111, 6881–6882 (1989); S. Kim, D. Augeri, D. Yang, D. Kahne, *J. Amer. Chem. Soc.*, 116, 1766–1775 (1994)) have described a sulfoxide-mediated glycosylation reaction that is high-yielding and reliable, in terms of being applicable to a variety of substrate combinations. These authors have applied this method to solid-phase synthesis of specific oligosaccharides. L. Yan, C. Taylor, R. Goodnow, D. Kahne, *J. Amer. Chem. Soc.*, 116, 6953–6954 (1994); D. Kahne, PCT Int. Appl. Publication No. WO 94/19360 (1994). Still, where the 1,2-cis isomers of oligosaccharide products are desired, the degree of stereochemical control was found to be inadequate. *Synthetic Oligosaccharides* (ACS Symposium Series 560, 1994) p. 158.

Where the 1,2-trans isomers of glycosylation products are desired, it is well-known that they may be obtained selectively when a neighboring group at C-2 participates in the glycosylation. This process is illustrated in Scheme 1 (below), where a 2-α-acyloxy group (a typical participating group) on an L-glucosyl sulfoxide is shown to form a cyclic cationic intermediate, which directs the incoming acceptor to the β position. As mentioned, above, where 1,2-cis isomers are desired, however, the presence of a non-participating C-2 substituent is insufficient to assure "clean" production of the 1,2-cis isomer. Consequently, unless the acceptor is sterically hindered, mixtures of products cis and trans isomers are usually obtained.

This problem of lack of stereochemical control in the case of 1,2-cis linkages has been documented by others using sulfinyl glycosides as starting substrates: Y. Wang, H. Zhang and W. Voelter obtained a 2:1 α:β (cis:trans) ratio in the 6-O-glycosylation of a glucose derivative with compound III (stereochemistry=D-glucose, Ar=phenyl, all X=O, all G=benzyl) (*Z. Naturforsch.* 48b, 1143–1145 (1993)), and also a 2:1 ratio in the glycosylation of a disaccharide with the same donor (*Z. Naturforsch.* 50b, 661–666 (1995)). The same authors later reported a 4:1 α:β ratio for the former reaction (*Tetrahedron Lett.* 36, 1243–1246 (1995)). This glycosyl donor, when equipped with a C-2 participating group (III, stereochemistry=D-glucose, Ar=phenyl, all X=O, all G=benzoyl), gave exclusively the β (1,2-trans) anomer in a C-2 glycosylation reaction (T. Bamhaoud, J.-M. Lancelin, J.-M. Beau, *J. Chem. Soc. Chem. Commun.*, 1494–1496 (1992)) and, also, in a series of 6-glycosylation reactions (L. Sliedregt, G. van der Marel, J. van Boom, Tetrahedron Lett., 35, 4015–4018 (1994)). The latter authors obtained similar results with galactose-derived donors. A similar donor III with a non-participating group at C-2 (stereochemistry=D-galactose, Ar=phenyl, all X=O, all G=benzyl) did give 1,2-cis products cleanly when glycosylating galactose derivatives at C-3 and C-4; it should be noted, however, that the starting substrates constitute examples of hindered acceptors (A. Sarkar, K. Matta, *Carbohydr. Res.*, 233, 245–250 (1992)).

In the course of preparing the calicheamicin trisaccharide, the glycosyl donor, shown below, lacking a participating C-2 group, was reported to provide the α-anomer with 12:1 selectivity. In this particular case, however, the observed selectivity resulted from the equilibration of an initially formed product mixture. Thus, the stereoselectivity of the reaction itself is not high: S.-H. Kim, D. Augeri, D. Yang, D. Kahne, *J. Amer. Chem. Soc.* 116, 1766–1775 (1994).

cal yield of a single compound. As noted above, a reliable 90% or better yield at each step is minimally required for a practical multi-step library synthesis. As the number of synthetic steps rises, the required yield per step also preferably rises. The instant discussion makes it clear that no adequate methods exist in the present state of the art for the reliable construction of glycosidic linkages that present a 1,2-cis geometry, especially in the context of library synthesis, where the simultaneous α- or β-glycosylation of multiple types of starting substrates is desired.

Thus, the need for reliable methods of glycosylation, which provide good chemical yields and good stereochemical control with a wide variety of substrates, remains unmet by the state of the art. In particular, there remains a need for classes of glycosyl donors that provide 1,2-cis stereochemistry in the carbohydrate product with good chemical yields and stereochemical control, especially with unhindered acceptors.

3. SUMMARY OF THE INVENTION

Accordingly, the present invention is directed to certain carbohydrate monomers suitable for use in the sulfoxide-mediated glycosylation reaction to provide good chemical and stereochemical yields of desired glycosylation products.

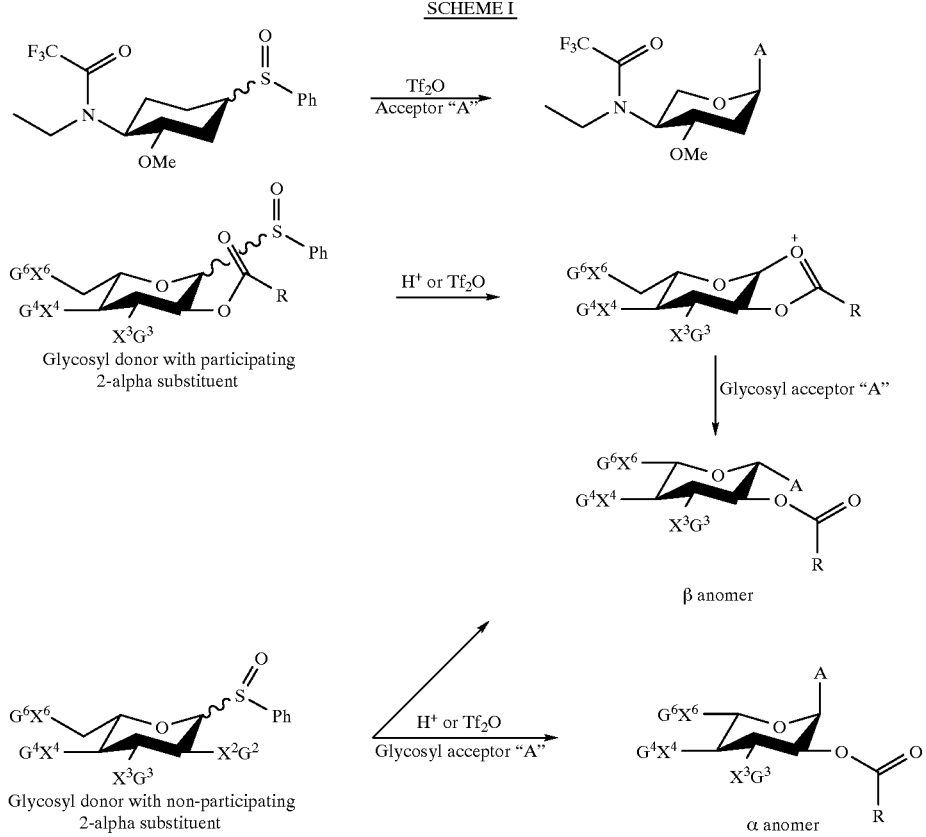

SCHEME I

The biological activity of oligosaccharides is sensitive to the stereochemistry of glycosidic linkages, and, from a biochemical, phramacologic and pharmaceutical perspective, the alpha and beta anomers of a carbohydrate are considered entirely different substances. Thus, a reaction providing a 50:50 mixture of anomers, even if it proceeds in 100% chemical yield, generates at best a 50% stereochemi- In particular, carbohydrate monomers are provided, which are capable of serving as specialized glycosyl donors that can bias the stereochemical outcome of a glycosylation reaction. In a preferred embodiment of the present invention, the resulting glycosidic linkage between the glycosyl donor and glycosyl acceptor is such that the glycosidic ring of the donor group bears substituents on the 1- and 2-positions in a cis relationship (specifically, the α anomer illustrated in Scheme I, above).

According to the present invention, a method is described which provides chemical and stereochemical yields of 90% or greater in favor of the 1,2-cis arrangement of substituents about the glycosidic ring of the reaction product obtained from the sulfoxide-mediated glycosylation reaction between an activated carbohydrate monomer, as disclosed herein, and most glycosyl acceptors.

It has been discovered that the carbohydrate monomers disclosed are useful, thus, as reagents for the synthesis of individual glycosidic moieties, whether composed substantially of one or more types of sugars or comprising glycoconjugates of varying degrees of complexity. It has further been discovered that these reagents are also useful in the preparation of carbohydrate or glycoconjugate libraries, particularly combinatorial libraries. In a preferred embodiment of the present invention, a method is described for the solid-phase synthesis of such libraries. In each case described above, the transformations leading to the glycosylation products proceed with high chemical yield. Most importantly, the stereochemical outcome of the transformations are carried out with a very high degree of control even in the absence of a participating neighboring group at the 2-position of the glycosyl donor.

Thus, the present invention is also directed to a method of controlling the stereochemical outcome of a glycosylation reaction in which a 1,2-cis configuration is formed between an acceptor attached via a glycosidic linkage to the 1-position of a glycosyl donor and a non-participating substituent at the 2-position of such glycosyl donor comprising contacting an acceptor with a glycosyl donor having (i) a non-participating substituent at the 2-position, (ii) a cyclic structure comprising the glycosidic carbons of either the 3- and 4-positions of the glycosyl donor and one or more substituents or the 4- and 6-positions of the glycosyl donor and one or more substituents, and (iii) a leaving group at the 1-position. In particular, embodiments of the invention the leaving group comprises a sulfoxide group, preferably an activated sulfoxide group and the non-participating substituent at the 2-position comprises a 2-alpha substituent. Moreover, the preferred stereochemical outcome provides a glycosidic linkage that defines the alpha anomer.

These and other objectives of the present invention, will be apparent to those of ordinary skill on consideration of the disclosure provided herein, particularly the following detailed description of the preferred embodiments.

4. DEFINITIONS

For the purposes of this disclosure, the following terms are defined as follows:

A monosaccharide refers to a pentose, hexose, heptose, or octose sugar, analog, or derivative thereof, including, but not limited to, deoxy sugars, dideoxy sugars, amino sugars and sugar acids. These terms include the protected and unprotected forms thereof (that is, in which selected reactive groups, typically oxygen- or nitrogen-bearing groups, of the carbohydrate monomer or monosaccharide have been either temporarily blocked to prevent their undergoing a reaction under the conditions of a specific transformation or left exposed and available for possible participation in a reaction, respectively).

Thus, a protecting group is any chemical moiety that is temporarily attached to a reactive functional group of a given molecule to mask the functional groups's reactivity while chemical reactions are permitted to proceed elsewhere on the molecule. Protecting groups preferred for protecting the reactive functional groups of sugars include, but are not limited to, alkyl, benzyl, acyl and silyl protecting groups. Many other s are well known to those of ordinary skill.

A carbohydrate monomer is a type of monosaccharide which is capable of influencing the stereochemical course of a glycosylation reaction such that the resulting glycosylation product bears substantially the stereochemistry desired (e.g., a 1,2-cis relationship among the substituents on the 1- and 2-positions of the glycosidic ring). A carbohydrate monomer is particular type of glycosyl donor, as defined below.

A carbohydrate, disaccharide, oligosaccharide, or polysaccharide each refers to a molecule or a portion thereof, which is comprised of two or more monosaccharides that are joined by a glycosidic linkage. A sugar is any carbohydrate, disaccharide, oligosaccharide, polysaccharide, or monosaccharide.

The term carbohydrate-based ligand refers to a substance having an affinity for a given receptor, such as a carbohydrate-binding protein or an enzyme, and is composed solely or partially of carbohydrate moieties. The term carbohydrate ligand may be used interchangeably with carbohydrate-based ligand in this disclosure.

A low-affinity ligand is one that, in solution, binds to a receptor with a dissociation constant of from about one hundred micromolar to about one hundred millimolar.

A glycoconjugate refers to any molecule, substance, or substrate, including a solid, that includes a monosaccharide, carbohydrate, disaccharide, oligosaccharide, or polysaccharide covalently attached or adhered to a non-sugar chemical, biochemical, biological, or inorganic moiety. Preferred glycoconjugates include, but are not limited to, small molecules conjugated to the sugar (e.g., heteropolyaromatic-sugar conjugates, nucleosides, nucleoside analogs and the like), glycopeptide, glycoproteins and the like.

A glycosyl donor is a sugar with a leaving group (or potential leaving group) on at least one of its anomeric carbon which, under appropriate conditions, is capable of participating in a glycosylation reaction by which such anomeric carbon becomes covalently attached to a second moiety, typically a glycosyl acceptor, as defined below, or a nucleophile.

A glycosyl acceptor is any moiety, including a sugar, having the capacity to participate as the second moiety in the above-mentioned glycosylation reaction by virtue of a nucleophilic (or potentially nucleophilic) group present among the groups or substituents of such moiety, such that a covalent bond is formed between the anomeric carbon of such glycosyl donor and such nucleophilic (or potentially nucleophilic) group.

The phrase "sulfoxide-mediated glycosylation reaction" refers to the glycosylation technique first described by Kahne et al. in *J. Am. Chem. Soc.* (1989) 111:6881.

The terms "lower alkyl," "lower alkoxy," "lower acyloxy," or "lower alkenyl" refer to such substituents, as the case may be, having one to five carbon atoms, in either a linear or branched arrangement. The term "aryl" refers to aromatic groups, such as phenyl rings, naphthyl rings and the like, optionally bearing one or more substituents on the various ring positions. The term "heterocycle" refers to five-membered or six-membered aromatic rings containing one or more nitrogen, oxygen, or sulfur atoms, optionally bearing one or more substituents on the various ring positions. Such optional "substituents" may be any substituent that is chemically compatible with the aryl or heterocyclic ring and with the overall molecule of which such aryl or heterocyclic ring may be a part. Various aryl and heterocyclic rings may also be referred to herein as "substituted or unsubstituted" phenyl, naphthyl and the like to designate whether or not an optional substituent is present, respectively.

A multivalent support is any material or macromolecule to which more than one carbohydrate ligand can be attached, and includes, but is not limited to, organic dendrimers and polymers, glasses, metals and metal oxides, in any physical form such as solutions, emulsions, suspensions, beads, fibers, or planar surfaces.

The detection of a substance refers to the qualitative determination that the substance is present and may also refer to the quantitative measurement of the amount of the substance present. Detection may be by any means, including but not limited to affinity-based, physical, optical, radiometric, photometric, electrochemical, or spectroscopic methods. All such detection methods are intended to be within the scope of the present invention. There are a variety of detection methods known in the art, and it is well within the capacity of the skilled practitioner to choose the method most appropriate or convenient for each situation.

The selection of a particular ligand-probe interaction refers to the process of selectively recognizing the interaction of interest from among a potentially large number of possible interactions. The selection step includes, but is not limited to, the detection of the desired interaction. For instance, selection may include the selective resolution of one or a few beads from a vessel filled with different beads or one or two wells from a multi-well plate.

A detectable moiety is any particle, molecule, fragment of a molecule, or atom whose presence and concentration can be readily measured, preferably by automated analytical instruments. The detectable moieties include, but are not limited to, radioactive isotopes, fluorescent molecules, chemiluminescent compounds, chromophores, high-affinity ligands or antigens, haptens, colloidal metal, enzymes, or other species or catalysts that can either produce or be manipulated to provide detectable products.

5. BRIEF DESCRIPTION OF THE FIGURES

6. DETAILED DESCRIPTION OF THE PREFERRED EMBODIMENTS

Figure 1:
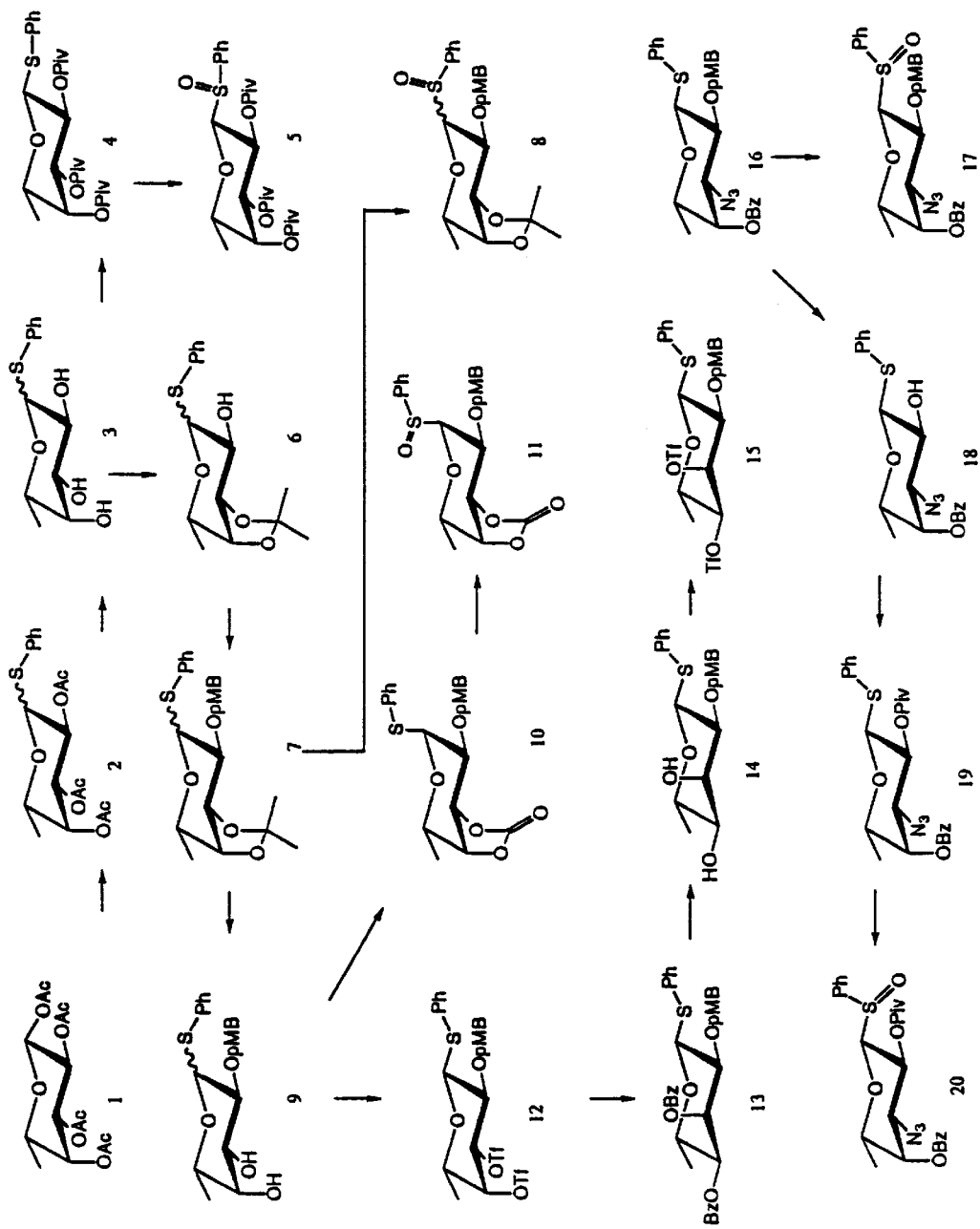
FIG. 1 illustrates the synthetic scheme for the preparation of compounds 1–20.
Figure 2:
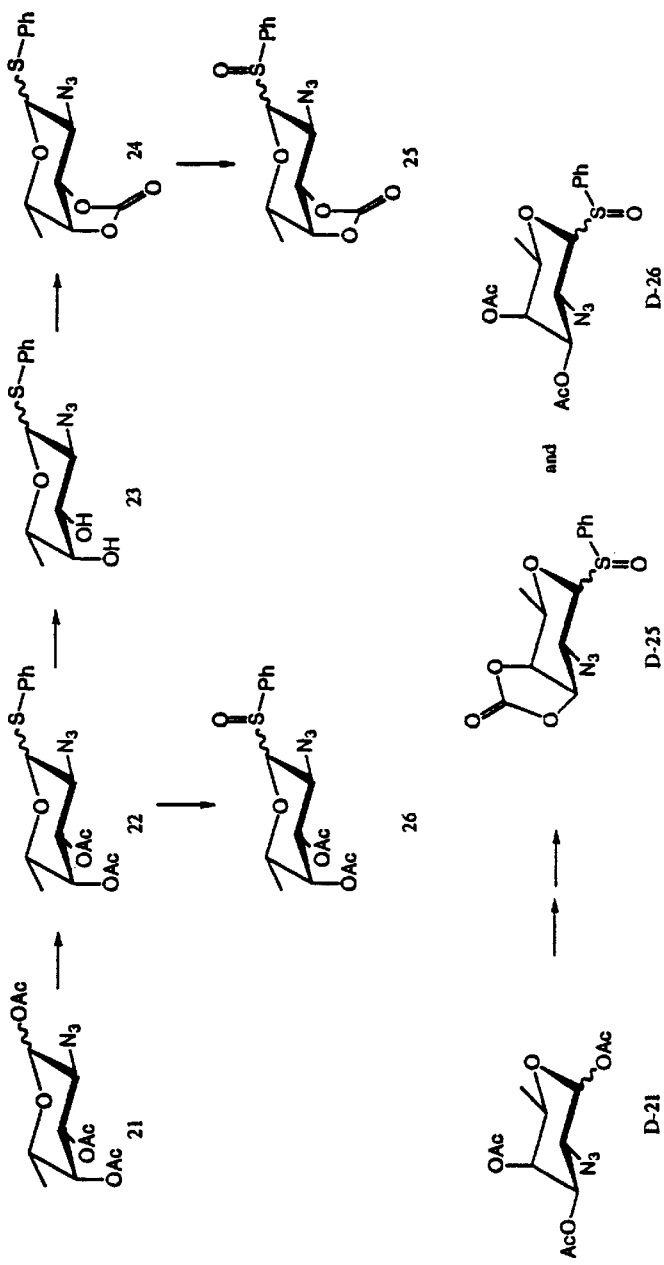
FIG. 2 illustrates the synthetic scheme for the preparation of compounds 21–D–26.
Figure 3:
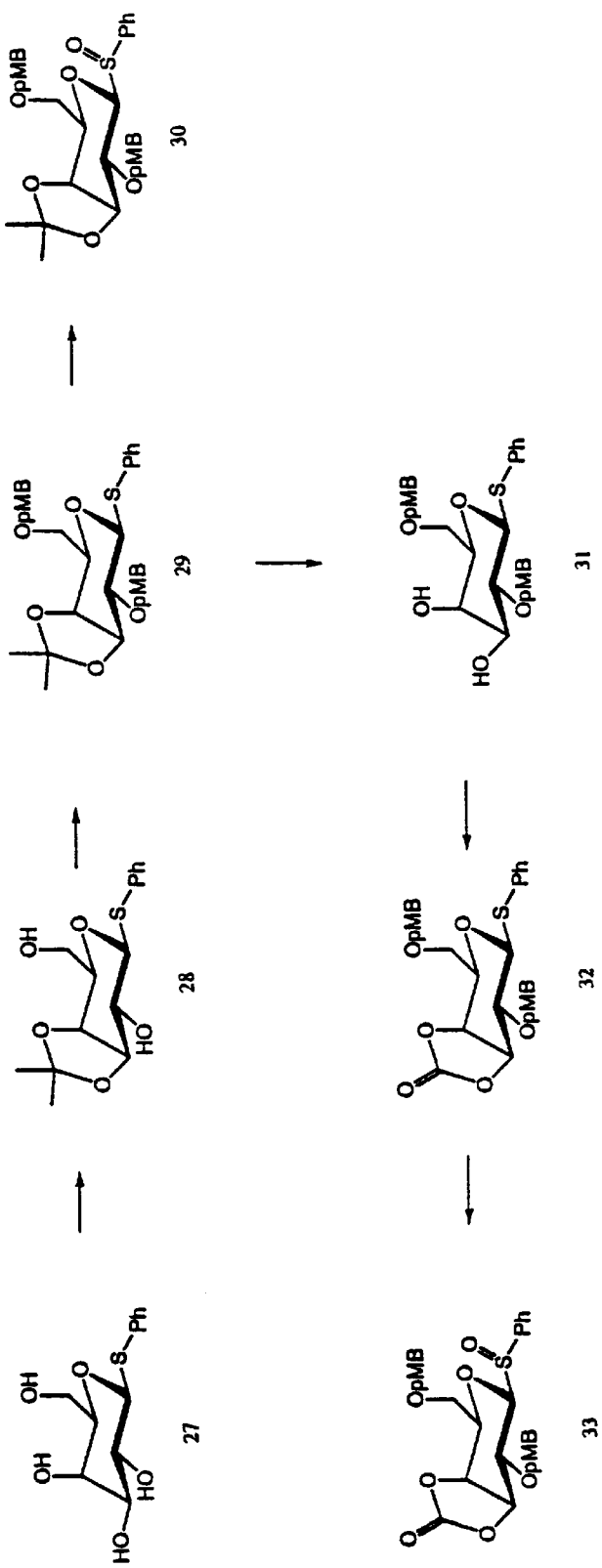
FIG. 3 illustrates the synthetic scheme for the preparation of compounds 27–33.
Figure 4:
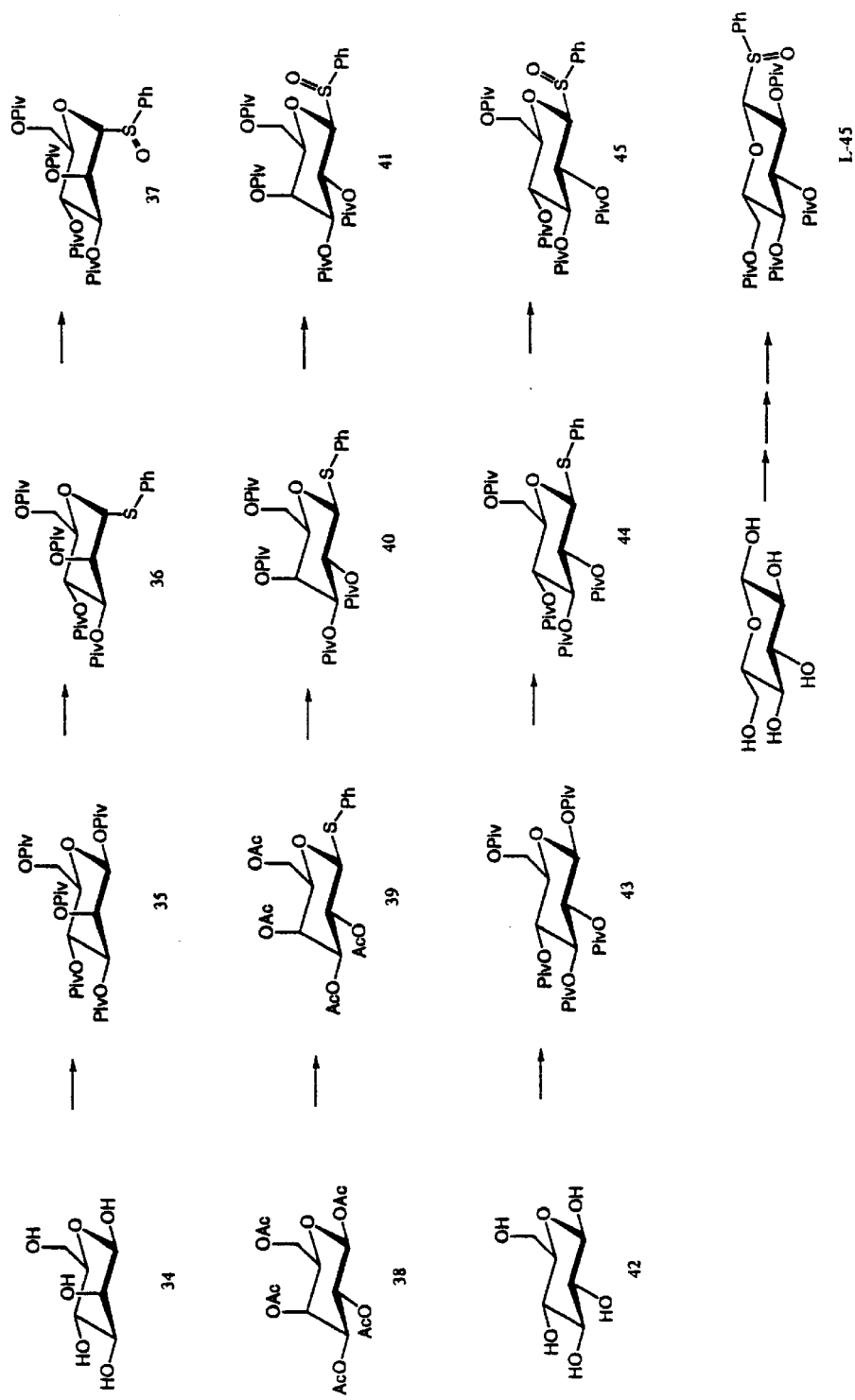
FIG. 4 illustrates the synthetic scheme for the preparation of compounds 34–L–45.
Figure 5:
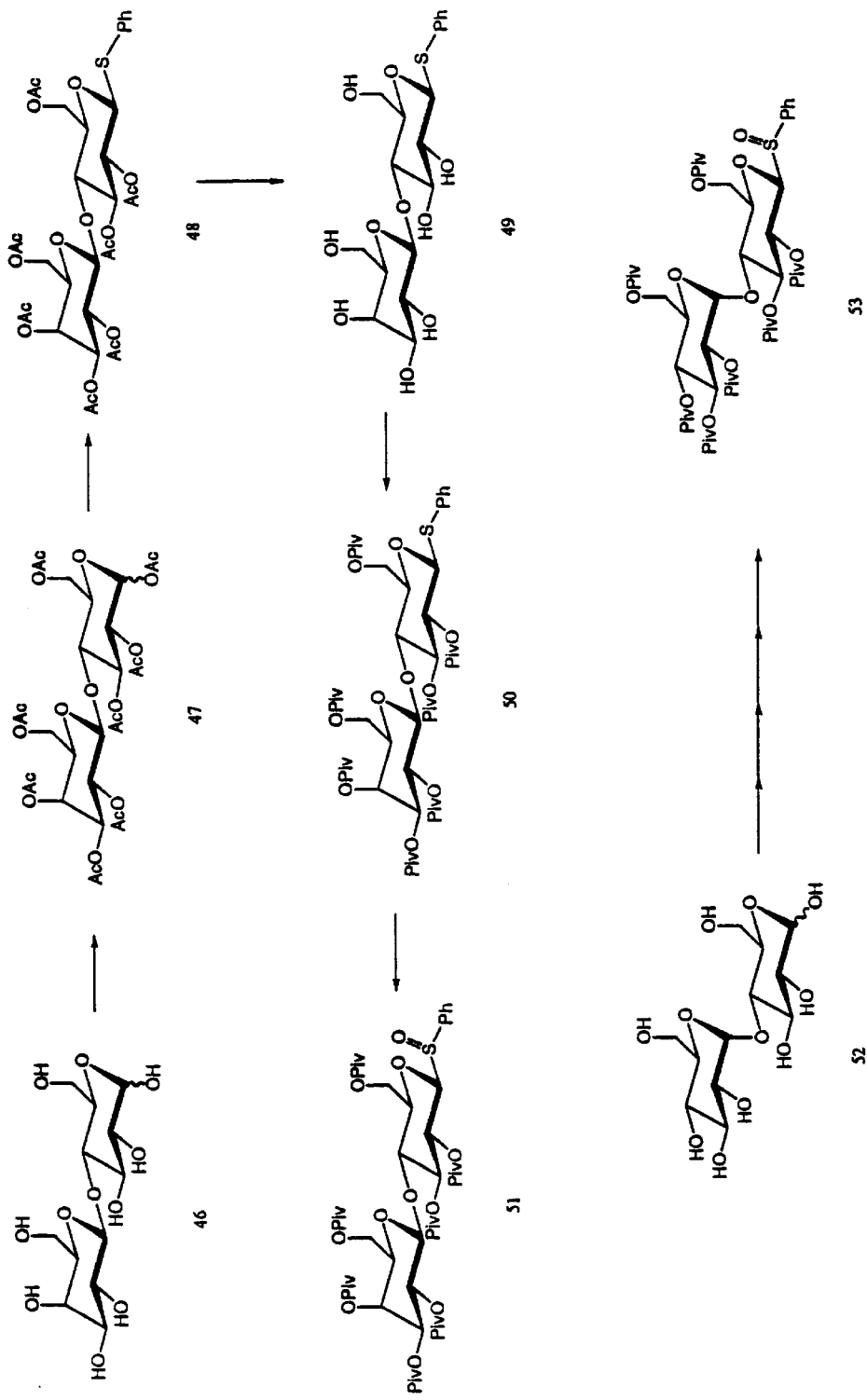
FIG. 5 illustrates the synthetic scheme for the preparation of compounds 46–53.
Figure 6:
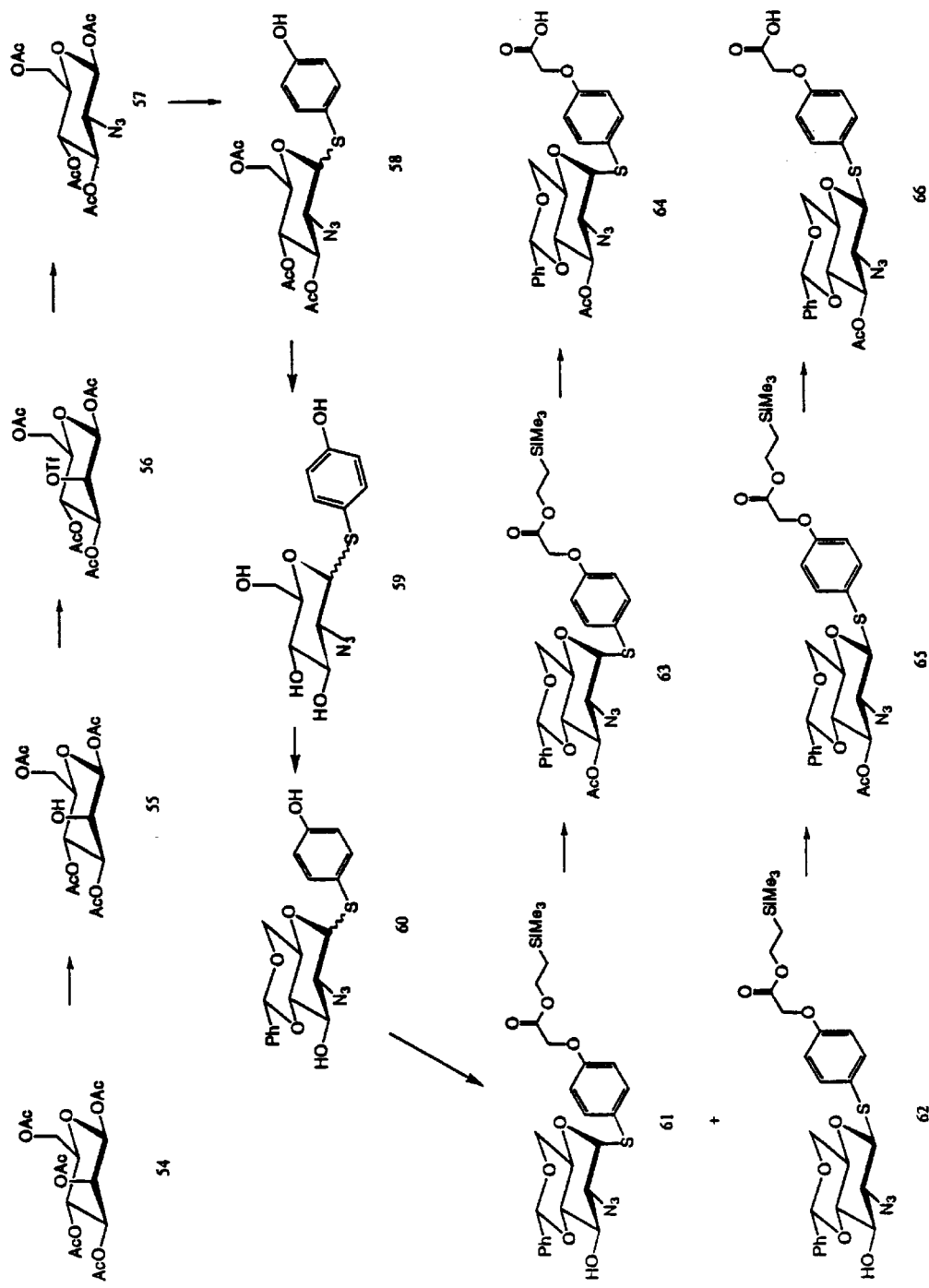
FIG. 6 illustrates the synthetic scheme for the preparation of compounds 54–66.
Figure 7:
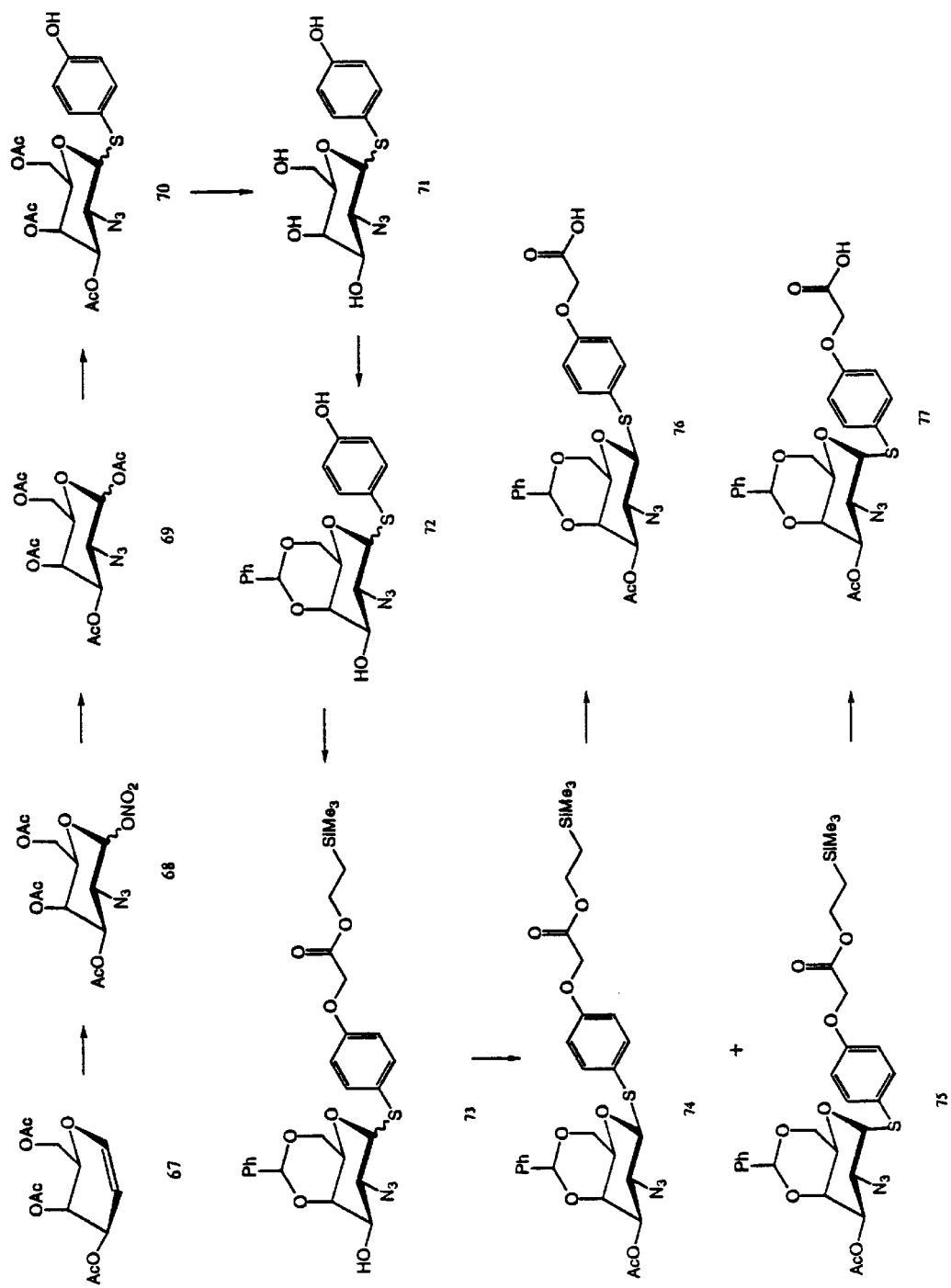
FIG. 7 illustrates the synthetic scheme for the preparation of compounds 67–77.
Figure 8:
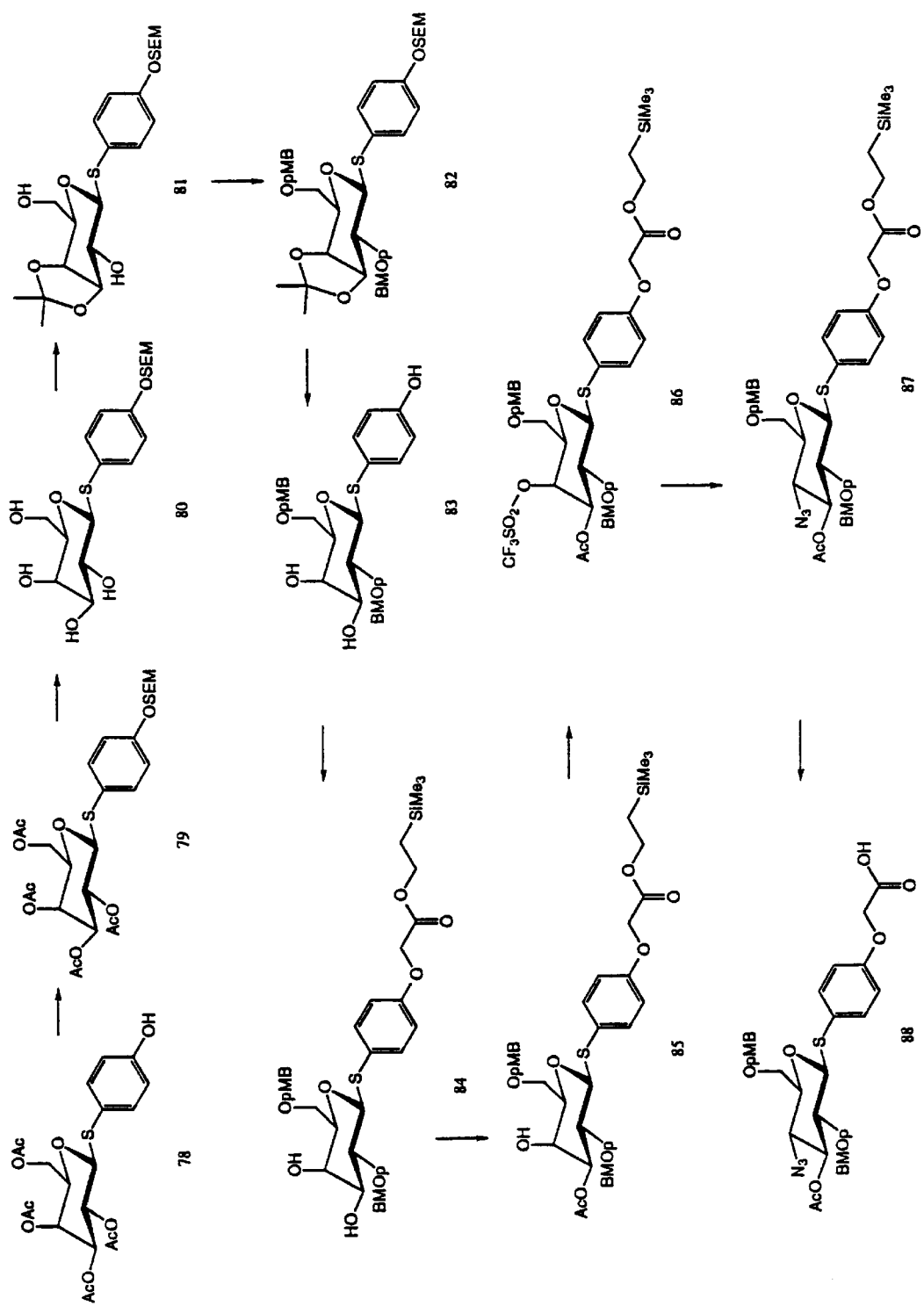
FIG. 8 illustrates the synthetic scheme for the preparation of compounds 78–88.
Figure 9:
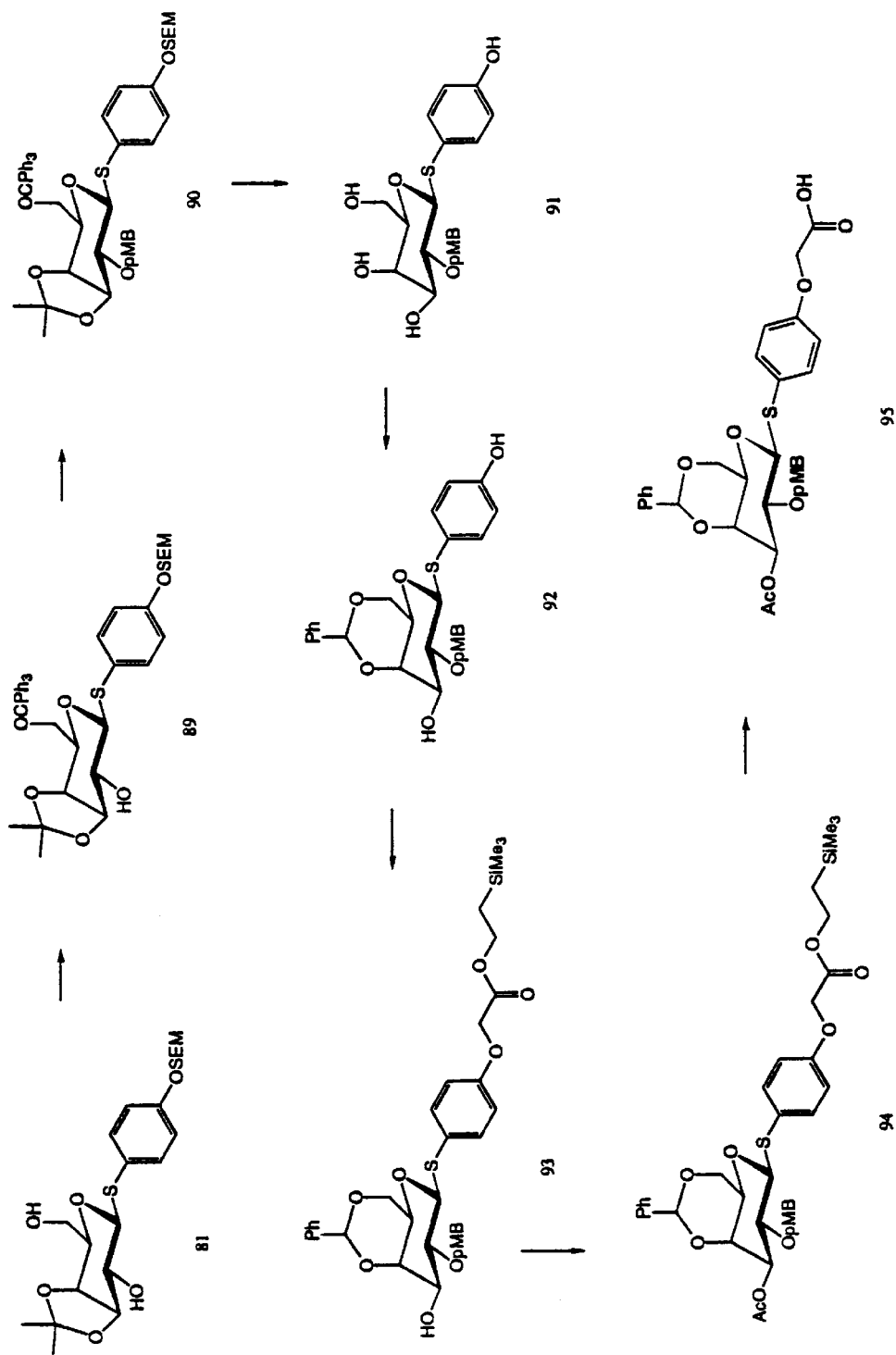
FIG. 9 illustrates the synthetic scheme for the preparation of compounds 81–95.
Figure 10:
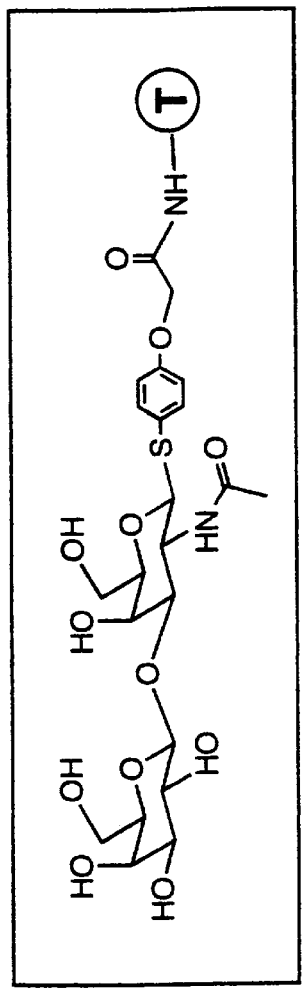
FIG. 10 illustrates, in a particular embodiment, the building blocks that may make up a resin-bound glycoside (depicted in the box). Using the particular hexose derivatives described herein as part of the available building blocks, one can prepare libraries having preferred stereochemistries.
Figure 10:
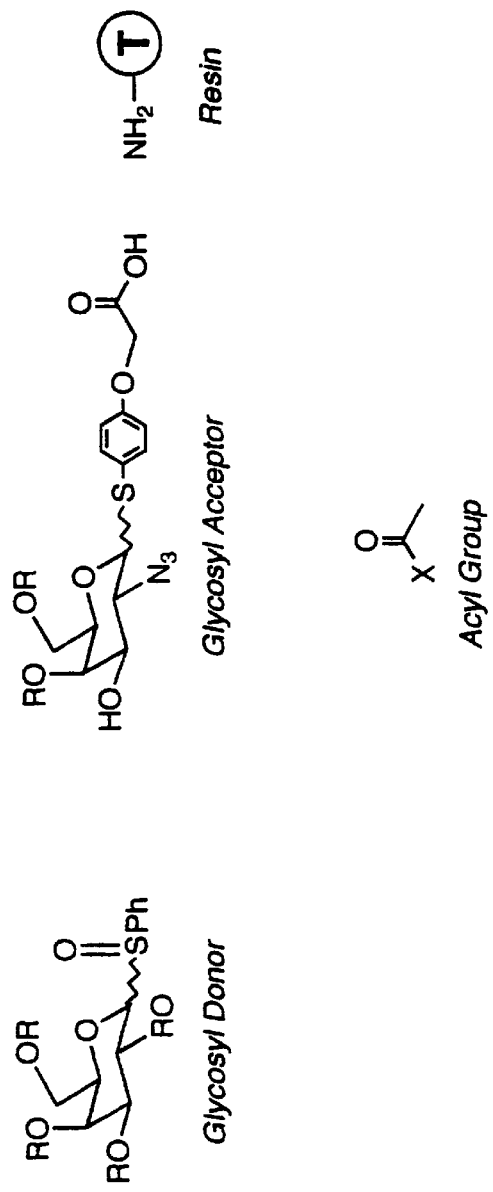

The invention in its broadest aspect provides a selection of protected 1-deoxy-1-(arylsulfinyl) hexose derivatives (glycosyl donors) of structures 1, 2, and 3 that are suitable for use in preparing glycosides with high stereoselectivity and in high yield. The compounds of the invention are especially suitable for the synthesis of glycosides and glycoside libraries on soluble polymeric supports, insoluble polymeric supports, and other solid-phase supports. Representative glycosides, one a donor and the other a potentially resin-bound acceptor, are depicted in FIG. 10. Combining the various components give rise to a potential carbohydrate ligand bound to a solid phase support.

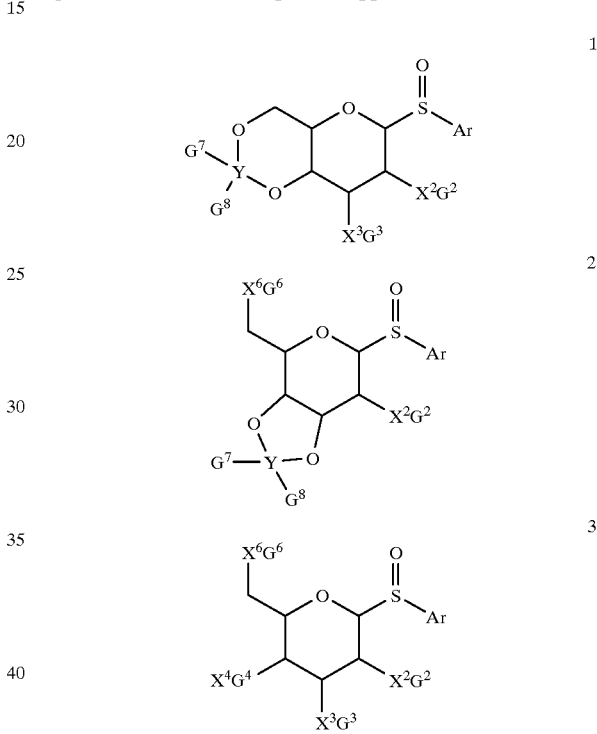

In the structures 1, 2, and 3, the groups $X^2$ through $X^6$ may be oxygen, and where X is oxygen the attached groups $G^2$ through $G^6$ may be:

C1 to C8 branched or unbranched alkyl or alkenyl (optionally substituted by one or more lower alkoxy, lower acyloxy, halogen, or aryl);

C1 to C8 branched or unbranched acyl (optionally substituted by one or more lower alkoxy, lower acyloxy, halogen, or aryl);

benzoyl, optionally substituted by one or more lower alkyl, lower alkoxy, lower acyloxy, halogen, nitro, or aryl;

lower alkoxycarbonyl, optionally substituted by one or more lower alkenyl, lower alkoxy, lower acyloxy, halogen, aryl, or 9-fluorenyl; or silicon, substituted by one or more lower alkyl, lower alkoxy, or aryl.

The groups $X^2$ through $X^6$ may each independently be nitrogen, and where X is nitrogen the attached group G may be:

C1 to C8 branched or unbranched acyl (optionally substituted by one or more lower alkoxy, lower acyloxy, halogen, or aryl);

benzoyl, optionally substituted by one or more lower alkyl, lower alkoxy, lower acyloxy, halogen, nitro, or aryl; or lower alkoxycarbonyl, optionally substituted by one or more lower alkenyl, lower alkoxy, lower acyloxy, halogen, aryl, or 9-fluorenyl.

The groups $X^2$ through $X^6$ may further each independently be azido or hydrogen, and where X is azido or hydrogen the attached group G is not present.

The atom Y may be carbon, in which case the groups $G^7$ and $G^8$ are independently branched or unbranched lower alkyl, aryl, or hydrogen, or taken together $G^7$ and $G^8$ are a carbonyl oxygen doubly bonded to Y. The atom Y may also be silicon, in which case the groups $G^7$ and $G^8$ are independently branched or unbranched lower alkyl, lower alkoxy, or aryl.

The group Ar may be phenyl, naphthyl, or a heterocycle, all of which may be optionally substituted. For examples of the preparation and utility of substituted 1-(phenylsulfenyl) hexose derivatives, see L. Sliedregt, G. van der Marel, J. van Boom, Tetrahedron Lett., 35, 4015–4018 (1994). Ar is preferably phenyl, 4-nitrophenyl, or 4-methoxyphenyl, and is most preferably phenyl.

The preferred structures are 1 and 2, most preferably 2. Where $X^2$ is oxygen, $G^2$ is preferably C1 to C8 branched or unbranched alkyl or alkenyl (optionally substituted by one or more lower alkoxy, lower acyloxy, halogen, or aryl); or C1 to C8 branched or unbranched acyl (optionally substituted by one or more lower alkoxy, lower acyloxy, halogen, or aryl). Where $X^2$ is oxygen, $G^2$ is most preferably tertiary alkyl, pivaloyl, or C1 to C3 alkyl substituted with one or more aryl. Where any of $X^3$ through $X^6$ are oxygen, the attached groups $G^3$ through G6 are preferably chosen from among the following: acetyl, pivaloyl, 2-methoxyethyl, 2-(methoxy)ethoxymethyl, benzyl, 4-methoxybenzyl, and trimethylsilyl. Where Y is carbon, the groups $G^7$ and $G^8$ preferably together form a carbonyl oxygen.

Most specifically, the invention provides derivatives of D- and L-galactose, D- and L-mannose, and D- and L-allose, and the 6-deoxy derivatives thereof, which are suitable for the above applications.

It will be evident to those skilled in the art that the sulfur atom in the compounds of the invention is a chiral center, and that it may exist in mirror-image configurations. This gives rise to diastereomeric mixtures of sulfoxides, given the chirality at C-1 of the hexoses; these diastereomers may be separable by standard chromatographic methods or by enzymatic methods (O. Karthaus, S. Shoda, S. Kobayashi, Tetrahedron: Asymmetry 5 (11) 2213–2216 (1994). The compounds of the invention may also exist as alpha- or beta-anomers at the anomeric (C-1) carbon, hence four diastereomers of each illustrated structure are possible. All four diastereomers, and mixtures thereof, are of approximately equal utility for the preparation of glycosides. All four diastereomers, individually and as mixtures, are thus contemplated by the present invention. Furthermore, it will be evident to those skilled in the art that these hexose derivatives can be synthesized to generate glycosidic libraries, initially bound but cleavable from polymeric supports, as depicted in FIG. 10.

7. EXAMPLES

The scope of the present invention is not limited in any way by the scope of the examples provided below, which are presented for illustrative purposes only.

7.1. Preparation of 1,6-Dideoxy-2,3,4-tri-O-pivaloyl-1-(phenylsulfinyl)-β-L-galactopyranose (5)

To a solution of L-fucose (1.03 g, 6.09 mmol) in 60 mL of pyridine at room temperature is added acetic anhydride (4.6 mL, 4.96 g, 48.7 mmol). The solution is stirred at room temperature for 20 h and concentrated in vacuo. The residue is then dissolved in 50 mL of $CH_2Cl_2$ and washed with 5% HCl (4×60 mL), dried over anhydrous $Na_2SO_4$ and concentrated to afford 1.76 g (85%) of L-fucose tetraacetate 1 as a white foam, a 5:2 (α:β) mixture of anomers: $R_f$ 0.38 (40% petroleum ether/EtOAc); $^1$H NMR ($CDCl_3$, 270 MHz, mixture of anomers) δ 6.33 (d, J=2.0 Hz, 1H, H-1α), 5.67 (d, J=8.2 Hz, 1H, H-1β), 5.26–5.38 (m, 5H), 5.06 (dd, J=10.4, 3.4 Hz, 1H, H-3b), 4.27 (q, J=6.6 Hz, 1H, H-5α), 3.95 (q, J=6.3 Hz, 1H, H-5β), 2.23 (s, 3H), 2.19 (s, 3H), 2.18 (s, 3H), 2.17 (s, 3H), 2.15 (s, 3H), 2.04 (s, 3H), 2.02 (s, 3H), 2.01 (s, 3H), 1.22 (d, J=6.6 Hz, 3H, H-6β), 1.16 (d, J=6.6 Hz, 3H, H-6α).

To a solution of L-fucose tetraacetate 1 (1.76 g, 5.30 mmol) in 50 mL of $CH_2Cl_2$ is added thiophenol (1.4 mL, 1.46 g, 13.2 mmol) followed by $BF_3OEt_2$ (3.3 mL, 3.76 g, 26.5 mmol). The reaction mixture is stirred at room temperature for 17 h and then quenched by the addition of 5 mL of $H_2O$. The reaction mixture is diluted with 200 mL of $CH_2Cl_2$, washed with $H_2O$ (100 mL), saturated NaCl (100 mL), dried over $Na_2SO_4$, filtered and concentrated to afford 2.77 g of a clear oil, which is purified by flash chromatography (17% EtOAc/petroleum ether) to give 1.36 g (67%) of phenyl 6-deoxy-2,3,4-tri-O-acetyl-1-thio-L-galactopyranoside 2 as a 3.5:1 (β:α) mixture of anomers. The anomers could be separated by flash chromatography (17% EtOAc/petroleum ether): $R_f$ (β-anomer) 0.19 (17% EtOAc/petroleum ether); $R_f$ (α-anomer) 0.26 (17% EtOAc/petroleum ether); $^1$H NMR ($CDCl_3$, 300 MHz) β-anomer, δ 7.41–7.55 (m, 2H), 7.22–7.37 (m, 3H), 5.20–5.30 (m, 2H), 5.05 (dd, J=9.9, 3.3 Hz, 1H, H-3), 4.70 (d, J=9.9 Hz, 1H, H-1), 3.84 (q, J=6.4 Hz, 1H, H5), 2.15 (s, 3H), 2.09 (s, 3H), 1.98 (s, 3H), 1.24 (d, J=6.6 Hz, 3H, H-6); α-anomer, δ 7.48–7.53 (m, 2H), 7.16–7.45 (m, 3H), 5.93 (d, J=5.1 Hz, 1H, H-1), 5.27–5.41 (m, 3H), 4.61 (q, J=6.6 Hz, 1H, H-5), 2.17 (s, 3H), 2.11 (s, 3H), 2.02 (s, 3H), 1.13 (d, J=6.6 Hz, 3H, H-6).

To a solution of phenyl 6-deoxy-2,3,4-tri-O-acetyl-1-thio-β-L-galactopyranoside 2 (0.892 g, 2.33 mmol) in 25 mL of methanol is added $K_2CO_3$ (0.644 g, 4.66 mmol). The reaction mixture is stirred at room temperature for 12 h. Amberlite resin ($H^+$ form) is added to the reaction mixture and stirred for an additional 30 min. The neutralized mixture is then filtered through Celite, which is washed several times with methanol, and the filtrate is concentrated to afford 1.39 g of phenyl 6-deoxy-1-thio-β-L-galactopyranoside 3 as a yellow oil, which is used in the next step without further purification. The thioglycoside 3 can be purified using flash chromatography (10% MeOH/$CH_2Cl_2$): $R_f$ 0.28 (10% MeOH/$CH_2Cl_2$); $^1$H NMR ($C_6D_6$, 270 MHz) δ 7.54–7.58 (m, 2H) 7.28–7.37 (m, 3H), 4.50 (d, J=8.2 Hz, 1H, H-1), 3.70 (q, J=6.6 Hz, 1H, H-5), 3.56–3.75 (m, 3H), 1.38 (d, J=6.6 Hz, 3H).

To a solution of crude phenyl 6-deoxy-1-thio-β-L-galactopyranoside 3 in 15 mL of pyridine is added pivaloyl chloride (4.0 mL, 3.90 g, 32.5 mmol) and DMAP (0.33 g, 2.71 mmol). The reaction mixture is heated at 100° C. for 12 h, cooled, diluted with 50 mL of $CH_2Cl_2$, washed with $H_2O$ (100 mL) and saturated NaCl (100 mL), dried over $Na_2SO_4$, filtered and concentrated to afford 3.25 g of phenyl 6-deoxy-2,3,4-tri-O-pivaloyl-1-thio-β-L-galactopyranoside 4 as a brown oil. This oil is purified by flash chromatography (15% EtOAc/petroleum ether) to afford 0.53 g (48%) of the pure compound. An additional 0.81 g of a brown oil, which that appeared to be a mixture of incompletely acylated products, is also isolated. This material is resubjected to the reaction conditions for 48 h and provided an additional 0.21 g (19%, total yield 67% for 2 steps): $R_f$ 0.48 (15% EtOAc/petroleum ether); $^1$H NMR (CDCl$_3$, 270 MHz) δ 7.50–7.59 (m, 2H), 7.23–7.35 (m, 3H), 5.16–5.30 (m, 2H), 5.08 (dd, J=9.9, 3.0 Hz, 1H, H-3), 4.66 (d, J=9.6 Hz, 1H, H-1), 3.90 (q, J=6.3 Hz, 1H, H-5), 1.21 (s, 9H), 1.18 (s, 9H), 1.21 (s, 9H), 1.21 (d, J=6.6 Hz, 3H, H-6); $^{13}$C NMR (CDCl$_3$, 68 MHz) δ 177.2, 177.4, 177.1, 133.5, 131.1, 128.6, 128.4, 128.1, 127.7, 85.1, 73.3, 72.6, 69.9, 66.3, 38.9, 38.6, 26.9, 27.0, 16.4; FABMS C$_{27}$H$_{39}$O$_7$S (MNa$^+$) calcd 531.2392, found 531.2404.

To a solution of phenyl 6-deoxy-2,3,4-tri-O-pivaloyl-1-thio-β-L-galactopyranoside 4 (2.47 g, 5.22 mmol) in 65 mL of CH$_2$Cl$_2$ at –78° C. is added mCPBA (1.53 g, 8.84 mmol). The reaction mixture is allowed to warm to –15° C. and then quenched with methyl sulfide (5.3 mL, 4.48 g, 17.4 mmol) and allowed to warm to room temperature. The reaction mixture is then diluted with 50 mL CH$_2$Cl$_2$, extracted with H$_2$O (100 mL), saturated NaHCO$_3$ (100 mL), saturated NaCl (100 mL), dried over Na$_2$SO$_4$, filtered and concentrated to afford a white solid. The sulfoxide is purified using flash chromatography (15% EtOAc/petroleum ether) to afford 1.81 g (66%) of 1,6-dideoxy-2,3,4-tri-O-pivaloyl-1-(phenylsulfinyl)-β-L-galactopyranose 5 as a mixture of diastereomers: $R_f$ 0.05 and 0.13 (15% EtOAc/petroleum ether).

7.2. 1,6-Dideoxy-1-(phenylsulfinyl)-2,3,4-tri-O-pivaloyl-β-D-galactopyranose (β-D-5)

By the above method, but beginning with D-fucose, the title compound is prepared.

7.3. 3-Azido-4-O-benzoyl-1,3,6-trideoxy-2-O-pivaloyl-1-(phenylsulfinyl)-β-L-galactopyranose (20)

To a solution of L-fucose phenylthioglycoside (phenyl 6-deoxy-1-thio-L-galactopyranoside, 3, prepared above) (3.4 g, 13 mmol) in 250 mL of DMF is added p-toluenesulfonic acid hydrate (1.3 g, 6.6 mmol) and 2,2-dimethoxypropane (3.3 mL, 27 mmol). The reaction mixture is stirred at room temperature for 12 h and then quenched by the addition of 10 mL of saturated NaHCO$_3$. The reaction mixture is diluted with 400 mL of CH$_2$Cl$_2$, washed with saturated NaHCO$_3$ (2×200 mL), dried over Na$_2$SO$_4$, filtered, concentrated and purified by flash chromatography (8% EtOAc/petroleum ether) to give 3.3 g (85%) of phenyl 6-deoxy-3,4-O-isopropylidene-1-thio-L-galactopyranoside 6 as a mixture of anomers. The anomers could be separated by flash chromatography: $R_f$ (α-6) 0.58 (50% EtOAc/petroleum ether); $R_f$ (β-anomer) 0.46 (50% EtOAc/petroleum ether); $^1$H NMR of β-6 (CDCl$_3$, 300 MHz) δ 7.70–7.55 (m, 2H), 7.45–7.28 (m, 3H, ArH), 4.48 (d, J=10 Hz, 1H, H-1), 4.15–4.10 (m, 2H, H-3 and H4), 3.96 (q, J=4.8 Hz, 1H, H-5), 3.62 (q, J=4.0 Hz, 1H, H-2), 2.52 (s, br, 1H, OH), 1.53–1.50 (m, 6H, H-6 and CH$_3$), 1.42 (s, 3H, CH$_3$).

To a solution of phenyl 6-deoxy-3,4-O-isopropylidene-1-thio-L-galactopyranoside 6 mixed anomers (2.12 g, 7.16 mmol) in 140 mL of DMF is added NaH (568 mg, 14.2 mmol), and the reaction mixture stirred for 10 min. p-Methoxybenzyl chloride (1.9 mL, 14.2 mmol) is added, and the solution is stirred for 30 min and then quenched with 10 mL of saturated NaHCO$_3$. The reaction mixture is diluted with 300 mL of CH$_2$Cl$_2$, washed with saturated NaHCO$_3$ (150 mL), dried over Na$_2$SO$_4$, filtered and concentrated. The crude product is purified by flash chromatography (8% EtOAc/petroleum ether) to give 2.6 g (87%) of phenyl 6-deoxy-3,4-O-isopropylidene-2-(4-methoxybenzyl)-1-thio-L-galactopyranoside 7 as a mixture of anomers: $R_f$ 0.50 (35% EtOAc/petroleum ether); $^1$H NMR of β-7 (CDCl$_3$, 300 MHz) δ 7.60 (d, 2H, ArH), 7.43–7.28 (m, 5H, ArH), 6.94 (d, 2H, ArH), 4.82 (d, J=10.6 Hz, 1H, CH$_2$), 4.67 (d, J=10.6 Hz, 1H, CH$_2$), 4.65 (d, J=9.9 Hz, 1H, H-1), 4.29 (t, J=5.9 Hz, 1H, H-2), 4.13 (dd, J=5.9, 2.2 Hz, 1H, H-3), 3.91–3.86 (m, 4H, H-4, OCH$_3$), 3.56 (dd, J=6.2, 3.3 Hz, 1H, H-5), 1.50 (s, 3H, CH$_3$), 1.47 (d, J=6.2 Hz,3H, H-6) 1.44 (s, 3H, CH$_3$).

To a solution of phenyl 6-deoxy-3,4-O-isopropylidene-2-(4-methoxybenzyl)-1-thio-L-galactopyranoside 7 mixed anomers (2.4 g, 5.8 mmol) in 60 mL of MeOH is added TsOH.H$_2$O (540 mg, 2.9 mmol). The reaction mixture is stirred at room temperature for 5 h and then neutralized with Amberlite resin (OH$^-$ form). The solution is filtered, washed several times with MeOH and then concentrated in vacuo. The product is purified by flash chromatography (60% EtOAc/petroleum ether) to give 2.06 g (95%) of isolated anomers of phenyl 6-deoxy-2-(4-methoxybenzyl)-1-thio-L-galactopyranoside 9. $^1$H NMR (CDCl$_3$, 300 MHz) of β-9: δ 7.65 (d, 2H, ArH), 7.40–7.37 (m, 5H, ArH), 6.96 (d, 2H, ArH), 4.95 (d, J=10.6 Hz, 1H, CH$_2$), 4.69 (d, J=10.6 Hz, 1H, CH$_2$), 4.67 (d, J=9.5 Hz, 1H, H-1), 3.87 (s, 3H, OCH$_3$), 3.79 (d, J=2.9 Hz, 1H, H-4), 3.72–3.58 (m, 3H, H-2, H-3, H-5), 2.46 (s, br, 2H, OH), 1.42 (d, J=6.2 Hz, 3H, H-6); α-9, δ7.56 (d, 2H, ArH), 7.43–7.31 (m, 5H, ArH), 6.95 (d, 2H, ArH), 5.78 (d, J=5.7 Hz, 1H, H-1), 4.78 (d, J=11.5 Hz, 1H, CH$_2$), 4.58 (d, J=11.5 Hz, 1H, CH$_2$), 4.50 (q, J=6.4 Hz, 1H, H-5), 4.12 (dd, J=5.7, 9.6 Hz, 1H, H-3), 3.97–3.82 (m, 5H, H-2, H-4, OCH$_3$), 3.18 (s, br, 1H, OH), 2.88 (s, br, 1H, OH), 1.40 (d, J=6.4 Hz, 3H, H-6)

Trifluoromethanesulfonic anhydride (2.5 mL, 15 mmol) is added dropwise to a cooled (0° C.) solution of phenyl 6-deoxy-2-(4-methoxybenzyl)-1-thio-β-L-galactopyranoside (β-9) (1.4 g, 3.8 mmol) and pyridine (3.0 mL, 38 mmol) in 50 mL of CH$_2$Cl$_2$. The solution is stirred at 0° C. for 45 min and is allowed to warm to room temperature over 3 h. The reaction mixture is then cooled to 0° C. before quenching with TEA (1 mL, 7.2 mmol). The reaction mixture is diluted with 25 mL of CH$_2$C$_2$, extracted with saturated NaHCO$_3$ (2×50 mL), dried over Na$_2$SO$_4$, filtered, concentrated and purified by flash chromatography (8% EtOAc/petroleum ether) to give phenyl 6-deoxy-3,4-di-O-trifluoromethanesulfonyl-2-(4-methoxybenzyl)-1-thio-β-L-galactopyranoside (β-12): $R_f$ 0.44 (20% EtOAc/petroleum ether); $^1$H NMR (CDCl$_3$, 270 MHz) δ 7.60–7.57 (m, 2H, ArH), 7.38–7.33 (m, 5H, ArH), 6.90 (d, 2H, ArH), 5.16 (d, J=2.3 Hz, 1H, H-4) 4.92 (dd, J=2.3, 9.6 Hz, 1H, H-3), 4.80 (d, J=9.2 Hz, 1H, CH$_2$), 4.65 (d, J=9.6 Hz, 1H, H-1), 4.63 (d, J=9.2 Hz, 1H, CH$_2$), 3.83–3.76 (m, 5H, H-2, H-5, OCH$_3$) 1.45 (d, J=6.6 Hz, 3H, H-6)

To a solution of the above bis(triflate) β-12 in 40 mL of toluene is added potassium benzoate (1.8 g, 11 mmol) and 18-crown-6 (3.0 g, 11 mmol). The reaction mixture is stirred at room temperature for 5 h and then diluted with 40 mL of CH$_2$Cl$_2$. The resulting solution is washed with saturated NaHCO$_3$ (2×50 mL), dried over Na$_2$SO$_4$, filtered and concentrated. The crude phenyl 6-deoxy-3,4-di-O-benzoyl-2-O-(4-methoxybenzyl)-1-thio-β-L-allopyranoside (β-13) is used without further purification in the next step. However, the material can be purified by flash chromatography (10% EtOAC/petroleum ether): $R_f$ 0.59 (20% EtOAc/petroleum ether); $^1$H NMR (CDCl$_3$, 270 MHz) δ 8.02 (d, 2H, ArH), 7.85 (d, 2H, ArH), 7.61–7.23 (m, 9H, ArH) 6.83 (d, 2H, ArH), 6.16 (t, J=3.0 Hz, 1H, H-3), 5.17 (d, J=9.6 Hz, 1H, H-1), 4.95 (dd, J=2.6, 9.9 Hz, 1H, H-4), 4.66 (d, J=10.9 Hz, 1H, CH$_2$), 4.37 (d, J=10.9 Hz, 1H, CH$_2$), 4.24 (dq, J=6.3, 9.9 Hz, 1H, H-5), 3.78 (s, 3H, OCH$_3$), 3.60 (dd, J=3.0, 9.6 Hz, 1H, H-2), 1.33 (d, J=6.3 Hz, 3H, H-6).

To a solution of crude phenyl 6-deoxy-3,4-di-O-benzoyl-2-O-(4-methoxybenzyl)-1-thio-β-L-allopyranoside β-13 in 20 mL of MeOH is added NaOMe (200 mg, 3.8 mmol). The reaction mixture is stirred at room temperature for 2 h and then neutralized with Amberlite resin. The solution is filtered, washed several times with MeOH and concentrated in vacua. The crude product is purified by flash chromatography (60% EtOAc/petroleum ether) to afford 1.01 g (72%, 3 steps) of phenyl 6-deoxy-2-O-(4-methoxybenzyl)-1-thio-β-L-allopyranoside (β-14): $R_f$0.35 (50% EtOAc/petroleum ether); $^1$H NMR (CDCl$_3$, 270 MHz) δ 7.56–7.52 (m, 2H, ArH), 7.31–7.27 (m, 5H, ArH), 6.89–6.88 (m, 2H, ArH), 4.93 (d, J=9.9 Hz, 1H, H-1), 4.71 (d, J=11.2 Hz, 1H, CH$_2$), 4.55 (d, J=11.2 Hz, 1H, CH$_2$), 4.13 (t, J=2.6 Hz, 1H, H-3), 3.83 (s, 3H, OCH$_3$), 3.73–3.63 (m, 1H, H-5), 3.38 (dd, J=3.3, 9.9 Hz, 1H, H-2), 3.21 (dt, J=3.3, 9.6 Hz, 1H, H-4), 2.58 (s, 1H, OH) 2.34–2.30 (d, 1H, OH), 1.33 (d, J=6.3 Hz, 3H, H-6).

Trifluoromethanesulfonic anhydride (1.8 mL, 10.8 mmol) is added at 0° C. to a solution of phenyl 6-deoxy-2-O-(4-methoxybenzyl)-1-thio-β-L-allopyranoside (β-14) (1.01 g, 2.69 mmol) and pyridine (2.2 mL, 26.9 mmol) in 30 mL of CH$_2$Cl$_2$. The solution is stirred at 0° C. for 1 h and allowed to warm at room temperature over 3 h. The reaction mixture is cooled to 0° C. before quenching with TEA (1.0 mL, 7.2 mmol). The reaction mixture is diluted with 30 mL of CH$_2$Cl$_2$, washed with saturated NaHCO$_3$ (30 mL), 1N HCl (30 mL), dried over Na$_2$SO$_4$, filtered and concentrated. The crude product is purified by flash chromatography (8% EtOAc/petroleum ether) to give 1.36 g (79%) of phenyl 6-deoxy-3,4-di-O-(trifluoromethanesulfonyl)-2-O-(4-methoxybenzyl)-1-thio-β-L-allopyranoside (β-15): $R_f$0.49 (20% EtOAc/petroleum ether); $^1$H NMR (CDCl$_3$, 270 MHz) δ 7.48 (d, 2H, ArH), 7.33–7.21 (m, SH, ArH), 6.91 (d, 2H, ArH), 5.34 (t, J=2.0 Hz, 1H, H-3), 4.93 (d, J=9.2 Hz, 1H, H-1), 4.77 (d, J=11.2 Hz, 1H, CH$_2$), 4.65 (d, J=11.2 Hz, 1H, CH$_2$), 4.55 (dd, J=2.0, 8.8 Hz, 1H, H-4), 4.19–3.96 (m, 1H, H-5), 3.90 (s, 3H, OCH$_3$), 3.47 (dd, J=2.0, 9.2 Hz, 1H, H-2), 1.36 (d, J=5.8 Hz, 3H, H-6).

The above bis(triflate) β-15 (297 mg, 2.13 mmol) is dissolved in 10 mL of DMF and cooled at −15° C. To the solution is added NaN$_3$ (137 mg, 2.11 mmol) and the reaction mixture is stirred at −15° C. for 45 minutes. Potassium benzoate (511 mg, 3.20 mmol) and 18-crown-6 (844 mg, 3.20 mmol) are added to the reaction mixture. The reaction mixture is stirred for 8 h and is then diluted with 20 mL of CH$_2$Cl$_2$. The resulting solution is washed with NaHCO$_3$ (3×20 mL), dried over Na$_2$SO$_4$, filtered and concentrated. The resulting phenyl 3-azido-4-O-benzoyl-3,6-dideoxy-2-O-(4-methoxybenzyl)-1-thio-β-L-galactopyranoside (β-16) is purified by flash chromatography (20% EtOAc/petroleum ether) and taken on immediately to the next step: $R_f$0.35 (20% EtOAc/petroleum ether); $^1$H NMR (CDCl$_3$, 270 MHz) δ 8.01 (d, 2H, ArH), 7.71–7.26 (m, 10H, ArH), 6.90 (d, 2H, ArH), 5.47 (d, J=2.0 Hz, 1H, H-4), 4.91 (d, J=9.6 Hz, 1H, CH$_2$), 4.69 (d, J=9.2 Hz, 1H, H-1), 4.64 (d, J=9.6 Hz, 1H, CH$_2$), 3.85–3.64 (m, 6H, H-2, H-3, H-5, OCH$_3$), 1.27 (d, J=6.3 Hz, 3H, H-6).

To a solution of phenyl 3-azido-4-O-benzoyl-3,6-dideoxy-2-O-(4-methoxybenzyl)-1-thio-β-L-galactopyranoside (β-16) in 50 mL of CH$_2$C$_2$ is added 5 mL of TFA (10% TFA/CH$_2$Cl$_2$). The reaction mixture is immediately diluted with 150 mL of CH$_2$Cl$_2$ and neutralized with NaHCO$_3$(20 mL). The resulting suspension is washed with NaHCO$_3$ (100 mL), dried over Na$_2$SO$_4$, filtered and concentrated. The crude product is purified by flash chromatography (20% EtOAc/petroleum ether) to give 541 mg (66%, 2 steps) of phenyl 3-azido-4-O-benzoyl-3,6-di-deoxy-1-thio-4-L-galactopyranoside (β-18): $R_f$0.21 (30% EtOAc/petroleum ether); $^1$H NMR (CDCl$_3$, 270 MHz) a 7.88–7.85 (m, 2H, ArH), 7.68–7.56 (m, 3H, ArH), 7.47–7.35 (m, 5H, ArH), 5.44 (d, J=2.3 Hz, 1H, H-4), 4.57 (d, J=8.9 Hz, 1H, H-1), 3.92 (q, J=6.3 Hz, 1H, H-5), 3.83 (dd, J=2.3, 9.9 Hz, 1H, H-3), 3.74 (dt, J=2.0, 9.9 Hz, 1H, H-2), 2.62 (d, J=2.0, 1H, OH), 1.26 (d, J=6.3 Hz, 3H, H-6).

To a solution of phenyl 3-azido-4-O-benzoyl-3,6dideoxy-1-thio-β-L-galactopyranoside (β-18) (118 mg, 0.307 mmol) in 5 mL of CH$_2$C$_2$ is added TEA (256 μL, 1.87 mmol), pivaloyl chloride (114 μL, 0.921 mmol) and DMAP (19 mg, 0.154 mmol). The reaction mixture is stirred at room temperature for 12 h, diluted with 15 mL of CH$_2$Cl$_2$, washed with 1M HCl (2×10 mL), dried over Na$_2$SO$_4$, filtered and concentrated. The crude product is purified by flash chromatography (20% EtOAc/petroleum ether) to give 114 mg (80%) of phenyl 3-azido-4-O-benzoyl-3,6-di-deoxy-2-O-pivaloyl-1-thio-β-L-galactopyranoside (β-19): $R_f$0.54 (20% EtOAc/petroleum ether); $^1$H NMR (CDCl$_3$, 270 MHz) δ 7.93 (d, 2H, ArH), 7.59–7.56 (m, 3H, ArH), 7.46–7.26 (m, 5H, ArH), 5.53 (d, J=2.6 Hz, 1H, H-4), 5.25 (t, J=9.9 Hz, 1H, H-2) 4.73 (d, J=9.9 Hz, 1H, H-1), 3.92 (q, J=6.3 Hz, 1H, H-5), 3.79 (dd, J=2.6, 9.9 Hz, 1H, H-3), 1.42–1.21 (m, 12H, H-6, CH$_3$); $^{13}$C NMR (CDCl$_3$, 68 MHz) δ 176.8, 165.9, 133.8, 133.7, 131.8, 130.2, 129.0, 128.9, 128.6, 128.4, 86.1, 74.4, 71.6, 68.3, 63.9, 39.1, 27.3, 16.9; FAMS C$_{24}$H$_{27}$O$_5$N$_3$ (MNa$^+$) calcd 492.1569, found 492.1579.

To a solution of phenyl 3-azido-4-O-benzoyl-3,6-di-deoxy-2-O-pivaloyl-1-thio-β-L-galactopyranoside (β-19) (270 mg, 0.575 mmol) in 10 mL of CH$_2$Cl$_2$ at −78° C. is added a solution of mCPBA (159 mg of 64% material, 0.920 mmol) in 2 mL of CH$_2$Cl$_2$. The reaction mixture is allowed to warm to −20° C. and then quenched with TEA (500 μL, 3.59 mmol). The reaction mixture is diluted with 10 mL of CH$_2$Cl$_2$. washed with saturated NaHSO$_3$ (10 mL), saturated NaHCO$_3$ (10 mL), dried over Na$_2$SO$_4$, filtered and concentrated. The crude product is purified by flash chromatography (60% EtOAc/petroleum ether) to give 231 mg (83%) of 3-azido-4-O-benzoyl1,3,6-tri-deoxy-2-O-pivaloyl-1-(phenylsulfinyl)-β-L-galactopyranose (β-20) as a mixture of diastereomers: $R_f$0.26 (50% EtOAc/petroleum ether).

7.4. 3-Azido-4-O-benzoyl-1,3,6-trideoxy-2-O-pivaloyl-1-(phenylsulfinyl)-β-D-galactopyranose (β-D-20)

By the method above, but beginning with D-fucose, the title compound is prepared.

7.5. 1,6-Dideoxy-2-(4-methoxybenzyl)-1-(phenylsulfinyl)-α-L-galactopyranose 3,4-carbonate (α-11)

To a solution of phenyl 6-deoxy-2-(4-methoxybenzyl)-1-thio-α-L-galacto-pyranoside (α-9, prepared above) (743 mg, 1.98 mmol) in 40 mL of THF is added 1,1'-carbonyldiimidazole (422 mg, 2.60 mmol). The reaction mixture is stirred at room temperature for 24 h and then quenched with 5 mL of 1M HCl. The resulting suspension is diluted with 40 mL of CH$_2$Cl$_2$, washed with of 1M HCl (15 mL), dried over Na$_2$SO$_4$, filtered and concentrated. The crude product is purified by flash chromatography (35% EtOAc/petroleum ether) to give 766 mg (97%) of phenyl 6-deoxy-2-(4-methoxybenzyl)-1-thio-α-L-galactopyranoside 3,4-carbonate (α-10): $R_f$0.40 (40% EtOAc/petroleum ether) $^1$H NMR (CDCl$_3$, 300 MHz) δ 7.50 (d, 2H, ArH), 7.38–7.32 (m, 5H, ArH), 6.96 (d, 2H, ArH), 5.74 (d, J=5.6 Hz, 1H, H-1), 4.81 (d, J=11.2 Hz, 1H, CH$_2$), 4.74 (d, J=5.1, 9.6 Hz, 1H, H-3), 4.67–4.60 (m, 2H, H-4 and CH$_2$), 4.53 (q, J=6.1, 1H, H-5), 4.23–4.18 (m, 1H, H-2), 3.88 (s, 3H, CH$_3$), 1.35 (d, J=6.1 Hz,3H, H-6); $^{13}$C NMR (CDCl$_3$, 68 MHz) δ 160.0, 154.0, 134.4, 131.7, 130.0, 129.1, 128.8, 127.6, 114.2, 86.5, 76.5, 74.7, 73.5, 72.7, 65.0, 55.5, 15.6.

To a solution of phenyl 6-deoxy-2-(4-methoxybenzyl)-1-thio-α-L-galactopyranoside 3,4-carbonate (α-10) (280 mg, 0.691 mmol) in 10 mL of $CH_2Cl_2$ at −78° C. is added a solution of mCPBA (173 mg, 1.11 mmol) in 2 mL of $CH_2Cl_2$. The reaction mixture is allowed to warm to −20° C. and then quenched with TEA (500 µL, 3.59 mmol). The reaction mixture is diluted with 10 mL of $CH_2Cl_2$, washed with saturated $NaHSO_3$ (10 mL), saturated $NaHCO_3$ (10 mL), dried over $Na_2SO_4$, filtered and concentrated. The crude product is purified by flash chromatography (60% EtOAc/petroleum ether) to give 266 mg (92%) of 1,6-dideoxy-2-(4-methoxybenzyl)-1-(phenylsulfinyl)-α-L-galactopyranose 3,4-carbonate (α-11) as a mixture of diastereomers: $R_f$ 0.26 (50% EtOAc/petroleum ether).

7.6. 1,6-Dideoxy-2-(4-methoxybenzyl)-1-(phenylsulfinyl)-α-D-galactopyranose 3,4-carbonate (α-D-11)

By the method above, but beginning with D-fucose, the title compound is prepared.

7.7. 1,6-Dideoxy-3,4-O-isopropylidene-2-(4-methoxybenzyl)-1-(phenylsulfinyl)-β-L-galactopyranose (8)

To a solution of phenyl 6-deoxy-3,4-O-isopropylidene-2-(4-methoxybenzyl)-1-thio-L-galactopyranoside (7, prepared above), (290 mg, 0.69 mmol) in 10 mL of $CH_2Cl_2$ at −78° C. is added a solution of mCPBA (170 mg, 1.1 mmol) in 2 mL of $CH_2Cl_2$. The reaction mixture is allowed to warm to −20° C. and then quenched with TEA (500 µL, 3.59 mmol). The reaction mixture is diluted with 10 mL of $CH_2Cl_2$, washed with saturated $NaHSO_3$ (10 mL), saturated $NaHCO_3$ (10 mL), dried over $Na_2SO_4$, filtered and concentrated. The crude product is purified by flash chromatography (EtOAc/petroleum ether) to give 1,6-dideoxy-3,4-O-isopropylidene-2-(4-methoxybenzyl)-1-(phenylsulfinyl)-L-galactopyranose (8) as a mixture of diastereomers.

7.8. 1,6-Dideoxy-3,4-O-isopropylidene-2-(4-methoxybenzyl)-1-(phenylsulfinyl)-D-galactopyranose (D-8)

By the method above, but beginning with D-fucose, the title compound is prepared.

7.9. 3,4-Di-O-benzoyl-1,6-dideoxy-2-O-(4-methoxybenzyl)-1-(phenylsulfinyl)-β-L-allopyranose (β-13 sulfoxide)

To a solution of phenyl 6-deoxy-3,4-di-O-benzoyl-2-O-(4-methoxybenzyl)-1-thio-β-L-allopyranoside (β-13, prepared above) (400 mg, 0.7 mmol) in 10 mL of $CH_2Cl_2$ at −78° C. is added a solution of mCPBA (170 mg, 1.1 mmol) in 2 mL of $CH_2Cl_2$. The reaction mixture is allowed to warm to −20° C. and then quenched with TEA (500 µL, 3.59 mmol). The reaction mixture is diluted with 10 mL of $CH_2Cl_2$, washed with saturated $NaHSO_3$ (10 mL), saturated $NaHCO_3$ (10 nL), dried over $Na_2SO_4$, filtered and concentrated. The crude product is purified by flash chromatography (EtOAc/petroleum ether) to give 1,6-dideoxy-3,4-di-O-benzoyl-2-O-(4-methoxybenzyl)-1-(phenylsulfinyl)-β-L-allopyranose as a mixture of diastereomers.

7.10. 3,4-Di-O-benzoyl-1,6-dideoxy-2-O-(4-methoxybenzyl)-1-(phenylsulfinyl)-β-D-allopyranose (β-D-13 sulfoxide)

By the method above, but beginning with D-fucose, the title compound is prepared.

7.11. 3-Azido-4-O-benzoyl-1,3,6-trideoxy-2-O-(4-methoxybenzyl)-1-(phenylsulfinyl)-β-L-galactopyranose (β-17)

To a solution of phenyl 3-azido-4-O-benzoyl-3,6-dideoxy-2-O-(4-methoxybenzyl)-1-thio-β-L-galactopyranoside (β-16, prepared above), (350 mg, 0.7 mmol) in 10 mL of $CH_2Cl_2$ at −78° C. is added a solution of mCPBA (170 mg, 1.1 mmol) in 2 mL of $CH_2Cl_2$. The reaction mixture is allowed to warm to −20° C. and then quenched with TEA (500 µL, 3.59 mmol). The reaction mixture is diluted with 10 mL of $CH_2Cl_2$, washed with saturated $NaHS_3$ (10 mL), saturated $NaHCO_3$ (10 mL), dried over $Na_2SO_4$, filtered and concentrated. The crude product is purified by flash chromatography (EtOAc/petroleum ether) to give the title compound as a mixture of diastereomers.

7.12. 3-Azido-4-O-benzoyl-1,3,6-trideoxy-2-O-(4-methoxybenzyl)-1-(phenylsulfinyl)-β-D-galactopyranose (α-D-17)

By the method above, but beginning with D-fucose, the title compound is prepared.

7.13. 2-Azido-1,2,6-trideoxy-1-(phenylsulfinyl)-α-L-galactopyranose 3,4-carbonate (α-25)

The mixed anomers of 1,3,4-tri-O-acetyl-2azido-2,6-dideoxy-L-galactopyranoside (21) are prepared from L-fucose by the method of A. Anisuzzaman and D. Horton, Carb. Res., 169, 258–262 (1987). To a solution of 21 (3.80 g, 12.1 mmol) in 120 mL of $CH_2Cl_2$, thiophenol (3.1 mL, 3.3 g, 30.1 mmol) and $BF_3.Et_2O$ (7.4 mL, 8.5 g, 60.3 mmol) are added at room temperature. The reaction mixture is heated at 40° C. for 50 min, then quenched with $H_2O$ (20 mL). The organic layer is washed with brine (100 mL), dried over $Na_2SO_4$, filtered and concentrated to afford a mixture of anomers of phenyl 2-azido-3,4-di-O-acetyl-2,6-dideoxy-1-thio-L-galactopyranoside (22) as a clear oil: $R_f$ 0.39 (25% EtOAc/petroleum ether).

To a solution of 22 (4.40 g, 12.1 mmol) in 120 mL of methanol is added $K_2CO_3$ (5.97 g, 36.2 mmol). The reaction mixture is stirred at room temperature for 1.5 h and then neutralized with amberlite resin, filtered, concentrated and purified by flash chromatography (5% methanol/$CH_2Cl_2$) to yield 3.10 g (91%, 2 steps) of phenyl 2-azido-2,6-dideoxy-1-thio-L-galactopyranoside (23) as a 2.5:1 (α:β) mixture of anomers: $R_f$ 0.10 (25% EtOAc/petroleum ether); $^1H$ NMR ($CDCl_3$, 270 MHz) mixture of anomers, δ 7.61–7.27 (m, 10H), 5.61 (d, J=5.3 Hz, 1H, H-1α), 4.50 (q, J=6.6 Hz, 1H, H-5α), 4.42 (d, J=9.9 Hz, 1H, H-1β), 4.11 (dd, J=10.1, 5.4 Hz, 2H, H-3α,β), 3.88–3.85 (m, 3H), 3.73 (br s, 1H), 3.63 (q, J=6.3 Hz, 1H, H-5β), 3.59–3.40 (m, 1H), 2.81 (br s, 1H, OH), 2.47 (br s, 1H, OH), 2.23 (br s, 1H, OH), 1.72 (br s, 1H, OH), 1.37 (d, J=6.3 Hz, 3H, H-6β), 1.30 (d, J=6.6 Hz, 3H, H-6α).

To a solution of 23 (2.90 g, 10.3 mmol) in 100 mL of $CH_2Cl_2$ at 0° C. is added 1,1'-carbonyldiimidazole (3.34 g, 20.6 mmol). The reaction mixture is allowed to warm to room temperature for 15 min and quenched with 50 mL of $H_2O$. The aqueous layer is extracted with $CH_2Cl_2$ (3×40 mL), and the organic layers are combined, dried over $Na_2SO_4$, filtered, concentrated and purified by flash chromatography (gradient elution with 15–25% EtOAc/petroleum ether) to yield 2.30 g (73%) of phenyl 2-azido-2,6-dideoxy-1-thio-α-L-galactopyranoside 3,4-carbonate 24 as a white foam: $R_f$ 0.38 (25% EtOAc/petroleum ether). The β-anomer, $R_f$ 0.22, is not isolated. $^1H$ NMR ($CDCl_3$, 270 MHz) (α-24): δ 7.52–7.32 (m, 5H), 5.64 (d, J=5.6 Hz, 1H, H-1), 4.90 (dd, J=7.3, 5.6 Hz, 1H, H-3), 4.66 (dd, J=7.6, 2.0 Hz, 1H, H-4), 4.47 (dq, J=6.6, 2.0 Hz, 1H, H-5), 4.30 (app t, J=5.6 Hz, 1H, H-2), 1.36 (d, J=6.6 Hz, 3H, H-6); $^{13}C$ NMR ($CDCl_3$, 68 MHz) δ 153.5, 133.1, 132.0, 129.3, 128.2, 85.3, 76.3, 74.4, 64.5, 59.0, 15.7; FABMS $C_{13}H_{13}N_3O_4S$ ($MNa^+$) calcd 330.0524, found 330.0520.

To a solution of phenyl 2-azido-2,6-dideoxy-1-thio-α-L-galactopyranoside 3,4-carbonate (α-24) (0.860 g, 2.80 mmol) in 50 mL of $CH_2Cl_2$ is added $NaHCO_3$ at room temperature. The reaction mixture is then cooled to −78° C., and mCPBA (0.878 g, 2.80 mmol, 50–60%) is added. The reaction mixture is stirred at −78° C. for 30 minutes and then allowed to warm to −40° C. over 1 h. The reaction is quenched with dimethyl sulfide (1 mL) at −40° C. and then poured into a solution of saturated NaHCO$_3$ (50 mL) and extracted with CH$_2$Cl$_2$ (3×30 mL) The organic layers are combined, dried over Na$_2$SO$_4$, filtered, concentrated and purified by flash chromatography (40% EtOAc/petroleum ether) to afford 0.871 g (96%) of 2-azido-1,2,6-trideoxy-1-(phenylsulfinyl)-α-L-galactopyranose 3,4-carbonate (α-25) as a mixture of diastereomers: R$_f$ (major diastereomer) 0.14 (40% EtOAc/petroleum ether).

7.14. 2-Azido-1,2,6-trideoxy-1-(phenylsulfinyl)-α-D-galactopyranose 3,4-carbonate (α-D-25)

By the method above, but beginning with D-fucose, the title compound is prepared.

7.15. 2-Azido-3,4-di-O-acetyl-1,2,6-trideoxy-1-(phenylsulfinyl)-L-galactopyranose (26)

To a solution of phenyl 2-azido-3,4-di-O-acetyl-2,6-dideoxy-1-thio-L-galactopyranoside (22) (1.02 g, 2.80 mmol) in 50 mL of CH$_2$Cl$_2$ is added NaHCO$_3$ at room temperature. The reaction mixture is cooled to −78° C., and mCPBA (0.878 g, 2.80 mmol, 50–60%) is added. The reaction mixture is stirred at −78° C. for 30 minutes and then allowed to warm to −40° C. over 1 h. The reaction is quenched with dimethyl sulfide (1 mL) at −40° C. and then poured into a solution of saturated NaHCO$_3$ (50 mL) and extracted with CH$_2$Cl$_2$ (3×30 mL) The organic layers are combined, dried over Na$_2$SO$_4$, filtered, concentrated, and purified by flash chromatography (EtOAc/petroleum ether) to afford the title compound 26 as a mixture of diastereomers.

7.16. 2-Azido-3,4-di-O-acetyl-1,2,6-trideoxy-1-(phenylsulfinyl)-D-galactopyranose (D-26)

By the method above, but beginning with D-fucose, the title compound is prepared.

7.17. 2,6-Bis-O-(4-methoxybenzyl)-1-deoxy-1-(phenylsulfinyl)-β-D-galactopyranose 3,4-carbonate (33)

By the method of A. Sarkar, K. Matta, Carbohydr. Res., 233, 245–250 (1992), 1,2,3,4,5,6-penta-O-acetyl-β-D-galactopyranoside is converted into phenyl 1-thio-β-D-galactopyranoside (27).

To a solution of 27 (5.3 g, 20 mmol) in 100 mL of DMF is added 2,2-dimethoxypropane (6.0 mL, 49 mmol) and p-toluenesulfonic acid monohydrate (0.74 g, 3.9 mmol). The reaction is stirred at room temperature for 2 days and then diluted with water (150 mL) and extracted with CH$_2$Cl$_2$ (3×150 mL). The organic layers are combined, dried over Na$_2$SO$_4$ and concentrated in vacuo. The residue is purified by flash chromatography (100% EtOAc) to give 4.9 g (80%) of phenyl 3,4-O-isopropylidine-1-thio-β-D-galactopyranoside 28, R$_f$ 0.50 (100% EtOAc). $^1$H NMR (CDCl$_3$, 270 MHz) δ 7.51–7.55 (m, 2H), 7.29–7.33 (m, 3H), 4.47 (d, J=9.9 Hz, 1H, H-1), 4.18 (dd, J=5.27, 1.65 Hz, 1H), 4.11 (appt, J=6.3 Hz, 1H), 3.95–4.03 (m, 1H), 3.78–3.90 (m, 2H), 3.57 (dd, J=10.2, 6.9 Hz, 1H), 1.41 (s, 3H), 1.33 (s, 3H).

To a solution of 28 (4.9 g, 16 mmol) in 120 mL of DMF at 0° C. is added NaH (1.5 g, 63 mmol). The solution is allowed to warm to room temperature over 0.5 h, and then p-methoxybenzyl chloride (8.5 mL, 63 mmol) and tetrabutylammonium iodide (4.1 g, 11 mmol) are added. After 4 h the reaction is quenched by pouring slowly into 500 mL of ice cold saturated NaHCOO with stirring. The product is extracted with CH$_2$Cl$_2$ (3×200 mL). The organic layers are dried over Na$_2$SO$_4$ and concentrated in vacuo to provide phenyl 2,6-bis-O-(4-methoxybenzyl)-3,4-O-isopropylidine-1-thio-β-D-galactopyranoside 29, which is purified by flash chromatography (60% EtOAc/petroleum ether): R$_f$ 0.51; $^1$H NMR (CDCl$_3$, 270 MHz) δ 7.52–7.56 (m, 2H), 7.17–7.36 (m, 7H), 6.83–6.88 (m, 4H), 4.75 (d, J=10.9 Hz, 1H), 4.42–4.69 (m, 4H), 4.18–4.26 (m, 2H), 3.88–3.93 (m, 1H), 3.75–3.80 (m, 8H), 3.49–3.57 (m, 1H), 1.42 (s, 3H), 1.35 (s, 3H).

The ketal 29 is dissolved in 100 mL of MeOH and p-toluenesulfonic acid monohydrate (0.60 g, 3.1 mmol) is added. The reaction is stirred at room temperature for 10 h and then saturated NaHCO$_3$ (50 mL) is added, followed by water (100 mL). The product is extracted with CH$_2$Cl$_2$ (4×100 mL), and the organic layers are combined, washed with saturated NaCl, (1×300 mL), dried over Na$_2$SO$_4$ and concentrated in vacuo. The residue is purified by flash chromatography (50% EtOAc/petroleum ether) to give 5.4 g (68% over 2 steps) of phenyl 2,6-bis-O-(4-methoxybenzyl)-1-thio-β-D-galactopyranoside 31: R$_f$ 0.26 (50% EtOAc/petroleum ether), $^1$H NMR (CDCl$_{3,\ 270}$ MHz) δ 7.56–7.60 (m, 2H), 7.22–7.33 (m, 7H), 6.85–6.91 (m, 4H), 4.87 (d, J=10.6 Hz, 1H, H-1), 4.58–4.65 (m, 2H), 4.50 (s, 2H), 4.02–4.03 (m, 1H), 3.81 (s, 3H), 3.80 (s, 3H), 3.75–3.77 (m, 2H), 3.59–3.62 (m, 3H).

To a solution 31 (5.4 g, 10 mmol) in 400 mL of CH$_2$Cl$_2$ at 0° C. is added carbonyldiimidazole (2.5 g, 15 mmol). The solution is stirred at 0° C. for 20 min and then for 12 h at room temperature. The solution is then quenched by the addition of brine (100 mL). The organic layer is dried over Na$_2$SO$_4$, and concentrated in vacuo. The residue is purified by flash chromatography (40% EtOAc/petroleum ether) to give 5.3 g (93%) of phenyl 2,6-bis-O-(4-methoxybenzyl)-1-thio-β-D-galactopyranoside 3,4-carbonate 32 as a syrup: R$_f$ 0.69 (50% EtOAc/petroleum ether); $^1$H NMR (CDCl$_3$, 270 MHz) δ 7.48–7.51 (m, 2H), 7.22–7.31 (m, 7H), 6.87–6.91 (m, 4H), 4.77–4.83 (m, 3H), 4.63 (s, 2H), 4.48 (s, 2H), 3.96 (app t, J=6.26 Hz, 1H), 3.82 (s, 6H), 3.67–3.75 (m, 3H); $^{13}$C NMR (CDCl$_3$, 68 MHz) δ 159.8, 159.5, 153.9, 133.0, 132.2, 130.1, 129.9, 129.6, 129.2, 128.8, 128.1, 114.1, 114.0, 85.7, 78.1, 76.3, 74.8, 74.1, 73.6, 73.5, 68.0, 55.5.

To a solution of 32 (0.80 g 1.5 mmol) in 50 mL of CH$_2$Cl$_2$ at −78° C. is added 64% mCPBA (0.530 g, 1.96 mmol). The reaction is allowed to warm to −30° C. and quenched with dimethyl sulfide (0.3 mL, 4 mmol). Saturated NaHCO$_3$ (100 mL) is added and the product extracted with CH$_2$Cl$_2$ (2×150 mL). The organic layers are combined, dried over Na$_2$SO$_4$ and concentrated in vacuo. The residue is purified by flash chromatography (50% EtOAc/petroleum ether) to give 0.81 g (99%) of 2,6-bis-O-(4-methoxybenzyl)-1-deoxy-1-(phenylsulfinyl)-α-D-galactopyranose 3,4-carbonate 33 (a mixture of diastereomers) as a white foam: R$_f$ 0.19 (50% EtOAc/petroleum ether).

7.18. 2,6-Bis-O-(4-methoxybenzyl)-3,4-O-isopropylidine-1-deoxy-1-(phenylsulfinyl)β-D-galactopyranose (30)

To a solution of 29 (1.5 mmol) in 50 mL of CH$_2$Cl$_2$ at −78° C. is added 64% mCPBA (0.530 g, 1.96 mmol). The reaction is allowed to warm to −30° C. and quenched with dimethyl sulfide (0.3 mL, 4 mmol). Saturated NaHCO$_3$ (100 mL) is added, and the product is extracted with CH$_2$Cl$_2$ (2×150 mL). The organic layers are combined, dried over Na$_2$SO$_4$ and concentrated in vacuo. The residue is purified by flash chromatography (EtOAc/petroleum ether) to give the title compound as a mixture of diastereomers.

7.19. 2,3,4,6-tetra-O-pivaloyl-1-deoxy-1-(phenylsulfinyl)-α-D-mannopyranose (37)

To a solution of D-mannose 34 (1.1 g, 6.1 mmol) in 30 mL of pyridine at room temperature is added pivaloyl chloride (4.5 mL, 36.6 mmol). The solution is heated to 100° C. for 48 hr and then allowed to cool. The solvent is removed in vacuo and the residue is dissolved in 50 mL of $CH_2Cl_2$ and washed with 5% HCl (4×60 mL), dried over $Na_2SO_4$, filtered, and concentrated to afford a clear oil which is purified by flash chromatography (10% EtOAc/hexane) to give 3.6 g (97%) of penta(pivaloyl) D-mannose 35, as a white solid, a 6:1 (α:β) mixture of anomers: $R_f$ (β-anomer) 0.18 (10% EtOAc/hexane); $R_f$ (α-anomer) 0.1 (10% EtOAc/hexane); $^1H$ NMR ($CDCl_3$, 300 MHz) 6 6.01 (d, J=2.0 Hz, 1H, H-1β), 5.83 (d, J=1.0 Hz, 1H, H-1α), 5.54–5.35 (m, 4H), 5.31–5.27 (m, 1H), 5.16 (dd, J=10.2, 3.0 Hz, 1H, H-3α), 4.20–4.13 (m, 4H), 4.05–3.97 (m, 1H, H-5β), 3.87–3.81 (m, 1H, H-5α), 1.30 (s, 9H), 1.29 (s, 9H), 1.28 (s, 9H), 1.23 (s, 9H), 1.22 (s, 9H), 1.17 (s, 18H), 1.16 (s, 9H), 1.13 (s, 9H), 1.12 (s, 9H).

To a solution of 35 (3.6 g, 6.0 mmol) in 40 mL of $CH_2Cl_2$ is added thiophenol (0.71 mL, 6.9 mmol) followed by boron trifluoride diethyl ether complex (2.95 mL, 24 mmol). The reaction mixture is stirred at room temperature for 10 hr and then quenched by the addition of 20 ml of saturated $NaHCO_3$ solution. The reaction mixture is then extracted with $CH_2Cl_2$ (3×30mL). The combined organic layers are dried over $Na_2SO_4$, concentrated, and purified by flash chromotography (8% EtOAc/hexane) to give 3.1 g (85%) of phenyl 2,3,4,6-tetra-O-pivaloyl-1-thio-α-D-mannopyranoside 36 as a white solid: $R_f$ 0.3 (8% EtOAc/hexane); $^1H$ NMR ($CDCl_3$, 300 MHz) δ 7.54–7.40 (m, 2H), 7.30–7.22 (m, 4H), 5.50 (m, 2H, H-4, H-2), 5.39 (d, J=1.3 Hz, 1H, H-1), 5.29 (dd, J=10.2, 3.3 Hz, 1H, H-3), 4.62 (m, 1H, H-5), 4.22 (dd, J=12.5, 4.3 Hz, 1H, H-6), 4.10 (dd, J=12.5, 1.3 Hz, 1H, H-6), 1.26 (s, 9H), 1.21 (s, 9H), 1.18 (s, 9H), 1.14 (s, 9H); $^{13}C$ NMR ($CDCl_3$, 68 MHz) δ 177.8, 176.9, 176.7, 176.4, 132.8, 131.8, 129.1, 127.9, 86.2, 70.7, 69.9, 69.6, 65.0, 61.9, 38.7, 38.6, 38.5, 26.9, 26.4; FABMS $C_{32}H_{48}O_9S$ (MNa+) calcd 631. 2917, found 631.2943.

To a solution of 36 (1.38 g, 2.27 mmol) in 65 mL of $CH_2Cl_2$ at –78° C. is added m-CPBA (612 mg, 64%, 2.27 mmol). The reaction mixture is allowed to warm to –15° C. and then quenched with dimethyl sulfide (1 mL, 13.6 mmol) and allowed to warm to room temperature. The reaction mixture is diluted with 50 mL of $CH_2Cl_2$, extracted with $H_2O$ (100 mL), saturated $NaHCO_3$ (100 mL), saturated NaCl (100 mL), dried over $Na_2SO_4$, filtered, and concentrated to afford a white solid. The sulfoxide is purified using flash chromatography (30% EtOAc/hexane) to afford 1.07 g (76%) of the title compound 37 as a mixture of diastereomers: $R_f$ 0.35 and 0.38 (30% EtOAc/hexane).

7.20. 1-deoxy-1-(phenylsulfinyl)-2,3,4,6-tetra-O-pivaloyl-β-D-galactopyranose (41)

To a solution of galactose pentaacetate (5.00 g, 12.8 mmol) in 125 mL of $CH_2Cl_2$ is added thiophenol (1.49 mL, 14.1 mmol) and boron trifluoride diethyl ether complex (4.73 mL, 38.4 mmol). The reaction mixture is stirred at room temperature for 5 h and then poured into 200 mL of ice water. The organic layer is washed with saturated $NaHCO_3$ (200 ml), dried over $Na_2SO_4$, filtered, concentrated and purified by flash chromatography (35% EtOAc/hexane) to give 5.4 g (96%) of 1-deoxy-1-(phenylthio)-2,3,4,6-tetra-O-acetyl-β-D-galactopyranose 39: $R_f$ 0.22 (35% EtOAc/hexane); $^1H$ NMR ($CDCl_3$, 270 MHz) δ 7.35–7.65 (m, 5 H, ArH), 5.50 (br d, J=3.3 Hz, 1 H, H-4), 5.32 (t, J=9.8 Hz, 1 H, H-2), 5.13 (dd, J=9.8, 3.3 Hz, 1 H, H-3), 4.80 (d, J=9.8 Hz, 1 H, H-1), 4.13–4.32 (m, 2 H, H-6, H-6'), 4.02 (br t, J=6.5 Hz, 1 H, H-5), 2.02–2.23 (4s, 12 H, OAc).

To a solution of thioglycoside 39 (1.10 g, 2.5 mmol) in 50 mL of MeOH is added $K_2CO_3$ in small portions, until the reaction mixture tested basic to pH paper (pH 11). The reaction mixture is stirred at room temperature for 15 min and then neutralized with Amberlite resin (acid form). The resin is removed by filtration and washed with MeOH (2×50 mL). The filtrates are concentrated and azeotroped from toluene to remove the residue MeOH to afford 1-deoxy-1-(phenylthio)-β-D-galactopyranose which is taken on to the next step without further purification.

To a solution of 1-deoxy-1-(phenylthio)-β-D-galactopyranose (0.38 g, 1.4 mmol) in 25 mL of pyridine, pivaloyl chloride (1.75 mL, 14.0 mmol) and DMAP (0.200 g, 1.40 mmol) are added. The reaction mixture is stirred at 90–100° C. for 8 h. Pyridine is removed under reduced pressure, and the residue is dissolved in 100 mL of $CH_2Cl_2$ and washed with dilute HCl (100 mL), $H_2O$ (100 mL), dried over $Na_2SO_4$, filtered, concentrated and purified by flash chromatography (10% EtOAc/hexane) to give 0.65 g (76%) of 1-deoxy-1-(phenylthio)-2,3,4,6-tetra-O-pivaloyl-β-D-galactopyranose 40: $R_f$ 0.59 (15% EtOAc/hexane); $^1H$ NMR (CDCl3, 270 MHz) δ 7.97 (d, J=8.9 Hz, 2 H, ArH), 7.70 (t, J=7.3 Hz, 1 H, ArH), 7.60 (t, J=7.3 Hz, 2 H, ArH), 5.39 (t, J=9.9 Hz, 1 H, H-2), 5.30 (d, J=3.0 Hz, 1 H, H-4), 5.10 (dd, J=9.9, 3.0 Hz, 1 H, H-3), 4.57 (d, J=9.9 Hz, 1 H, H-1), 4.05–4.20 (m, 2 H, H-6), 3.79 (dd, J=10.6, 5.9 Hz, 1 H, H-5), 1.25-(s, 9 H), 1.18 (s, 9 H), 1.08 (s, 9H), 0.92 (s, 9 H). $^{13}C$ NMR ($CDCl_3$, 270 MHz) δ 177.7, 177.0, 176.7, 176.3, 134.4, 134.2, 131.0, 128.7, 89.4, 74.9, 71.7, 65.9, 63.9, 60.5, 38.4, 38.7, 38.6, 27.1.

To a solution of thioglycoside 40 (0.62 g, 1.0 mmol) in 20 mL of $CH_2Cl_2$ at –78° C. is added 67% m-CPBA (0.26 g, 1.0 mmol). The reaction mixture is stirred at –78° C. for 2 h and then allowed to slowly warm up to room temperature. Saturated $NaHCO_3$ is added until the solution is basic. The reaction mixture is diluted with 100 mL of $CH_2Cl_2$ and washed with $H_2O$ (100 mL), saturated NaCl (100 mL), dried over $Na_2SO_4$, filtered, concentrated and purified by flash chromatography (15% EtOAc/hexane) to give 0.59 g (92%) of the title compound 41 as a mixture of diastereomers: $R_f$ 0.38, 0.19 (20% EtOAc/hexane). FABMS $C_{32}H_{48}O_{10}S$ ($MNa^+$) calcd 647.2866, found 647.2868.

7.21. 2,3,4,6-tetra-O-pivaloyl-1-deoxy-1-(phenylsulfinyl)-β-D-glucopyranose (45)

To a solution of D-glucose 42 (500 mg, 2.77 mmol) in 25 mL of pyridine is added pivaloyl chloride (3.42 mL, 3.34 g, 27.75 mmol) followed by DMAP (34 mg, 0.27 mmol). The reaction mixture is heated at 100° C. for 12 h, cooled to room temperature and quenched with 2 mL methanol. The reaction mixture is concentrated and the resulting residue is taken up in 25 mL $CH_2Cl_2$, washed with 1N HCl (3×25 mL), saturated NaCl (25 mL), dried over $Na_2SO_4$, filtered, concentrated and purified by flash chromatography (10% EtOAc/hexane) to afford 1.49 g (90%) of 1,2,3,4,6-penta-O-pivaloyl-β-D-glucopyranose 43: $R_f$ 0.18 (5% EtOAc/hexane); $^1H$ NMR ($CDCl_3$, 270 MHz) δ 5.69 (d, J=8.2 Hz, 1H, H-1), 5.37 (app t, J=9.2 Hz, 1H, H-3), 5.21 (app t, J=8.7 Hz, 1H, H-4), 5.16 (app t, J=9.5 Hz, 1H, H-2), 4.06–4.17 (m, 2H, H-6), 3.86 (ddd, J=9.8, 4.8, 2.3 Hz, 1H, H-5), 1.21 (s, 9H), 1.17 (s, 9H), 1.15 (s, 9H), 1.12 (s, 18H).

To a solution of 43 (1.49 g, 2.49 mmol) in 50 mL $CH_2Cl_2$ is added thiophenol (0.64 mL, 686 mg, 6.22 mmol) followed by boron trifluoride diethyl ether complex (1.53 mL, 1.76 g, 12.45 mmol). The reaction mixture is stirred at room temperature for 4 h and quenched by the slow addition of 10 mL saturated $NaHCO_3$ solution. The reaction mixture is diluted with 100 mL of $CH_2Cl_2$, washed with $H_2O$ (100 mL), saturated NaCl (100 mL), dried over $Na_2SO_4$, filtered, concentrated and purified by flash chromatography (5% EtOAc/hexane) to afford 1.24 g (82%) of 1-deoxy-1-(phenylthio)-2,3,4,6-tetra-O-pivaloyl-β-D-glucopyranose 44: $R_f$ 0.25 (5% EtOAc/hexane); $^1$H NMR (CDCl$_3$, 270 MHz) δ 7.47–7.50 (m, 2H), 7.22–7.30 (m, 3H), 5.34 (app t, J=9.4 Hz, 1H, H-3), 5.08 (app t, J=9.7 Hz, 1H, H-4), 5.03 (app t, J=9.7 Hz, 1H, H-2), 4.73 (d, J=9.8 Hz, 1H, H-1), 4.25 (dd, J=12.2, 1.6 Hz, 1H, H-6), 4.04 (dd, J=12.2, 5.9 Hz, 1H, H-6), 3.76 (ddd, J=10.2, 5.9, 1.6 Hz, 1H, H-5), 1.21 (s, 9H), 1.20 (s, 9H), 1.14 (s, 9H), 1.10 (s, 9H); $^{13}$C NMR (CDCl3, 68 MHz) δ 177.8, 176.9, 176.2, 176.1, 132.5, 132.2, 129.2, 129.1, 128.1. 128.8, 86.4, 76.3, 73.1, 69.3, 67.5, 62.1, 38.7, 38.6, 27.4, 27.0, 29.9; FABMS C$_{32}$H$_{48}$O$_9$S (MNa$^+$) calcd 631.2917, found 631.2943.

To a solution of 44 (1.24 g, 2.04 mmol) in 25 mL of CH$_2$Cl$_2$ at −78° C. is added a solution of 64% m-CPBA (550 mg, 2.04 mmol) in 10 mL of CH$_2$Cl$_2$. The reaction mixture is allowed to warm to −15° C., quenched with methyl sulfide (2.07 mL, 1.75 g, 6.8 mmol) and warmed to room temperature. The reaction mixture is then diluted with 25 mL CH$_2$Cl$_2$, washed with saturated NaHCO$_3$ (50 mL), H$_2$O (50 mL), saturated NaCl (50 mL), dried over Na$_2$SO$_4$, filtered, concentrated and purified by flash chromatography (30% EtOAc/hexane) to afford 1.14 g (89%) of the title compound 45 as a mixture of diastereomers: $R_f$ 0.14 and 0.28 (10% EtOAc/hexane).

7.22. 2,3,4,6-tetra-O-pivaloyl-1-deoxy-1-(phenylsulfinyl)-β-L-glucopyranose (L-45)

By the method above, but beginning with L-glucose, the title compound is prepared. To a solution of L-glucose L-42 -(0.500 g, 2.77 mmol) in 25 mL of pyridine is added pivaloyl chloride (3.4 mL, 27.8 mmol) and DMAP (0.034 g, 0.27 mmol). The reaction mixture is heated at 100° C. for 12 h, cooled to room temperature, quenched with 2 mL of MeOH, and concentrated. The resulting residue is taken up in 25 mL of CH$_2$Cl$_2$, washed with 1N HCl (3×25 mL), saturated NaCl (25 mL), dried over Na$_2$SO$_4$, filtered, concentrated, and purified by flash chromatography (10% EtOAc/petroleum ether) to afford 1.49 g (90%) of perpivolated glucose L-43. $R_f$ 0.18 (5% EtOAc/petroleum ether); $^1$H NMR (CDCl$_3$, 270 MHz) δ 5.69 (d, J=8.2 Hz, 1H, H-1), 5.37 (app t, J=9.4 Hz, 1H, H-3), 5.21 (app t, J=8.7 Hz, 1H, H-4), 5.16 (app t, J=9.5 Hz, 1H, H-2), 4.06–4.14 (m, 2H, H-6), 3.86 (ddd, J=9.8, 4.6, 2.3 Hz, 1H, H-5), 1.21 (s, 9H), 1.17 (s, 9H), 1.15 (s, 9H), 1.12 (s, 18H).

To a solution of perpivolated glucose (L-43) (1.49 g, 2.49 mmol) in 50 mL CH$_2$Cl$_2$ is added thiophenol (0.64 nL, 6.22 mmol) and BF$_3$.Et$_2$O (1.5 mL, 12.5 mmol). The reaction mixture is stirred at room temperature for 4 h, quenched with 10 mL of saturated NaHCO$_3$, diluted with 100 mL of CH$_2$Cl$_2$, washed with H$_2$O (100 mL), saturated NaCl (100 mL), dried over Na$_2$SO$_4$, filtered, concentrated, and purified by flash chromatography (5% EtOAc/petroleum ether) to afford 1.29 g (86%) of glucose thioglycoside L-44: $R_f$ 0.25 (5% EtOAc/petroleum ether); $^1$H NMR (CDCl$_3$, 270 MHz) δ 7.46–7.50 (m, 2H), 7.28–7.30 (m, 3H), 5.34 (app t, J=9.3 Hz, 1H, H-3), 5.08 (app t, J=9.7 Hz, 1H, H-4), 5.03 (app t, J=9.7 Hz, 1H, H-2), 4.73 (d, J=9.9 Hz, 1H, H-1), 4.25 (dd, J=12.1, 1.4 Hz, 1H, H-6), 4.05 (dd, J=12.2, 6.0 Hz, 1H, H-6), 3.76 (ddd, J=9.9, 5.9, 1.4 Hz, 1H, H-5), 1.15 (s, 9H), 1.14 (s, 9H), 1.10 (s, 9H), 1.09 (s, 9H); FABMS C$_{32}$H$_{48}$O$_9$S (MNa$^+$) calcd 631.2917, found 631.2952.

To a solution of glucose thioglycoside L-44 (1.07 g, 1.76 mmol) in 25 mL of CH$_2$Cl$_2$ at −78° C. is added a solution of mCPBA (0.476 g, 1.76 mmol, 64% from Sigma) in 10 mL of CH$_2$Cl$_2$. The reaction mixture is allowed to warm to −15° C., quenched using methyl sulfide (1.79 mL, 1.52 g, 5.9 mmol), warmed to room temperature. The reaction mixture is then diluted with 25 mL of CH$_2$Cl$_2$, washed with saturated NaHCO$_3$ (50 mL), H$_2$O (50 mL), saturated NaCl (50 mL), dried over Na$_2$SO$_4$, filtered, concentrated, and purified by flash chromatography (30% EtOAc/petroleum ether) to afford 0.977 g (89%) of sulfoxide L-45 as a mixture of diastereomers: $R_f$ 0.10 and 0.18 (15% EtOAc/petroleum ether).

7.23. 4-O-(2,3,4,6-tetra-O-pivaloyl-β-D-galactopyranosyl)-2,3,6-tri-O-pivaloyl-1-deoxy-1-phenylsulfinyl-β-D-glucopyranose (51)

To a solution of α-lactose monohydrate (46, 2.5 g, 6.9 mmol) in 45 mL of pyridine is added acetic anhydride (15 mL, 160 mmol) and DMAP (0.10 g, 0.82 mmol). The solution is stirred overnight and concentrated in vacuo. The residue is dissolved in 100 mL of CH$_2$Cl$_2$, washed with 1N HCl (3×50 mL), dried over Na$_2$SO$_4$, and concentrated to afford 4.7 g (100%) of octa-acetyl lactose 47 as the a anomer: $R_f$ 0.50 (75% EtOAc/hexane); $^1$H NMR (CDCl$_3$, 270 MHz) δ 6.23 (d, J=3.6 Hz, 1H, H-1), 5.44 (appt, J=9.7 Hz, 1H), 5.34 (d, J=2.6 Hz, 1H), 5.07–5.14 (m, 1H), 4.91–5.07 (m, 2H), 4.40–4.48 (m, 2H), 3.96–4.17 (m, 4H), 3.76–3.89 (m, 2H), 2.16 (s, 3H), 2.14 (s, 3H), 2.11 (s, 3H), 2.04 (s, 6H), 2.03 (s, 3H), 1.99 (s, 3H), 1.95 (s, 3H).

To a solution of octa-acetyl lactose 47 (4.7 g, 6.9 mmol) in 75 mL of CH$_2$Cl$_2$ is added thiophenol (1.42 mL, 13.9 mmol) followed by boron trifluoride diethyl ether complex (6.40 mL, 52.0 mmol). The reaction mixture is stirred at room temperature for 7 h and is then concentrated to half its volume by passing N$_2$ over it for 3 h. The reaction is stirred an additional 16 h at room temperature and then quenched by pouring slowly into 150 mL of saturated aqueous NaHCO$_3$ and stirring for 5 min. The product is extracted with CH$_2$Cl$_2$ (3×75 mL), dried over Na$_2$SO$_4$ and concentrated in vacua to an oil which is purified by flash chromatography to give 4.1 g (81%) of the phenyl thioglycoside of hepta-acetyl lactose 48 as a 5:1 (β:α) mixture of anomers: $R_f$ 0.34 (50% EtOAc/hexane); $^1$H NMR (CDCl$_3$, 270 MHz) β-anomer, δ 7.46–7.49 (m, 2H), 7.26–7.32 (m, 3H), 5.34 (d, J=3.3 Hz, 1H), 5.22 (appt, J=9.1 Hz, 1H), 5.07–5.14 (m, 1H), 4.87–4.97 (m, 2H), 4.67 (d, J=9.9 Hz, 1H, 4.45–4.56 (m, 2H), 4.03–4.16 (m, 3H), 3.86 (appt, J=6.8 Hz, 1H), 3.72–3.79 (m, 1H), 3.61–3.67 (m, 1H), 2.15 (s, 3H), 2.11 (s, 3H), 2.09 (s, 3H), 2.05 (s, 6H), 2.04 (s, 3H), 1.97 (s, 3H).

To a solution of acetylated phenyl thioglycoside 48 (4.1 g, 5.6 mmol) in 80 mL of methanol is added sodium methoxide (0.690 g, 12.8 mmol). The solution is stirred for 2 h at room temperature. Amberlite resin is added to the reaction mixture and stirred for five min. The neutralized reaction mixture is filtered through Celite and concentrated in vacua. The lactose phenyl thioglycoside 49 is taken on to the next step without further purification.

Lactose phenyl thioglycoside 49 is dissolved in 80 mL of pyridine, and pivaloyl chloride (20 mL, 170 mmol) and DMAP (0.10 g, 0.82 mmol) are added. The reaction mixture is heated to 110° C. for 24 h. Additional pivaloyl chloride (5 mL, 40 mmol) and DMAP (0.10 g, 0.82 mmol) are added. The reaction is heated for another 24 h at 110° C. The reaction is allowed to cool, poured into 50 mL of methanol, and stirred for 30 min. EtOAc (500 mL) is added, and the organic layer is washed with 1N HCl (6×100 mL) and saturated NaCl (3×100 mL), dried over Na$_2$SO$_4$ and concentrated in vacuc. The residue is purified by flash chromatography (10% EtOAc/hexane) to give 3.3 g (57%) of the phenyl thioglycoside of hepta-pivaloyl lactose 50 as a white foam, a 5:1 (β:α) mixture of anomers: $R_f$ 0.23 (10% EtOAc/hexane); $^1$H NMR (CDCl$_3$, 300 MHz) β-anomer, δ 7.45–7.49 (m, 2H), 7.26–7.31 (m, 3H), 5.40 (d, J=2.6 Hz, 1H), 5.24 (appt, J=9.4 Hz, 1H), 5.08–5.15 (m, 1H), 4.94–5.02 (m, 1H), 4.85 (appt, J=9.6 Hz, 1H), 4.70 (d, J=10.2 Hz, 1H), 4.49–4.59 (m, 2H), 3.82–4.24 (m, 5H), 3.55–3.61 (m, 1H), 1.27 (s, 9H), 1.22 (s, 9H), 1.21 (s, 9H), 1.19 (s, 9H), 1.18 (s, 9H), 1.13 (s, 9H), 1.09 (s, 9H); $^{13}$C NMR (CDCl$_3$, 68 MHz) δ 177.9, 177.7, 177.4, 177.1, 177.0, 176.6, 176.1, 133.4, 132.0, 131.7, 129.3, 129.0, 128.5, 100.3, 86.3, 77.6, 73.5, 72.7, 71.8, 71.5, 70.0, 68.9, 67.0, 62.2, 61.4, 39.1, 39.1, 38.9, 27.6, 27.5, 27.4, 27.3; FABMS C$_{53}$H$_{82}$O$_{17}$S (MNa$^+$) calcd 1045.5170, found 1045.5173.

To a solution of hepta-pivaloyl lactose phenyl thioglycoside 50 (2.0 g, 1.9 mmol) in 60 mL of CH$_2$Cl$_2$ at –78° C. is added 65% m-CPBA (0.546 g, 2.02 mmol). The reaction mixture is allowed to warm to –15° C. and quenched with methyl sulfide (0.3 mL, 4 mmol). The reaction mixture is then diluted with 100 mL of saturated NaHCO$_3$ and extracted with CH$_2$C$_2$ (2×100 mL). The organic layers are combined, dried over Na$_2$SO$_4$, and concentrated in vacuo. The product is purified by flash chromatography (25% EtOAc/hexane) to afford 2.0 g (100%) of the title compound 51 as a mixture of diastereomers: R$_f$0.19 (20% EtOAc/hexane).

7.24. 4-O-(2,3,4,6-tetra-O-pivaloyl-α-D-glucopyranosyl)-2,3,6-tri-O-pivaloyl-1 deoxy-1-phenylsulfinyl-β-D-glucopyranose (53)

By the method above, but beginning with maltose monohydrate (52), the title compound is obtained as a mixture of diastereomers. To a solution of maltose monohydrate 52 (3.5 g, 9.7 mmol) in 40 mL of pyridine at room temperature is added acetic anhydride (20 mL, 210 mmol) and DMAP (0.10 g, 0.82 mmol). The solution is stirred at room temperature for 5 h and concentrated. The residue is dissolved in 200 mL of CH$_2$Cl$_2$, washed with 1N HCl (4×100 mL), dried over Na$_2$SO$_4$, and concentrated to afford 6.6 g (100%) of peracetylated maltose as the β anomer maltose-47: R$_f$0.58 (75% EtOAc/petroleum ether); $^1$H NMR (CDCl$_3$, 270 MHz) δ 5.74 (d, J=8.2 Hz, 1H, H-1), 5.26–5.41 (m, 3H), 4.94–5.09 (m, 2H), 4.86 (dd, J=10.5, 4.0 Hz, 1H), 4.45 (dd, J=12.4, 2.3 Hz, 1H), 4.19–4.27 (m, 2H), 4.0–4.07 (m, 2H), 3.91–3.96 (m, 1H), 3.80–3.87 (m, 1H), 2.14 (s, 3H), 2.10 (s, 6H), 2.05 (s, 3H), 2.03 (s, 3H), 2.01 (s, 6H), 2.00 (s, 3H).

To a solution of peracetylated maltose maltose-47 (6.8 g, 10.0 mmol) in 70 mL of CH$_2$Cl$_2$ is added thiophenol (2.1 mL, 20 mmcl) followed by BF$_3$.Et$_2$O (9.2 mL, 75 mmol). The reaction mixture is stirred at room temperature for 0.5 h, quenched with 100 mL of saturated NaHCO$_3$, and extracted with CH$_2$Cl$_2$ (3×100 mL). Organic layers are combined, dried with Na$_2$SO$_4$, concentrated, and purified by flash chromatography (40% EtOAc/petroleum ether) to afford 6.4 g (88%) of maltose thioglycoside maltose-48 as a 12:1 (β:α) mixture of anomers: R$_f$0.39 (50% EtOAc/petroleum ether); $^1$H NMR (CDCl$_3$, 270 MHz) β-anomer, δ 7.46–7.49 (m, 2H), 7.307.33 (m, 3H), 5.39 (d, J=4.3 Hz, 1H), 5.25–5.35 (m, 2H), 5.04 (appt, J=9.9 Hz, 1H), 4.71–4.87 (m, 3H), 4.54 (dd, J=12.0, 2.5 Hz, 1H), 3.91–4.27 (m, 5H), 3.70–3.75 (m, 1H), 2.13 (s, 3H), 2.10 (s, 3H), 2.07 (s, 3H), 2.04 (s, 3H), 2.03 (s, 3H), 2.00 (s, 3H), 1.99 (s, 3H).

To a solution of maltose thioglycoside maltose-48 (6.4 g, 8.8 mmol) in 100 mL of MeOH is added sodium methoxide (0.950 g, 17.6 mmol). The reaction mixture is stirred at room temperature for 1.5 h, neutralized with Amberlite IR-120 (plus) resin, filtered, washed with MeOH, and concentrated to give the deprotected intermediate maltose-49 which is taken on to the next step without further purification.

To a solution of the intermediate maltose-49 in 75 mL of pyridine is added pivaloyl chloride (32.5 mL, 264 mmol) followed by DMAP (0.10 g, 0.82 mmol). The reaction is heated at 110° C. After 28 h, additional pivaloyl chloride (8.0 mL, 65 mmol) is added, and the reaction mixture is heated at 110° C. for 24 h. The reaction mixture is allowed to cool, poured into 100 mL of MeOH, diluted with 300 mL of EtOAc, washed with H$_2$O (100 mL), 1N HCl (6×100 mL), saturated NaCl (3×100 mL), dried over Na$_2$SO$_4$, and concentrated. The residue is purified by flash chromatography (1–5% EtOAc/petroleum ether) to give 5.6 g (62%) of perpivolated maltose maltose-50 as a 12:1 (β:α) mixture of anomers as a white foam: R$_f$0.38 (10% EtOAc/petroleum ether); $^1$H NMR (CDCl$_3$, 270 MHz) β-anomer, δ 7.47–7.51 (m, 2H), 7.27–7.32 (m, 3H), 5.45 (appt, J=9.7 Hz, 1H), 5.22–5.29 (m, 2H), 5.13 (app t, J=9.72 Hz, 1H), 4.72–4.89 (m, 3H), 4.59 (dd, J=11.7, 2.5 Hz, 1H), 4.23 (dd, J=11.9, 5.9 Hz, 1H), 4.09–4.14 (m, 2H), 4.01 (app t, J=8.9 Hz, 1H), 3.88–3.95 (m, 1H), 3.69–3.74 (m, 1H), 1.26 (S, 9H), 1.23 (s, 9H), 1.21 (s, 9H), 1.19 (s, 9H), 1.16 (s, 9H), 1.15 (s, 9H), 1.11 (s, 9H); $^{13}$C NMR (CDCl$_3$, 68 MHz) δ 178.0, 177.8, 177.4, 177.1, 176.7, 176.6, 176.3, 132.9, 132.6, 132.1, 129.3, 129.1, 128.3, 93.2, 86.4, 76.7, 76.3, 70.5, 70.3, 69.6, 69.3, 68.7, 67.8, 63.1, 61.7, 39.1, 39.0, 38.9, 27.5, 27.4, 27.2, 27.0; FABMS C$_{53}$H$_{82}$O$_{17}$S (MNa$^+$) calcd 1045.5170, found 1045.5121.

To a solution of perpivoated maltose maltose-50 (2.0 g, 1.9 mmol) in 60 mL of CH$_2$Cl$_2$ at –78° C. is added mCPBA (0.54 g, 2.0 mmol, 64%). The reaction is allowed to warm to –15° C., quenched with methyl sulfide (0.3 mL, 4 mmol), diluted with 100 mL of saturated NaHCO$_3$, and extracted with CH$_2$Cl$_2$ (2×100 mL). Organic layers are combined, dried over Na$_2$SO$_4$, concentrated, and purified by flash chromatography (20% EtOAc/petroleum ether) to give 2.0 g (100%) of sulfoxide 53 as a mixture of diastereomers as a white foam: R$_f$0.31 (20% EtOAc/petroleum ether).

7.25. 4-[(3-O-acetyl-2-azido-4,6-O-benzylidine-1,2-dideoxy-α-D-glucosyl)thio]phenoxyacetic acid (64)

To acetic anhydride (100 mL) is added mannose (0.1 g) and concentrated perchloric acid (8 drops). The solution is heated to 30° C. and mannose (24.5 g, 136 mmol) is added in small portions over a period of 2 h while the reaction temperature is kept between 40–45° C. The reaction mixture is allowed to cool and then stirred for 3 h at room temperature to produce crude mannose pentaacetate 54: R$_f$0.31 (50% EtOAc/hexane).

The reaction mixture is cooled at 10° C. and phosphorous tribromide (21.0 mL, 220 mmol) is added. To this solution, water (11 mL, 610 mmol) is added dropwise so that the internal temperature of the reaction mixture is maintained at 20–25° C. After 30 minutes, the addition is complete, and the reaction mixture is stirred at room temperature for 1.5 h.

The reaction mixture is cooled to 5° C. and a solution of sodium acetate trihydrate (74.4 g, 547 mmol) in water (100 mL) is added dropwise over 30 minutes. Initially, the reaction is exothermic until approximately one third of the aqueous sodium acetate solution had been added. During the course of the addition, the temperature of the reaction mixture is maintained at 20–25° C. and then stirred at room temperature for 20 minutes. The reaction mixture is poured onto ice and extracted with CHCl$_3$ (3×120 mL), washed with water (300 mL), saturated NaHCO$_3$ (300 mL), dried over MgSO$_4$, filtered and concentrated to a yellow oil. The product is recrystallized from diethyl ether (200 mL) to afford 11.6 g (24%) of 1,3,4,6-tetra-O-acetyl-β-D-mannopyranose 55 as a white solid: R$_f$0.39 (33% hexane/EtOAc); $^1$H NMR (CDCl$_3$, 270 MHz) d 5.80 (t, J=0.99 Hz, 1H, H-1), 5.39 (app t, J=9.8 Hz, 1H, H-4), 5.05 (ddd, J=9.8, 3.0, 0.99 Hz, 1H, H-3), 4.30 (ddd, J=12.4, 4.9, 0.66, 1H, H-6), 4.20 (br s, 1H, H-2), 4.12 (dd, J=12.5, 2.3 Hz, 1H, H-6), 3.78 (dddd, J=9.7, 4.9, 2.3, 0.99 Hz, 1H, H-5), 2.18 (s, 3H), 2.12 (s, 3H), 2.05 (s, 3H), 2.10 (s, 3H).

To a solution of mannose tetraacetate 55 (1.50 g. 4.30 mmol) in 46 mL of $CH_2Cl_2$ is added pyridine (1.0 mL, 13 mmol). The solution is cooled to $-25°$ C. and trifluoromethanesulfonic anhydride (1.8 mL, 2.98 g, 10.5 mmol) is added dropwise. The reaction mixture is stirred for 45 min at $-25°$ C. and then diluted with 50 mL of $CH_2Cl_2$, washed with $H_2O$ (100 mL), $NaHCO_3$ (100 mL), saturated NaCl (100 mL), dried over $MgSO_4$, filtered, and concentrated to afford an orange gel. The product is recrystallized from diethyl ether (25 mL) to afford 1.59 g (77%) of 1,3,4,6-tetra-O-acetyl-2-O-trifluoromethanesulfonyl-β-D-mannopyranose 56 as a white solid: $R_f$ 0.49 (50% EtOAc/hexane); $^1$H NMR ($CDCl_3$, 300 MHz) δ 5.92 (s, 1H, H-1), 5.15–5.34 (m, 3H), 4.154.28 (m, 2H), 3.81–3.87 (m, 1H, H-5), 2.08 (s, 3H), 2.10 (s, 3H), 2.12 (s, 3H), 2.16 (s,3H).

To a solution of mannose triflate 56 (1.28 g, 2.66 mmol) in 14 mL of DMF is added sodium azide (0.69 g, 10.5 mmol). The reaction mixture is heated at 40° C. for 1.75 h, cooled to room temperature, diluted with 100 mL of $CH_2Cl_2$, washed with $H_2O$ (100 mL), saturated NaCl (100 mL), dried over $MgSO_4$, filtered, and concentrated to afford a yellow oil. The product is purified by flash chromatography (33% EtOAc/hexane) to afford 0.80 g (81%) of 2-azido-2-deoxy-1,3,4,6-tetra-O-acetyl-β-D-glucopyranose 57: $R_f$ 0.31 (33% EtOAc/hexane) δ 5.55 (d, J=8.6 Hz, 1H, H-1), 5.015.15 (m, 2H, H-3, H-4), 4.31 (dd, J=12.7, 4.5 Hz, 1H, H-6), 4.08 (d, J=12.5 Hz, 1H, H-6), 3.77–3.84 (m, 1H, H-5), 3.69 (app t, J=9.1 Hz, 1H, H-2), 2.10 (s, 3H), 2.08 (s, 3H), 2.05 (s, 3H), 2.03 (s, 3H).

To a solution of 2-azido glucose tetraacetate 57 (0.222 g, 0.59 mmol) in 6.6 mL of $CH_2Cl_2$ is added 4-hydroxythiophenol (0.146 g, 1.15 mmol) followed by boron trifluoride diethyl ether complex (15.9 mL, 18.4 g. 141 mmol). The reaction mixture is heated at 45° C. for 12 h and then quenched by the addition of 2 mL of $H_2O$. The reaction mixture is diluted with 25 mL of $CH_2Cl_2$, washed with $H_2O$ (10 mL), saturated NaCl (10 mL), dried over $Na_2SO_4$, filtered, and concentrated to afford 0.232 g of crude 2-azido-1,2-dideoxy-1-(4-hydroxyphenylthio)-3,4,6-tri-O-acetyl-α,β-D-glucopyranose 58 as a yellow oil, a mixture of anomers which is then taken on to the next step without further purification.

To a solution of the thioglycoside anomers 58 in 5.2 mL of methanol is added $K_2CO_3$ (0.146 g, 1.06 mmol). The reaction mixture is stirred at room temperature for 10 min. Amberlite resin (acid form) is added to the reaction mixture and stirred for an additional 15 min. The neutralized mixture is then filtered through Celite, washed several times with methanol, and concentrated to afford 0.512 g of 2-azido-1,2-dideoxy-1-(4-hydroxyphenylthio)-α,β-D-glucopyranose 59. The product is purified by flash chromatography over silica gel (10% MeOH in $CH_2Cl_2$) to afford 0.028 g (15% from 57) as a 2:1 (α,β) mixture of anomers: $R_f$ (α-anomer) 0.33 (10% MeOH/$CH_2Cl_2$); $R_f$ (β-anomer) 0.26 (10% MeOH/$CH_2Cl_2$); $^1$H NMR ($d_6$-acetone, 270 MHz, mixture of anomers) δ 8.69 (br s, 1H), 8.63 (br s, 1H), 7.45 (d, J=8.9 Hz, 2H), 7.40 (d, J=8.6 Hz, 2H), 6.84 (d, J=8.6 Hz, 2H), 6.81 (d, J=8.6 Hz, 2H), 5.36 (d, J=4.6 Hz, 1H), 4.85–4.89 (m, 2H), 4.55 (d, J=5.3 Hz, 1H), 4.40 (d, J=9.2 Hz, 1H), 4.43–4.45 (m, 2H), 4.11–4.18 (m, 1H), 3.42–3.88 (m, 7H), 3.27–3.37 (m, 4H), 3.08 (app t, J=9.7 Hz, 1H).

To a solution of mixed anomers 59 (2.10 g, 6.70 mmol) in 85 mL of THF is added benzaldehyde dimethyl acetal (3.0 mL, 3.10 g, 20.1 mmol) and camphorsulfonic acid (0.31 g, 1.34 mmol). The reaction mixture is stirred at 62° C. for 7 h and then at room temperature for 10 h, cooled and concentrated to afford a brown oil. The product is purified by flash chromatography on silica gel (20% EtOAc/hexane) to afford 1.16 g (43%) of 2-azido-4,6-O-benzylidene-1,2-dideoxy-1-(4-hydroxyphenylthio)-α,β-D-glucopyranose 60 as a mixture of anomers. The anomers are separable by flash chromatography (20% EtOAc/hexane): $R_f$ (α-anomer) 0.31 (40% EtOAc/hexane); $R_f$ (β-anomer) 0.42 (40% EtOAc/hexane); $^1$H NMR ($CDCl_3$, 270 MHz) α-anomer, δ 7.33–7.55 (m, 7H), 6.84 (d, J=8.9 Hz, 2H), 5.64 (s, 1H), 5.49 (d, J=4.6 Hz, 1H, H-1), 4.32 (td, J=9.8, 4.9 Hz, 1H, H-5), 4.16 (dd, J=10.2, 4.9 Hz, 1H, H-6), 3.92–4.03 (m, 2H), 3.77 (app t, J=10.2 Hz, 1H, H-6), 3.63 (app t, J=9.3 Hz, 1H, H-4). The mixed anomers are carried on to the following step without separation.

To a solution of 4,6-benzylidene protected glucose 60 (1.04 g, 2.58 mmol) and 2-(trimethylsilyl)ethyl 2-bromoacetate (1.27 g, 5.16 mmol) in 25 mL of DMF is added $K_2CO_3$ (0.35 g, 2.58 mmol). The reaction mixture is heated at 45° C. for 12 h, cooled, diluted with 50 mL of $CH_2Cl_2$, washed with saturated $NaHCO_3$ (75 mL) and then extracted with $CH_2Cl_2$ (2×50 mL), washed with $H_2O$ (75 mL), saturated NaCl (75 mL), dried over $Na_2SO_4$, filtered and concentrated to afford 5.40 g of the anomers 61 and 62 of 2-(trimethylsilyl)ethyl 2-{4-[(2-azido-4,6-O-benzylidene-1,2-dideoxy-D-glucopyranosyl)thio]phenoxy}acetate. The anomers are separated by flash chromatography (20% EtOAc/hexane) to afford 0.811 g (56%) of α-anomer 61: $R_f$ 0.59 (40% EtOAc/hexane), and 0.496 g (34%) of β-anomer 62: $R_f$ 0.70 (40% EtOAc/hexane); $^1$H NMR ($CDCl_3$, 300 MHz) α-anomer, d 7.28–7.55 (m, 7H), 7.84 (d, J=8.9 Hz, 2H), 5.50 (s, 1H), 5.36 (d, J=5.5 Hz, 1H, H-1), 4.54 (s, 2H), 4.34 (td, J=9.9, 4.7 Hz, 1H, H-5), 4.25 (m, 2H), 4.18 (dd, J=10.4, 4.9 Hz, 1H, H-6), 3.97 (ddd, J=9.9, 9.9, 1.8 Hz, 1H, H-3), 3.83 (dd, J=9.8, 5.5 Hz, 1H, H-2), 3.69 (app t, J=10.2 Hz, 1H, H-6), 3.51 (app t, J=9.3 Hz, 1H, H-4), 2.90 (br s, 1H), :L.0 (m, 2H), 0.50 (s, 9H); $^1$H NMR ($CDCl_3$, 270 MHz) β-anomer, δ 7.33–7.55 (m, 7H), 6.88 (d, J=8.9 Hz, 2H), 5.52 (s, 1H), 4.62 (s, 2H), 4.43 (d, J=10.2 Hz, 1H, H-l), 4.29–4.39 (m, 1H, H-6), 4.32 (m, 2H), 3.72–3.80 (m, 2H), 3.43–3.48 (m, 2H), 3.30 (app t, J=9.7 Hz, 1H, H-2), 1.02–1.07 (m, 2H), 0.50 (s, 9H).

To a solution of 61 (0.848 g, 1.51 mmol) in 15 mL of $CH_2Cl_2$ is added acetic anhydride (0.43 mL, 0.46 g, 4.54 mmol), triethylamine (0.63 mL, 0.46 g, 4.54 mmol), and DMAP (0.187 g, 1.51 mmol). The reaction is stirred at room temperature for 5 min and then diluted with 10 mL of $CH_2Cl_2$, washed with $NaHCO_3$ (15 mL), extracted with $CH_2Cl_2$ (2×15 mL), washed with saturated NaCl (20 mL), dried over $Na_2SO_4$, filtered and concentrated to afford 1.07 g of a yellow-orange oil. The product is purified by flash chromatography (17% EtOAc/hexane) to afford 0.660 g (73%) of 2-(trimethylsilyl)ethyl 2-{4-[(3-O-acetyl-2-azido-4,6-O-benzylidene-1,2-dideoxy-α-D-glucopyranosyl)thio]phenoxy}acetate 63: $R_f$ 0.18 (17% EtOAc/hexane); $^1$H NMR ($CDCl_3$, 270 MHz) δ 7.29–7.43 (m, 7H), 6.81 (d, J=8.9 Hz, 2H), 5.39–5.46 (m, 3H), 4.44 (td, J=9.9, 4.9 Hz, 1H, H-5), 4.24 (m, 2H), 4.18 (dd, J=10.2, 4.9 Hz, 1H, H-6), 3.96 (dd, J=10.2, 5.6 Hz, 1H, H-2), 3.71 (app t, J=10.2 Hz, 1H, H-6), 3.60 (app t, J=9.6 Hz, 1H, H-4), 2.11 (s, 3H), 1.0 (m, 2H), 0.87 (s, 9H).

To a solution of 63 (0.044 g, 0.073 mmol) in 0.4 mL of THF is added tetra-n-butylammonium fluoride solution (1.0M in THF, 0.36 mL, 0.36 mmol). The reaction mixture is stirred for 20 min at room temperature and diluted with 3 mL of $CH_2Cl_2$, washed with 5% HCl (5 mL), extracted with $CH_2Cl_2$ (2×2 mL), washed with saturated NaCl (5 mL), dried over $Na_2SO_4$, filtered, and concentrated to afford 0.067 g of a clear oil. The product is purified by flash chromatography (2% MeOH/CHCl$_3$) to afford 0.035 g (95%) of 2-{4-[(3-O-acetyl-2-azido-4,6-O-benzylidene-1,2-dideoxy-α-D-glucopyranosyl)thio]phenoxy}acetic acid 64 as a white solid: R$_f$0.39 (5% MeOH/CHCl$_3$); $^1$H NMR (CDCl$_3$, 270 MHz) δ 7.35–7.49 (m, 7H), 6.90 (d, J=8.9 Hz, 2H), 5.45–5.52 (m, 3H), 4.69 (s, 2H), 4.48 (td, J=9.8, 5.2 Hz, 1H, H-5), 4.24 (dd, J=10.4, 4.7 Hz, 1H, H-6), 4.03 (dd, J=10.2, 5.6 Hz, 1H, H-2), 3.78 (app t, J=10.3 Hz, 1H, H-6). 3.67 (app t, J=9.6 Hz, 1H, H-4), 2.15 (s, 3H). FABMS C$_{23}$H$_{23}$O$_8$N$_3$S calcd 524.1104, found 524.1118.

7.26. 2-{4-[(3-O-acetyl-2-azido-4,6-O-benzylidine-1,2-dideoxy-β-D-glucosyl)thio]-phenoxy}acetic acid (66)

To a solution of 62 (0.496 g, 0.886 mmol) in 10 m,nL of CH$_2$Cl$_2$ is added acetic anhydride (0.25 mL, 0.27 g, 2.65 mmol), triethylamine (0.37 mL, 0.27 g, 2.65 mmol), and DMAP (0.108 g, 0.886 mmol). The reaction is stirred at room temperature for 20 min and then diluted with 3 mL of CH$_2$Cl$_2$, washed with NaHCO$_3$ (10 mL), extracted with CH$_2$Cl$_2$ (2×3 mL), washed with saturated NaCl (5 mL), dried over Na$_2$SO$_4$, filtered and concentrated to afford 0.612 g of a yellow oil. The product is purified by flash chromatography (17% EtOAc/hexane) to afford 0.438 g (82%) of 2-(trimethylsilyl)ethyl 2-{4-[(3-O-acetyl-2-azido-4,6-O-benzylidene-1,2-dideoxy-β-D-glucopyranosyl)thio]-phenoxy}acetate 65: R$_f$0.56 (40% EtOAc/hexane); $^1$H NMR (CDCl$_3$, 300 MHz) δ 7.27–7.55 (m, 7H), 6.85 (d, J=8.8 Hz, 2H), 5.41 (s, 1H), 5.17 (app t, J=9.4 Hz, 1H, H-3), 4.57 (s, 2H), 4.43 (d, J=10.3 Hz, 1H, H-1), 4.30–4.34 (m, 1H), 4.26 (m, 2H), 3.70 (ddd, J=10.3, 9.9, 2.7 Hz, 1H, H-5), 3.40–3.49 (m, 2H, H-4, H-6), 3.29 (app t, J=9.7 Hz, 1H, H-2), 2.24 (s, 3H), 0.99 (m, 2H), 0.01 (s, 9H)

To a solution of 65 (0.425 g, 0.706 mmol) in 7 mL of THF is added tetra-n-butylammonium fluoride solution (1.0M in THF, 3.5 mL, 3.53 mmol). The reaction mixture is stirred for 5 min at room temperature and diluted with 10 mL of CH$_2$Cl$_2$, washed with 5% HCl (10 mL), extracted with CH$_2$Cl$_2$ (2×5 mL), washed with saturated NaCl (10 mL), dried over Na$_2$SO$_4$, filtered, and concentrated to afford 0.65 g of a clear oil. The product is purified by flash chromatography (gradient elution: 50% EtOAc/hexane, 100% EtOAc, 20% MeOH/CHCl$_3$) to afford 0.30 g (85%) of the title compound 66 as a white solid: R$_f$0.48 (5% MeOH/CHCl$_3$); $^1$H NMR (C$_6$D$_6$, 300 MHz) δ 7.34–7.62 (m, 7H), 7.05 (d, J=8.8 Hz, 2H), 5.67 (s, 1H), 5.34 (app t, J=9.3 Hz, 1H, H-3), 4.92 (d, J=10.3 Hz, 1H, H-1), 4.77 (s, 2H), 4.36 (dd, J=9.3, 3.5 Hz, 1H), 3.70–3.90 (m, 3H), 3.52 (app t, J=9.9 Hz, 1H, H-2), 2.05 (s, 3H); $^{13}$C NMR (CD$_3$OD, 68 MHz) δ 171.3, 160.1, 138.5, 137.2, 129.8, 128.9, 127.1, 122.7, 116.2, 102.4, 87.5, 79.3, 74.3, 71.4, 69.1, 65.2, 64.5, 20.6; FABMS C$_{23}$H$_{23}$O$_8$N$_3$S (MNa$^+$) calcd 524.1104, found 524.1134.

7.27. 2-{4-[(3-O-acetyl-2-azido-4,6-O-benzylidene-1,2-dideoxy-β-D-galactopyranosyl)thio]phenoxy}acetic acid (76)

To a solution of tri-O-acetyl-D-galactal 67 (25.0 g, 91.8 mmol) in 1000 mL of distilled CH$_3$CN at −20° C. is added sodium azide (8.96 g, 138 mmol), followed by ceric ammonium nitrate (151 g, 276 mmol). The reaction suspension is stirred vigorously at −15 to −20° C. for 24 h and then filtered through Celite. The filtrate is diluted with 1000 mL of ice water and extracted with CH$_2$Cl$_2$ (3×200 mL). The combined organic layers are dried over Na$_2$SO$_4$, concentrated, and purified by flash chromatography (10% EtOAc/hexane) to give 17.5 g (51%) of 2-azido-2-deoxy-1-O-nitro-3,4,6-tri-O-acetyl-α,β-D-galactopyranose 68 as a mixture of anomers: R$_f$0.26 (25% EtOAc/hexane); $^1$H NMR (CDCl$_3$, 270 MHz, mixture of anomers) δ 6.32 (d, J=4.0 Hz, 1 H, H-1α), 5.55 (d, J=8.9 Hz, 1 H, H-1β), 5.48 (d, J=3.0 Hz, 1 H, H-4α), 5.37 (d, J=3.0 Hz, 1 H, H-4β), 5.23 (dd, J=11.6, 3.3 Hz, 1 H, H-3α), 4.93 (dd, J=10.6, 3.3 Hz, 1 H, H-3β), 4.35 (t, J=6.6 Hz, 1 H, H-5α), 3.9–4.2 (m, 6 H, H-2α, H-5β, H-6β, H-6α), 3.81 (dd, J=10.6, 8.9 Hz, 1 H, H-2β), 1.95–2.25 (6s,18 H).

To a solution of nitrate ester 68 (17.5 g, 46.5 mmol) in 500 mL of glacial acetic acid is added sodium acetate (7.63 g, 93.0 mmol). The solution is stirred at 100° C. for 3 h and then allowed to cool to room temperature. The reaction mixture is diluted with 1000 mL of ice water and extracted with CH$_2$Cl$_2$ (2×200 mL) The organic layers are combined and washed with ice water (2×400 mL), saturated NaHCO$_3$ (400 mL), saturated NaCl (400 mL), dried over Na$_2$SO$_4$, filtered and concentrated. The crude product is crystallized from hexane/EtOAc to give 7.2 g of 2-azido-2-deoxy-1,3,4,6-tetra-O-acetyl-α,β-D-galactopyranose 69 (mixed anomers). The mother liquors from the crystallization are concentrated and purified by flash chromatography (25% EtOAc/hexane) to give an additional 7.0 g of the product (14.2 g, 81.7% in total) as a mixture of anomers: R$_f$0.3 (30% EtOAc/hexane); $^1$H NMR (CDCl$_3$, 270 MHz, mixture of anomers) δ 6.26 (d, J=3.6 Hz, 1 H, H-1α), 5.50 (d, J=8.6 Hz, 1 H, H-1β), 5.42 (d, J=3.0 Hz, 1 H, H-4α), 5.32 (d, J=3.0 Hz, 1 H, H-4β), 5.25 (dd, J=11.2, 3.0 Hz, 1 H, H-3α), 4.85 (dd, J=10.6, 3.3 Hz, 1 H, H-3β), 4.23 (t, J=6.6 Hz, 1 H, H-5α), 3.95–4.10 (m, 5 H, H-6α, H-5β, H-6β), 3.88 (dd, J=11.2, 3.6 Hz, 1 H, H-2α), 3.78 (dd, J=10.9, 8.6 Hz, 1 H, H-2β), 1.90–2.20 (6s, 24 H, OAc).

To a solution of 69 (1.16 g, 2.95 mmol) in 100 mL of CH$_2$Cl$_2$ is added 4-hydroxythiophenol (0.90 g, 5.9 mmol), followed by boron trifluoride diethyl ether complex (1.5 mL, 11.8 mmol). The mixture is refluxed at 50° C. for 48 h and then quenched by the addition of 200 mL of H$_2$O. The reaction mixture is diluted with 200 mL of CH$_2$Cl$_2$. The organic layer is washed with H$_2$O (200 mL), saturated NaHCO$_3$ (2×200 mL), dried over Na$_2$SO$_4$, filtered, and concentrated to give 2-azido-1,2-dideoxy-1-(4-hydroxyphenylthio)-3,4,6-tri-O-α,β-D-galactopyranose 70 as a brown oil, R$_f$0.13 (30% EtOAc/hexane, which is taken on to the next reaction without further purification. A purified sample of the β-anomer had $^1$H NMR (CDCl$_3$, 270 MHz) δ 7.51 (d, J=8.9 Hz, 2 H, ArH), 6.82 (d, J=8.9 Hz, 2 H, ArH), 5.33 (dd, J=3.3, 1.0 Hz, 1 H, H-4), 5.08 (s, 1 H, ArOH), 4.85 (dd, J=10.2, 3.3 Hz, 1 H, H-3), 4.24 (d, J=10.2 Hz, 1 H, H-1), 4.17 (dd, J=11.2, 6.6 Hz, 1 H, H-6), 4.09 (dd, J=11.2, 6.6 Hz, 1 H, H-6'), 3.85 (dt, J=6.6, 1.0 Hz, 1 H, H-5), 3.57 (t, J=10.2 Hz, 1 H, H-2), 2.08 (s, 3 H, OAc), 2.04 (s, 3 H, OAc), 2.03 (s, 3 H, OAc).

To a solution of 70 in 50 mL of MeOH is added K$_2$CO$_3$ until pH paper indicated the solution to be basic (pH 11). The reaction mixture is stirred at room temperature for 15 min and then neutralized with Amberlite resin (acid form). The resin is removed by filtration and washed with MeOH (2×50 mL). The filtrates are concentrated and purified by flash chromatography (70% EtOAc/hexane) to give 0.65 g (63%) of 2-azido-1,2-dideoxy-1-(4-hydroxyphenylthio)-α,β-D-galactopyranose 71: R$_f$0.19 (100% EtOAc).

To a solution of 71 (1.20 g, 3.65 mmol) in 100 mL of DMF is added benzaldehyde dimethyl acetal (1.65 mL, 10.9 mmol) and p-toluenesulfonic acid (0.14 g, 0.73 mmol). The reaction is stirred at room temperature for 8 h and then neutralized with saturated NaHCO$_3$. The reaction mixture is diluted with 200 mL of EtOAc, washed with saturated NaCl (3×200 mL), dried over Na$_2$SO$_4$, filtered, concentrated and purified by flash chromatography (35% EtOAc/hexane) to give 1.30 g (89%) of 2-azido-4,6-O-benzylidene-1,2-dideoxy-1-(4-hydroxyphenylthio)-α,β-D-galactopyranose 72. The mixed anomers are used directly for the next step, although the anomers are separable by flash chromatography (35% EtOAc/hexane): $R_f$ (α-anomer) 0.28 (40% EtOAc/hexane); $R_f$ (β-anomer) 0.11 (40% EtOAc/hexane); $^1$H NMR (CDCl$_3$, 270 MHz) β-anomer, δ 7.61 (d, J=8.6 Hz, 2 H, ArH), 7.37–7.39 (m, 5 H, ArH), 6.76 (d, J=8.6 Hz, 2 H, ArH), 5.51 (s, 1 H, CH), 4.96 (s, 1 H, ArOH), 4.38 (dd, J=12.5, 1.7 Hz, 1 H, H-6), 4.32 (d, J=9.6 Hz, 1 H, H-1), 4.17 (d, J=3.6 Hz, 1 H, H-4), 4.02 (dd, J=12.5, 1.7 Hz, 1 H, H-6'), 3.65 (dt, J=9.6, 3.6 Hz, 1 H, H-3), 3.51 (d, J=1.3 Hz, 1 H, H-5), 3.45 (t, J=9.6 Hz, 1 H, H-2), 2.50 (d, J=9.9 Hz, 1 H, OH-3); α-anomer, δ 7.36–7.50 (m, 7 H, ArH), 6.77–6.80 (m, 2 H, ArH), 5.61 (s, 1 H, CH), 5.57 (d, J=5.3 Hz, 1 H, H-1), 4.82 (s, 1 H, ArOH), 4.34 (dd, J=3.6, 1.0 Hz, 1 H, H-4), 4.30 (d, J=1.0 Hz, 1 H, H-5), 4.11–4.30 (m, 3 H, H-6, H-6'), 4.17 (dd, J=10.2, 5.3 Hz, 1 H, H-2), 4.00 (dt, J=10.2, 3.6 Hz, 1 H, H-3), 2.52 (d, J=10.2 Hz, 1 H, OH-3).

To a solution of 72 (1.70 g, 4.20 mmol) in 60 mL of DMF is added K$_2$CO$_3$ (0.58 g, 4.2 mmol) and 2-(trimethylsilyl) ethyl bromoacetate (2.0 g, 8.5 mmol). The reaction mixture is stirred at 50–60° C. for 3 h and then allowed to cool to room temperature. The reaction mixture is diluted with EtOAc (150 mL), washed with H$_2$O (3×80 mL) and saturated NaCl (80 mL), dried over Na$_2$SO$_4$, concentrated and purified by flash chromatography (45% EtOAc/hexane) to give 1.60 g (68%) of 2-(trimethylsilyl)ethyl 2-{4-[(2-azido-4,6-O-benzylidene-1,2-dideoxy-α,β-D-galactopyranosyl) thio]-phenoxy}acetate 73 as a mixture of anomers. The mixed anomers are used directly for the next step, but could be separated by flash chromatography (25% EtOAc/hexane to elute the α-anomer, 45% EtOAc/hexane to elute the β-anomer): $R_f$ (α-anomer) 0.15 (25% EtOAc/hexane); $R_f$ (β-anomer) 0.12 (35% EtOAc/hexane); $^1$H NMR (CDCl$_3$, 270 MHz) α-anomer, δ 7.38–7.48 (m, 7 H, ArH), 6.86 (d, J=8.8 Hz, 2 H, ArH), 5.61 (s, 1 H, CH), 5.59 (d, J=5.5 Hz, 1 H, H-1), 4.59 (s, 2 H, OCH$_2$CO), 3.96–4.33 (m, 8 H, H-2, H-3, H-4, H-5, H-6, H-6', COOCH$_2$), 1.06 (t, J=8.8 Hz, 2 H, CH$_2$TMS), 0.05 (s, 9 H, SiMe$_3$); β-anomer, δ 7.66 (d, J=8.8 Hz, 2 H, ArH), 7.39 (s, 5 H, ArH), 6.82 (d, J=9.2 Hz, 2 H, ArH), 5.52 (s, 1 H, CH), 4.55 (s, 2 H, OCH$_2$CO), 4.28–4.39 (m, 5 H, H-1, H-3, H-6, COOCH$_2$), 4.16 (d, J=3.3 Hz, 1 H, H-4), 4.02 ( d, J=12.5 Hz, 1 H, H-6'), 3.49 (s, 1 H, H-5), 3.45 (t, J=9.9 Hz, 1 H, H-2), 1.04 (t, J=8.8 Hz, 2 H, CH$_2$TMS) 0.05 (s, 9 H, SiMe$_3$).

To a solution of 73 (1.60 g, 2.86 mmol) in 50 mL of CH$_2$Cl$_2$ is added Et$_3$N (0.8 mL, 2.86 mmol), acetic anhydride (0.6 mL, 5.72 mmol) and DMAP (0.35 g, 2.86 mmol). The reaction mixture is stirred at room temperature for 15 min. The reaction is diluted with 100 mL of CH$_2$Cl$_2$ and washed with saturated NaHCO$_3$ (80 mL), dried over Na$_2$SO$_4$, filtered, concentrated and purified by flash chromatography to give a combined yield of 1.31 g (76.4%) of the anomers of 2-(trimethylsilyl)ethyl 2-{4-[(3-O-acetyl-2-azido-4,6-O-benzylidene-1,2-dideoxy-α,β-D-galactopyranosyl)thio]-phenoxy}acetate (15% EtOAc/hexane to elute the α-anomer 75, 35% EtOAc/hexane to elute the β-anomer 74)

74: $R_f$ 0.31 (30% EtOAc/hexane); $^1$H NMR (CDCl$_3$, 270 MHz), δ 7.65 (d, J=8.8 Hz, 2 H, ArH), 7.39 (s, 5 H, ArH), 6.77 (d, J=8.8 Hz, 2 H, ArH), 5.47 (s, 1 H, CH), 4.80 (dd, J=10.6, 3.3 Hz, 1 H, H-3), 4.52 (s, 2 H, OCH$_2$CO), 4.42 (d, J=9.9 Hz, 1 H, H-1), 4.36 (d, J=12.1 Hz, 1 H, H-6), 4.31 (t, J=8.8, 8.4 Hz, 2 H, COOCH$_2$), 4.29–4.31 (m, 1 H, H-4), 4.00 (d, J=12.8 Hz, 1 H, H-6'), 3.76 (t, J=10.6, 9.9 Hz, 1 H, H-2), 3.54 (s, 1 H, H-5), 2.10 (s, 3 H, OAc), 1.04 (t, J=8.8, 8.4 Hz, 2 H, CH$_2$TMS), 0.06 (s, 9 H, SiMe$_3$);

75: $R_f$ 0.38 (25% EtOAc/hexane); $^1$H NMR (CDCl$_3$, 270 MHz), δ 7.33–7.49 (m, 5 H, ArH), 7.39 (d, J=8.9 Hz, 2 H, ArH), 6.83 (d, J=8.9 Hz, 2 H, ArH), 5.61 (d, J=5.3 Hz, 1 H, H-1), 5.52 (s, 1 H, CH), 5.01 (dd, J=11.2, 3.6 Hz, 1 H, H-3), 4.56 (s, 2 H, OCH$_2$CO), 4.49–4.55 (m, 2 H, H-2, H-4), 4.28 (m, 2 H, COOCH$_2$), 4.24 (br s, 1 H, H-5), 4.18-(dd, J=12.5, 1.3 Hz, 1 H, H-6) 4.07 (dd, J=12.5, 1.3 Hz, 1 H, H-6'), 2.14 (s, 3 H, OAc), 1.01 (m, 2 H, CH$_2$TMS), 0.03 (s, 9 H, SiMe$_3$); $^{13}$C NMR (CDCl$_3$, 270 MHz), δ 170.4, 168.8, 158.0, 137.5, 134.3, 129.2, 128.3, 126.2, 124.9, 115.6, 100.9, 88.3, 73.3, 71.4, 69.2, 65.6, 64.0, 63.4, 57.9, 21.1, 17.5, 1.35.

To a solution of 74 (0.628 g, 1.04 mmol) in 10 mL of THF is added tetra-n-butylammonium fluoride (2.1 mL of 1.0M solution in THF, 2.09 mmol). The reaction mixture is stirred at room temperature for 10 min and then neutralized with dilute HCl, concentrated and purified by flash chromatography (0.1% HOAc, 5% MeOH, in EtOAc) to give 0.486 g (93%) of the title compound 76: $R_f$ 0.14 (10% MeOH/EtOAc); $^1$H NMR (CDCl$_3$, 270 MHz) δ 7.64 (d, J=8.6 Hz, 2 H, ArH), 7.37 (s, 5 H, ArH), 6.73 (d, J=8.9 Hz, 2 H, ArH), 5.45 (s, 1 H, CH), 4.81 (dd, J=10.2, 3.0 Hz, 1 H, H-3), 4.53 (s, 2 H, OCH$_2$CO), 4.42 (d, J=9.9 Hz, 1 H, H-1), 4.33 (d, J=11.9 Hz, 1 H, H-6), 4.28 (d, J=3.0 Hz, 1 H, H-4), 3.96 (d, J=11.9 Hz, 1 H, H-6'), 3.75 (t, J=10.2, 9.9 Hz, 1 H, H-2), 3.50 (s, 1 H, H-5), 2.08 (s, 3 H, OAc). $^{13}$C NMR (CDCl$_3$, 270 MHz) δ 173.4, 170.7, 158.2, 137.6, 136.6, 129.3, 128.3, 126.4, 121.9, 115.3, 100.7, 85.3, 74.0, 72.7, 69.5, 69.2, 64.8, 58.3, 21.1.

7.28. 2-{4-[(3-O-acetyl-2-azido-4,6-O-benzylidene-1,2-dideoxy-α-D-galactopyranosyl)thio]phenoxy}acetic acid (77)

The title compound is prepared from 75 by treatment with tetrabutylammonium fluoride, and purified by flash chromatography, as described above: $R_f$ 0.14 (30% MeOH/EtOAc); $^1$H NMR (CDCl$_3$, 270 MHz) δ 7.44–7.48 (m, 2 H, ArH), 7.33–7.38 (m, 5 H, ArH), 6.80 (d, J=8.6 Hz, 2 H, ArH), 5.61 (d, J=4.9 Hz, 1 H, H-1), 5.49 (s, 1 H, CH), 4.48–4.56 (m, 4 H, H-2, H-4, OCH$_2$CO), 5.10 (dd, J=10.9, 3.3 Hz, 1 H, H-3), 4.21 (s, 1 H, H-5), 4.14 (d, J=12.9 Hz, 1 H, H-6), 4.04 (d, J=12.2 Hz, 1 H, H-6'), 2.16 (s, 3 H, OAc). $^{13}$C NMR (CDCl$_3$, 270 MHz) δ 173.9, 170.6, 157.7, 137.5, 134.5, 129.3, 128.3, 126.3, 125.2, 115.7, 100.9, 88.2, 73.3, 71.5, 69.2, 65.3, 63.5, 57.9, 21.1.

7.29. 2-{4-[(3-O-acetyl-4-azido-2,6-bis-O-(4-methoxybenzyl)-1,4-dideoxy-β-D-glucopyranosyl)thio]phenoxy}acetic acid (88)

To a solution of galactose pentaacetate (3.30 g, 8.50 mmol) and 4-hydroxy-thiophenol (1.40 g, 11.1 mmol) in 50 mL of methylene chloride at −78° C. is added boron trifluoride diethyl ether complex (2.10 mL, 17.1 mmol ). The solution is allowed to warm slowly to 0° C. and then stirred for an additional hour at 0° C. The mixture is poured into saturated aqueous NaHCO$_3$ (200 mL) and extracted with CH$_2$Cl$_2$ (2×150 mL), dried over Na$_2$SO$_4$, concentrated, and purified by flash chromatography (50% EtOAc/hexane) to give 3.90 g (99%) of 1-deoxy-1-(4-hydroxyphenylthio)-2,3,4,6-tetra-O-acetyl-β-D-galactopyranose 78 as a white solid: $R_f$ 0.3 (50% EtOAc/hexane); $^1$H NMR (CDCl$_3$, 300 MHz) δ 7.42 (d, J=8.6 Hz, 2H), 6.79 (d, J=8.6 Hz, 2H), 5.78 (br s, 1H), 5.39 (d, J=2.56 Hz, 1H, H-4), 5.15 (t, J=9.9 Hz, 1H, H-2), 5.00 (dd, J=3.3, 9.9 Hz, 1H, H-3), 4.56 (d, J=9.9 Hz, 1H, H-1), 4.19 (dd, J=6.6, 11.0 Hz, 1H), 4.09 (dd, J=6.6, 11.0 Hz, 1H), 3.89 (t, J=6.6 Hz, 1H, H-5), 2.12 (s, 3H, OAc), 2.09 (s, 3H, OAc), 2.05 (s, 3H, OAc), 1.97 (s, 3H, OAc).

To a solution of thioglycoside 78 (1.40 g, 3.10 mmol) in 15 mL of methylene chloride is added N,N-diisopropylethylamine (0.64 mL, 3.70 mmol), followed by 2-(trimethylsilyl)ethoxymethyl chloride (0.60 mL, 3.40 mmol). The mixture is stirred at room temperature for 2 h, poured into saturated NaCl (50 mL) and extracted with $CH_2Cl_2$ (2×50 mL), dried over $Na_2SO_4$, concentrated, and purified by flash chromatography (40% EtOAc/hexane) to give 1.60 g (89%) of 1-deoxy-1-{4-[2(trimethylsilyl)ethoxymethoxy]phenylthio}-2,3,4,6-tetra-O-acetyl-β-D-galactopyranose 79 as a colorless oil: $R_f$ 0.4 (33% EtOAc/hexane); $^1$H NMR (CDCl$_3$, 270 MHz) δ 7.46 (d, J=8.4 Hz, 2H), 6.98 (d, J=8.4 Hz, 2H), 5.40 (d, J=3.3 Hz, 1H, H-4), 5.22 (s, 2H, SEM), 5.20 (dd, J=9.9, 9.9 Hz, 1H, H-2), 5.02 (dd, J=3.3, 9.9 Hz, 1H, H-3), 4.58 (d, J=9.9 Hz, 1H, H-1), 4.18 (dd, J=6.6, 11.2 Hz, 1H), 4.10 (dd, J=6.6, 11.2 Hz, 1H), 3.89 (dd, J=6.6, 6.6 Hz, 1H, H-5), 3.75 (t, J=8.4 Hz, 2H, SEM), 2.11 (s, 3H, OAc), 2.10 (s, 3H, OAc), 2.04 (s, 3H, OAc), 1.98 (s, 3H, OAc), 0.94 (t, J=8.4 Hz, 2H, $CH_2$—TMS), 0.01 (s, 9H, SiMe$_3$).

To a solution of the SEM protected thioglycoside 79 (1.60 g, 2.73 mmol) in 15 mL of methanol is added sodium methoxide (300 mg, 5.56 mmol). The mixture is stirred at room temperature for 12 h, then neutralized with Amberlite resin (acid form), filtered, concentrated and run through a short column of silica gel (10% MeOH/EtOAc) to provide crude 1-deoxy-1-{4-[2-(trimethylsilyl)ethoxymethoxy]phenylthio}-β-D-galactopyranose 80 as an oil: $R_f$ 0.15 (EtOAc). The material is taken up in 10 mL of DMF, and dimethoxypropane (0.59 mL, 4.8 mmol), and p-toluenesulfonic acid hydrate (90 mg, 0.48 mmol) are added. The mixture is stirred at room temperature for 12 h, pyridine (0.04 mL, 0.48 mmol) is added, and the reaction mixture is concentrated and purified by flash chromatography (60% EtOAc/hexane) to give 0.5 g (41%) of 1-deoxy-3,4-O-isopropylidene-1-{4-[2-(trimethylsilyl)ethoxymethoxy]phenylthio}-β-D-galactopyranose 81 as a colorless oil: $R_f$ 0.5 (67% EtOAc/hexane); $^1$H NMR (CDCl$_3$, 300 MHz) δ 7.48 (d, J=8.6 Hz, 2H), 6.99 (d, J=8.6 Hz, 2H), 5.21 (s, 2H, SEM), 4.35 (d, J=10.2 Hz, 1H, H-1), 4.17 (dd, J=1.7, 5.4 Hz, 1H), 4.09 (dd, J=6.5 Hz, 1H), 3.94 (m, 1H), 3.85 (m, 2H), 3.73 (t, J=8.1 Hz, 2H, SEM), 3.52 (m, 1H), 2.49 (d, J=1.8 Hz, 1H), 2.17 (d, J=9.1 Hz, 1H), 1.40 (s, 3H, Me), 1.33 (s, 3H, Me), 0.93 (t, J=8.1 Hz, 2H, $CH_2$—TMS), 0.01 (s, 9H, SiMe$_3$).

To a solution of acetonide 81 (80 mg, 0.175 mmol) in 3 mL of DMF is added tetrabutylammonium iodide (194 mg, 0.52 mmol), 4-methoxybenzyl choride (0.19 mL, 1.40 mmol), and a 95% dispersion of sodium hydride (11 mg, 0.44 mmol). The mixture is stirred at room temperature for 1 h, then poured into saturated NaHCO$_3$ (30 mL) and extracted with CH$_2$Cl$_2$ (2×30 mL), dried over Na$_2$SO$_4$, concentrated, and purified by flash chromatography (25% EtOAc/hexane) to give 98 mg (87%) of 2,6-bis-O-(4-methoxybenzyl)-1-deoxy-3,4-O-isopropylidene-1-{4-[2-(trimethylsilyl)ethoxymethoxy]phenylthio}-β-D-galactopyranose 82 as a colorless oil: $R_f$ 0.4 (25% EtOAc/hexane); $^1$H NMR (CDCl$_3$, 270 MHz,) δ 7.50 (d, J=8.6 Hz, 2H), 7.36 (d, J=8.6 Hz, 2H), 7.24 (d, J=9.6 Hz, 2H), 6.89 (m, 6H), 5.17 (s, 2H, SEM), 4.75 (d, J=10.9 Hz, 1H, PMB), 4.62 (d, J=10.9 Hz, 1H, PMB), 4.51 (d, J=11.2 Hz, 1H, PMB), 4.49 (d, J=9.5 Hz, 1H, H-1), 4.44 (d, J=11.2 Hz, 1H, PMB), 4.22 (t, J=5.6 Hz, 1H, H-3), 4.17 (dd, J=5.6, 1.7 Hz, 1H, H-4), 3.83 (dt, J=1.7, 6.0 Hz, 1H, H-5), 3.81 (s, 6H, 2X-OMe), 3.73 (m, 4H), 3.45 (dd, J=5.6, 9.7 Hz, 1H, H-2), 1.41 (s, 3H, C—CH$_3$), 1.34 (s, 3H, C—CH$_3$), 0.94 (t, J=8.4 Hz, 2H, $CH_2$—TMS), 0.01 (s, 9H, SiMe$_3$).

To a solution of 82 (53 mg, 0.082 mmol) in 4 mL of MeOH is added p-toluenesulfonic acid hydrate (3 mg, 0.016 mmol). The mixture is stirred at room temperature for 9 h, neutralized with pyridine (2 drops), concentrated, and purified by flash chromatography (60% EtOAc/hexane) to give 35 mg (81%) of 2,6-bis-O-(4-methoxybenzyl)-1-deoxy-1-(4-hydroxyphenylthio)-β-D-galactopyranose 83 as a colorless oil: $R_f$ 0.4 (60% EtOAc/hexane); $^1$H NMR (CDCl$_3$, 270 MHz) δ 7.46 (d, J=8.6 Hz, 2H), 7.34 (d, J=8.6 Hz, 2H), 7.24 (d, J=8.6 Hz, 2H), 6.87 (m, 4H), 6.68 (d, J=8.2 Hz, 2H), 5.65 (br s, 1H), 4.88 (d, J=10.9 Hz, 1H, PMB), 4.63 (d, J=10.9 Hz, 1H, PMB), 4.49 (s, 2H, PMB), 4.46 (d, J=9.9 Hz, 1H, H-1), 3.99 (d, J=2.3 Hz, 1H, H-4), 3.80 (s, 6H, 2X-OMe), 3.74 (d, J=5.3 Hz, 2H), 3.56 (m, 2H), 3.53 (t, J=8.9 Hz, 1H), 2.80 (br s, 1H), 2.50 (br s, 1H).

To a solution of 83 (35 mg, 0.066 mmol) in 4 mL of DMF is added K$_2$CO$_3$ (15 mg, 0.11 mmol) and 2-(trimethylsilyl)ethyl bromoacetate (25 mg, 0.10 mmol). The reaction is stirred at 45–50° C. for 3 h, concentrated in vacuo and purified by flash chromatography (60% EtOAc/hexane) to give 35 mg (89%) of 2-(trimethylsilyl)ethyl 2-{4-[(2,6-bis-O-(4-methoxybenzyl)-1-deoxy-β-D-galactopyranosyl)thio]-phenoxy}acetate 84 as a colorless oil: $R_f$ 0.5 (60% EtOAc/hexane); $^1$H NMR (CDCl$_3$, 270 MHz) δ 7.53 (d, J=8.6 Hz, 2H), 7.33 (d, J=8.6 Hz, 2H), 7.23 (d, J=8.6 Hz, 2H), 6.87 (m, 4H), 6.79 (d, J=8.6 Hz, 2H), 4.87 (d, J=10.6 Hz, 1H), 4.63 (d, J=10.6 Hz, 1H), 4.56 (s, 2H), 4.49 (s, 2H), 4.48 (d, J=8.9 Hz, 1H, H-1), 4.30 (m, 2H), 3.81 (s, 6H), 3.74 (dd, J=2.0, 5.0 Hz, 1H), 3.57 (m, 2H), 3.53 (dd, J=8.9, 8.9 Hz, 1H), 2.69 (br s, 1H), 2.40 (br s, 1H), 1.03 (m, 2H, $CH_2$—TMS), 0.01 (s, 9H, SiMe$_3$)

To a solution of 84 (141 mg, 0.205 mmol) in 10 mL of CH$_2$Cl$_2$ at −78° C. is added N,N-diisopropylethylamine (0.090 mL, 0.51 mmol), acetic anhydride (0.021 mL, 0.23 mmol) and DMAP (4 mg, 0.03 mmol). The solution is stirred at −78° C. for 30 min, then diluted with 25 mL of EtOAc and washed with saturated NH$_4$Cl (25 mL) and saturated NaHCO$_3$ (25 mL). The aqueous layers are back-extracted with EtOAc (25 mL). The organic layers are combined, dried over Na$_2$SO$_4$, concentrated and purified by flash chromatography (45% EtOAc/hexane) to give 125 mg (83%) of 2-(trimethylsilyl)ethyl 2-{4-[(3-O-acetyl-2,6-bis-O-(4-methoxybenzyl)-1-deoxy-β-D-galactopyranosyl)thio]phenoxy}acetate 85 as a colorless oil: $R_f$ 0.5 (50% EtOAc/hexane); $^1$H NMR (CDCl$_3$, 270 MHz) δ 7.53 (d, J=8.6 Hz, 2H), 7.24 (m, 4H), 6.87 (m, 4H) 6.79 (d, J=8.9 Hz, 2H), 4.89 (dd, J=2.6, 9.5 Hz, 1H, H-3), 4.78 (d, J=10.5 Hz, 1H), 4.55 (m, 4H), 4.50 (s, 2H), 4.46 (d, J=11.5 Hz, 1H), 4.30 (m, 2H), 4.18 (dd, J=2.6, 3.4 Hz, 1H, H-4), 3.81 (s, 3H, OMe), 3.80 (s, 3H, OMe), 3.74 (m, 3H), 3.60 (t, J=4.6 Hz, 1H), 2.91 (d, J=3.4 Hz, 1H), 2.06 (s, 3H, OAc), 1.03 (m, 2H, $CH_2$—TMS), 0.04 (s, 9H, SiMe$_3$).

To a solution of 85 (1.30 9, 1.79 mmol) in 13 mL of CH$_2$Cl$_2$ at −35° C. is added pyridine (0.072 mL, 8.93 mmol) followed by triflic anhydride (0.451 mL, 2.68 mmol). The reaction is allowed to warm slowly to 0° C. and is then poured into saturated NaHCO$_3$ (50 mL), extracted with CH$_2$Cl$_2$ (3×30 mL), dried over Na$_2$SO$_4$, concentrated and purified by flash chromatography (25% EtOAc/hexane) to give 1.10 g (71%) of 2-(trimethylsilyl)ethyl 2-{4-[(3-O-acetyl-2,6-bis-O-(4-methoxybenzyl)-1-deoxy-4-O-trifluoromethanesulfonyl-β-D-galactopyranosyl)thio]phenoxy}acetate 86 as a colorless oil: $R_f$ 0.5 (25% EtOAc/hexane); $^1$H NMR (CDCl$_3$, 270 MHz) δ 7.48 (d, J=8.9 Hz, 2H), 7.24 (m, 4H), 6.84 (m, 6H), 5.33 (d, J=2.6 Hz, 1H, H-4), 5.00 (dd, J=2.6, 9.6 Hz, 1H, H-3), 4.76 (d, J=10.9 Hz, 1H), 4.40 (m, 5H), 4.31 (m, 3H), 3.81 (m, 1H), 3.81 ( s, 6H, 2X-OMe), 3.67 (ddd, J=2.3, 9.6, 9.6 Hz, 1H), 3.53 (dd, J=8.7, 8.7 Hz, 1H), 2.03 (s, 3H, OAc), 1.04 (m, 2H, $CH_2$—TMS), 0.01 (s, 9H, SiMe$_3$)

To a solution of 86 (1.10 g, 1.28 mmol) in 15 mL of DMF is added NaN$_3$ (831 mg, 12.8 mmol) The reaction is stirred at room temperature for 1.5 h and then poured into water (100 mL), extracted with CH$_2$Cl$_2$ (3×50 mL), dried over Na$_2$SO$_4$, concentrated and purified by flash chromatography (25% EtOAc/hexane) to give 0.96 g (99%) of 2-(trimethylsilyl)ethyl 2-{4-[(3-O-acetyl-4-azido-2,6-bis-O-(4-methoxybenzyl)-1,4-dideoxy-β-D-glucopyranosyl)thio]phenoxy}acetate 87 as a colorless oil: R$_f$0.5 (25% EtOAc/hexane); $^1$H NMR (CDCl$_3$, 270 MHz,) δ 7.51 (d, J=8.9 Hz, 2H), 7.23 (m, 4H), 6.91 (d, J=8.9 Hz, 2H), 6.86 (d, J=6.6 Hz, 2H), 6.79 (d, J=8.9 Hz, 2H), 5.13 (dd, J=9.2, 9.9 Hz, 1H, H-3), 4.77 (d, J=10.9 Hz, 1H), 4.51 (m, 6H), 4.30 (m, 2H) 3.82 (s, 3H, OMe), 3.80 ( s, 3H, OMe), 3.68 (m, 3H), 3.39 (dd, J=9.4, 9.4 Hz, 1H), 3.31 (m, 1H), 2.00 (s, 3H, OAc), 1.04 (m, 2H, CH$_2$—TMS), 0.05 (s, 9H, SiMe$_3$).

To a solution of 87 (370 mg, 0.49 mmol) in 10 mL of THF is added tetrabutylammonium fluoride solution (1M in THF, 2.46 mL, 2.46 mmol). The reaction is stirred at room temperature for 30 min and then diluted with EtOAc (25 mL) and washed with 0.5M HCl (20 mL) and saturated NaCl (20 mL). The aqueous layer is back-extracted with EtOAc (25 mL) and the organic layers are combined, dried over Na$_2$SO$_4$, concentrated, and purified by flash chromatography (0.3% AcOH, 10% MeOH, in EtOAc) to give 250 mg (78%) of 2-{4-[(3-O-acetyl-4-azido-2,6-bis-O-(4-methoxybenzyl)-1,4-dideoxy-β-D-glucopyranosyl)thio]phenoxy}acetic acid 88 as a white solid: R$_f$0.4 (0.3% AcOH, 10% MeOH/EtOAc); $^1$H NMR (CDCl$_3$, 300 MHz) δ 7.51 (d, J=8.8 Hz, 2H), 7.24 (m, 4H), 6.91 (d, J=8.8 Hz, 2H), 6.86 (d, J=8.4 Hz, 2H) 6.76 (d, J=8.8 Hz, 2H), 5.14 (dd, J=9.2, 9.2 Hz, 1H, H-3), 4.76 (d, J=9.6 Hz, 1H), 4.62 (s, 2H), 4.50 (m, 4H), 3.83 (s, 3H, OMe), 3.80 (s, 3H, OMe), 3.73 (m, 2H), 3.64 (dd, J=9.9, 9.9 Hz, 1H), 3.39 (dd, J=9.2, 9.5 Hz, 1H), 3.32 (m, 1H), 2.00 (s, 3H, OAc) $^{13}$C NMR (C$_6$D$_6$, 126 MHz) δ 170.4, 160.6, 160.5, 159.5, 135.6, 131.6, 125.5, 116.5, 114.8, 114.7, 88.3, 79.2, 78.4, 76.8, 75.1, 73.9, 70.0, 66.2, 61.7, 55.9, 30.9, 30.6, 30.5, 30.3, 30.0, 29.9, 29.7, 21.3; FABMS C$_{32}$H$_{35}$O$_{10}$N$_3$S calcd 676.1940, found 676.1960 7.30. 2-{4-[(3-O-acetyl-4,6-O-benzylidene-1deoxy-2-O-(4-methoxybenzyl)-β-D-galactopyranosyl)thio]phenoxy}acetic acid (95)

To a solution of 81, prepared as above (139 mg, 0.303 mmol) and 2,6-di-t-butyl-4-methyl pyridine (187 mg, 0.91 mmol) in 5 mL CH$_2$Cl$_2$, are added chlorotriphenylmethane (101 mg, 0.364 mmol) and silver trifluoromethanesulfonate (78 mg, 0.30 mmol). The reaction mixture is stirred at room temperature for 45 min and then is filtered though celite and washed with 10 mL of aqueous NaHCO$_3$. The aqueous solution is extracted with CH$_2$Cl$_2$ (2×10 mL) and the organic layers are combined and dried over Na$_2$SO$_4$, filtered and concentrated. The product is purified by flash chromatography (25% EtOAc/hexane) to give 171 mg (81%) of 1-deoxy-3,4-O-isopropylidene-1-{4-[2-(trimethylsilyl)ethoxymethoxy]phenylthio}-6-O-triphenylmethyl-β-D-galactopyranose 89 as white solid: R$_f$0.2 (25% EtOAc/hexane); $^1$H NMR (CDCl$_3$, 300 MHz) δ 7.53–7.40 (m, 8H), 7.31–7.21 (m, 9H), 6.95 (d, J=8.5 Hz, 2H), 5.19 (s, 2H), 4.29 (d, J=10.2 Hz, 1H, H-1), 4.14 (dd, J=5.6, 2.0 Hz, 1H, H-4), 4.02 (dd, J=6.9, 5.6 Hz, 1H, H-3), 3.73 (m, 3H), 3.56 (dd, J=9.6, 6.9 Hz, 1H, H-6), 3.48 (ddd, J=8.9, 6.9, 2.0 Hz, 1H, H-2), 3.36 (dd, J=9.6, 5.3 Hz, 1H, H-6), 2.37 (d, J=2.0 Hz, 1H, OH), 1.37 (s,3H), 1.31 (s, 3H), 0.96 (t, J=7.2 Hz, 2H), 0.00 (s, 9H)

To a solution of 89 (365 mg, 0.521 mmol) and tetrabutylammonium iodide (770 mg, 2.08 mmol) in 5 mL of DMF is added 4-methoxybenzyl chloride (0.422 mL, 4.17 mmol) and sodium hydride (19 mg, 0.782 mmol). The reaction is stirred at room temperature for one hour and then diluted with 50 mL of CH$_2$Cl$_2$, washed with brine (3×20 mL), dried over Na$_2$SO$_4$, filtered, and concentrated to afford a white solid which is purified by flash chromatography (12% EtOAc/hexane) to give 399 mg (93%) of 1-deoxy-3,4-O-isopropylidene-2-O-(4-methoxybenzyl)-1-{4-[2-(trimethylsily)-ethoxymethoxy]phenylthio}-6-O-triphenylmethyl-β-D-galactopyranose 90 as a white foam: R$_f$0.25 (12% EtOAc/hexane); $^1$H NMR (CDCl$_3$, 270 MHz) δ 7.51 (d, J=8.5 Hz, 2H), 7.48–7.45 (m, 6H), 7.34–7.20 (m, 11H), 6.91–6.87 (m, 4H), 5.16 (s, 2H), 4.76 (d, J=10.9 Hz, 1H), 4.62 (d, J=10.9 Hz, 1H), 4.40 (d, J=9.9 Hz, 1H, H-1), 4.19–4.10 (m, 2H), 3.80–3.70 (m, 5H), 3.58–3.53 (m, 2H), 3.45–3.39 (dd, J=6.3, 9.6 Hz, 1H, H-6), 3.36–3.32 (m, 1H), 1.36 (s, 3H), 1.32 (s, 3H), 0.95 (t, J=8.2 Hz, 2H), 0.00 (s, 9H).

To a solution of 90 (399 mg, 0.486 mmol) in 15 mL of methanol is added p-toluenesulfonic acid hydrate (69 mg, 0.365 mmol). The reaction mixture is stirred at room temperature for 4.5 h and then quenched by adding solid NaHCO$_3$ and then concentrated and purified by flash chromatography (3% methanol/EtOAc) to give 125 mg (65%) of 1-deoxy-1-(4-hydroxyphenylthio)-2-O-(4-methoxybenzyl)-β-D-galactopyranose 91 as a white solid: R$_f$0.5 (10% methanol/EtOAc); $^1$H NMR (CD$_3$OD, 270 MHz) δ 7.42–7.38 (m, 4H), 6.88 (d, J=8.9 Hz, 2 H), 6.71 (d, J=8.6 Hz, 2H), 4.74 (s, 2H), 4.42 (d, J=9.5 Hz, 1H, H-1), 3.86 (d, J=2.6 Hz, 1H), 3.79 (s, 3H, OCH$_3$), 3.77–3.70 (m, 2H), 3.61–3.45 (m, 3H).

To a solution of 91 (717 mg, 1.89 mmol) in 100 mL DMF is added benzaldehyde dimethyl acetal (1.4 mL, 9.12 mmol) and p-toluenesulfonic acid hydrate (36 mg, 0.189 mmol). The reaction mixture is stirred overnight at room temperature, quenched by adding solid sodium bicarbonate then concentrated in vacuo. The residue is purified by flash chromatography (60% EtOAc/hexane) to give 400 mg (43%) of 4,6-O-benzylidene-1-deoxy-1-(4-hydroxyphenylthio)-2-O-(4-methoxybenzyl)-β-D-galactopyranose 92 as a white solid: R$_f$0.2 (60% EtOAc/hexane); $^1$H NMR (CDCl$_3$, 270 MHz) δ 7.60 (d, J=8.8 Hz, 2H), 7.47–7.33 (m, 7H), 6.88 (d, J=8.4 Hz, 2H), 6.71 (d, J=8.8 Hz,. 2H), 5.53 (s, 1H), 5.17 (s, 1H) 4.75 (d, J=10.3 Hz, 1H), 4.64 (d, J=10.3 Hz, 1H) 4.49 (d, J=9.3 Hz, 1H, H-1), 4.37 (dd, J=12.4, 1.7 Hz, 1H, H-6), 4.20 (d, J=3.6 Hz, 1H, H-4), 4.02 (dd, J=12.4, 1.4 Hz, 1H, H-6), 3.80 (s, 3H, OCH$_3$), 3.76 (td, J=8.8, 3.7 Hz, 1H, H-3), 3.56 (t, J=9.1 Hz, 1H, H-2), 3.49 (m, 1H, H-5), 2.43 (d, J=8.4 Hz, 1H).

To a solution of 92 (400 mg, 0.806 mmol) in 80 mL of dry DMF is added 2-(trimethylsilyl)ethyl bromoacetate (478 mg, 2 mmol) followed by K$_2$CO$_3$ (111 mg, 0.806 mmol). The reaction mixture is stirred at 60° C. for 4 hr and then allowed to cool. The solution is diluted with 150 mL of EtOAc and washed with brine (3×40 ml), dried over Na$_2$SO$_4$, filtered, concentrated and purified by flash chromatography (50% EtOAc/hexane) to give 260 mg (53%) of 2-(trimethylsilyl)ethyl 2-{4-[(4,6-O-benzylidene-1-deoxy-2-O-(4-galactopyranosyl)thio]phenoxy}acetate 93 as a white solid: R$_f$0.3 (50% EtOAc/hexane); $^1$H NMR (CDCl$_3$, 270 MHz) δ 7.6 (d, J=8.8 Hz, 2H), 7.45–7.25 (m, 7H), 6.82 (d, J=8.5 Hz, 2H), 6.71 (d, J=8.8 Hz, 2H), 5.49 (s, 1H), 4.68 (d, J=10.3 Hz, 1H), 4.57 (d, J=9.9 Hz, 1H), 4.49 (s, 2H), 4.46 (d, J=9.5 Hz, 1H, H-1), 4.32 (dd, J=12.5, 1.5 Hz, 1H, H-6), 4.28–4.22 (m, 2H), 4.16 (d, J=3.3 Hz, 1H, H-4), 3.97 (dd, J=12.5, 1.5 Hz, 1H, H-6), 3.75 (s, 3H, OCH$_3$), 3.71 (td, J=8.4, 3.3 Hz, 1H, H-3), 3.52 (t, J=9.1 Hz, 1H, H-2), 3.44 (m, 1H, H-5), 2.35 (d, J=8.4 Hz, 1H, OH), 0.989–0.917 (m, 2H), 0.0 (s, 9H).

To a solution of 93 (260 mg, 0.41 mmol) in 50 mL of CH$_2$Cl$_2$ is added pyridine (0.140 mL, 1.64 mmol) and acetic anhydride (0.078 mL, 0.82 mmol). The reaction mixture is stirred at room temperature for 2 hr and quenched by adding 1 mL of methanol. The reaction mixture is washed with 20 mL of NaHCO$_3$ solution and the aqueous layer is extracted with CH$_2$Cl$_2$ (2×40 mL). The organic layers are combined, dried over Na$_2$SO$_4$, filtered, concentrated and purified by flash chromatography (50% EtOAc/hexane) to give 252 mg (91%) of 2-(trimethylsilyl)ethyl 2-{4-[(3-O-acetyl-4,6-O-benzylidene-1-deoxy-2-O-( 4-methoxybenzyl)-β-D-galactopyranosyl)thio]phenoxy}acetate 94 as a white solid: R$_f$0.4 (50% EtOAc/hexane); $^1$H NMR (CDCl$_3$, 270 MHz) δ 7.63 (d, J=8.9 Hz, 2H), 7.48–7.24 (m, 7H), 6.86 (d, J=8.6 Hz, 2H), 6.72 (d, J=8.9 Hz, 2H), 5.49 (s, 1H), 4.92 (dd, J=9.9, 3.3 Hz, 1H, H-3), 4.70 (d, J=10.2 Hz, 1H), 4.58 (d, J=9.6 Hz, 1H, H-1), 4.51 (s, 2H), 4.46 (d, J=10.2 Hz, 1H), 4.38–4.27 (m, 4H), 4.00 (bd, J=12.2 Hz, 1H, H-6), 3.84 (t, J=9.5 Hz, 1H, H-2), 3.79 (s, 3H, OCH$_3$), 3.55 (m, 1H, H-5), 2.03 (s, 3H), 1.07–1.00 (m, 2H), 0.05 (s, 9H).

To a solution of 94 (252 mg, 0.365 mmol) in 2 mL of THF is added tetrabutylammonium fluoride solution (1.0M in THF, 0.380 ml, 0.380 mmol) at room temperature. The reaction mixture is stirred for 5 mins and then directly loaded to a silica gel column and purified by flash chromatography (0.1% AcOH,10% methanol, in EtOAc) to give 196 mg (91%) of the title compound 95 as a white solid: R$_f$0.1 (0.1% AcOH,10% methanol/EtOAc); $^1$H NMR (CDCl$_3$, 270 MHz) δ 9.72 (bs, 1H), 7.57 (d, J=8.5 Hz, 2H), 7.47–7.29 (m, 5H), 7.26 (d, J=8.5 Hz, 2H), 6.86 (d, J=8.4 Hz, 2H), 6.83 (d, J=8.4 Hz, 2H), 5.48 (s, 1H), 4.92 (dd, J=9.5, 3.3 Hz, 1H, H-3), 4.73 (d, J=11.2 Hz, 1H), 4.57 (d, J=9.5 Hz, 1H, H-1), 4.50–4.38 (m, 3H), 4.37–4.31 (m, 2H), 4.00 (bd, J=12 Hz, 1H, H-6), 3.85 (t, J=9.5 Hz, 1H, H-2) 3.80 (s, 3H, OCH$_3$), 3.52 (m, 1H, H-5), 2.03 (s, 3H) $^{13}$C NMR (CDCl$_3$, 68 MHz) δ 172.3, 170.7, 159.5, 157.6, 138.0, 135,3, 130.5, 129.5, 129.1, 128.2, 126.5, 124.8, 115.3, 113.9, 100.8, 86.9, 75.7, 75.0, 74.0, 73.8, 69.5, 69.3, 65.0, 55.4, 21.1.

7.31 Attachment Of A Glycosyl Acceptor To A Resin Support

A number of glycosyl acceptors, to be used as nucleophiles for coupling to the hexose derivatives of the invention, are coupled to a solid support by the following general method: TentaGel S NH2 resin (0.500 g) is suspended in N-methylpyrrolidinone (NMP, 15 mL), and to this mixture is added acid 64 (0.115 g, 0.230 mmol), diisopropylethylamine (0.22 g, 1.3 mmol), and HOBT/HBTU solution (0.45M in DMF, 2.2 g, 0.93 mmol). The reaction mixture is then shaken for 2–5 h until the resin gives a negative Kaiser test. The resin is washed with CH$_2$Cl$_2$ (3×15 mL, 5 min), NMP (3×15 mL, 5 min), and DMF (3×15 mL, 5 min).

A solution of hydrazine in DMF (1:7 v/v, 24 mL) is added to the resin. The mixture is shaken for 9 h or until acetate hydrolysis is shown to be complete by IR analysis (KBr pellet). The resin is then washed with DMF (3×15 mL, 5 min), H$_2$O (3×15 mL, 5 min), methanol (3×15 mL, 5 min) and CH$_2$Cl$_2$ (3×15 mL, 5 min).

In the present embodiment, six glycosyl acceptors (glycosylated acids 64, 66, 76, 77, 88 and 95) are attached to six separate batches of resin (e.g., TentaGel) and deprotected using the procedure described above. Each batch of support-bound glycosyl resin can then be used in the subsequent glycosylation reaction after suspension in 15 mL of CH$_2$Cl$_2$, shaking for 15 min and drying on the lyophilizer for 12 h.

7.32. Procedure For Solid Phase Glycosylation

In a typical procedure, a predetermined portion (0.225 g) of each batch of resin is placed in a reaction vessel equipped with a glass-fritted bottom, suspended in 5 mL of CH$_2$Cl$_2$ and agitated by slowly bubbling argon through the glass frit for 10 min. The 1-sulfinyl hexose derivative 33 (0.145 g, 0.270 mmol) and 2,6-di-tert-butyl-4-methylpyridine (0.111 g, 0.540 mmol) are dissolved in toluene (10 mL). The toluene is subsequently removed in vacuo to remove any water that may be present in solution. The dissolution and drying step is repeated at least once more. The residue is then dried under vacuum for 1 h. Afterwards, the sulfoxide and base are dissolved in CH$_2$Cl$_2$ (10 mL) and added to the resin sample, e.g., the resin sample bearing glycosyl acceptor 64. The suspension is then cooled to −65° C., and a solution of trifluoromethanesulfonic anhydride (23 μL, 0.13 mmol) in 1 mL of CH$_2$Cl$_2$ is added dropwise over 10 min. The reaction mixture is allowed to warm to 0° C. over 1–2 h, quenched using saturated aqueous NaHCO$_3$ (10 mL) and agitated for 10 min. The resin is then washed sequentially with 10 mL portions (3×10 mL, 5 min for each portion) of the following solvents: NaHCO$_3$, H$_2$O, methanol, diethyl ether, CH$_2$Cl$_2$ and toluene. The resin is dried on the lyophilizer (in vacuo) for 12 h and resubjected to the glycosylation reaction conditions for a second time to ensure complete reaction.

The stereoselectivity of the glycosylation reaction is established by cleavage of the disaccharide from the resin using mercuric trifluoroacetate (2.0 mg), in methylene chloride (0.5 mL) and shaking for 30 seconds. The Hg(OCOCF$_3$)$_2$ treatment causes the hydrolytic cleavage of the thioacetal group. The resulting lactol is then compared with an authentic disaccharide, independently synthesized. The desired disaccharide is obtained in greater than 9:1 alpha:beta selectivity as judged by TLC (40% ethyl acetate in petroleum ether, Rf 0.3) and HPLC analysis.

Glycosylation reactions using the hexose derivatives 8, 11, D-25, L-25, 30 and 33, with any of the six resin samples obtained previously provide comparable stereoselectivities of at least bout 9:1, perhaps greater than 10:1.

Thus, using the above-described procedure, the twelve resin samples are glycosylated with the 1-sulfinyl hexose derivatives 5, 11, 13, D-25, L-25, 33, 37, 41, D-45, L-45, 51 and 53. All 12 portions of the resin are then combined, suspended in 15 mL of CH$_2$Cl$_2$, shaken for 15 min and dried on the lyophilizer for 12 h.

Other embodiments should be apparent to those of ordinary skill in view of the detailed disclosure provided herein, which embodiments would nonetheless fall within the scope and spirit of the present invention. Hence, the preceding preferred embodiments should not be construed as limiting the invention in any way.

What is claimed is:

1. A hexose of the formula

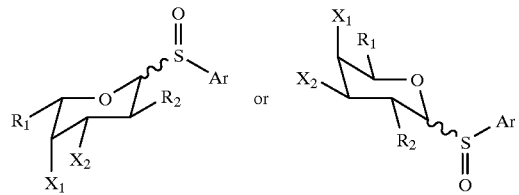

in which R$_1$ and R$_2$ may be the same or different and each represents a substituent comprising one or more of the elements hydrogen, carbon, nitrogen, oxygen, sulfur, or phosphorus; Ar of the —SOAr group represents an aromatic group; and X$_1$ and X$_2$ may be the same or different and together with the hexose carbon atoms to which they are attached form a cyclic structure.

2. The hexose of claim 1 in which R$_1$ represents a lower alkyl group or a protected or unprotected hydroxymethylene group.

3. The hexose of claim 1 in which R$_2$ represents a protected or unprotected hydroxyl group, a substituted or unsubstituted amine group, or an azide group.

4. The hexose of claim 1 in which Ar represents a substituted or unsubstituted phenyl group.

5. The hexose of claim 1 in which $X_1$ and $X_2$ together with the hexose carbon atoms to which they are attached form a five-membered ring.

6. The hexose of claim 1 in which $X_1$ and $X_2$ together with the hexose carbon atoms to which they are attached form a cyclic carbonate.

7. The hexose of claim 1 in which $X_1$ and $X_2$ together with the hexose carbon atoms to which they are attached form a cyclic ketal or cyclic acetal.

8. A method of making a compound having an α-(1,2-cis)-glycosidic linkage comprising:

(a) providing a glycosyl donor of the formula

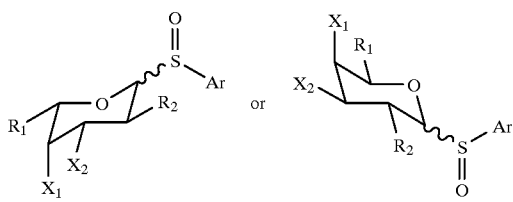

in which $R_1$ and $R_2$ may be the same or different and each represents a substituent comprising one or more of the elements hydrogen, carbon, nitrogen, oxygen, sulfur, or phosphorus; Ar of the —SOAr group represents an aromatic group; and $X_1$ and $X_2$ may be the same or different and together with the hexose carbon atoms to which they are attached form a cyclic structure; and (b) contacting said glycosyl donor with a compound having a nucleophilic group capable of displacing the —SOAr group.

9. The method of claim 8 which further comprises activating the —SOAr group to render it more susceptible to nucleophilic attack.

10. The method of claim 9 in which said activating step comprises contacting said glycosyl donor with an organic acid or anhydride.

11. The method of claim 8 in which said compound is bound to a solid support.

12. The method of claim 8 in which said compound includes an α-(1,6)-, α-(1,4)-, or α-(1,3)-disaccharide linkage.

* * * * *

UNITED STATES PATENT AND TRADEMARK OFFICE
CERTIFICATE OF CORRECTION

PATENT NO. : 6,040,433
DATED : March 21, 2000
INVENTOR(S) : Daniel E. Kahne, et al.

It is certified that error appears in the above-identified patent and that said Letters Patent is hereby corrected as shown below:

Column 1, line 6,

Insert under "Cross-Reference to Related Applications" the following statement:

--Aspects of the present invention were supported under Grant Number N00014-95-1-0011 awarded by the Department of Navy. The United States Government has certain rights in the invention.--

Signed and Sealed this

Nineteenth Day of December, 2000

Attest:

Q. TODD DICKINSON

*Attesting Officer*    *Commissioner of Patents and Trademarks*